US008022271B2

(12) United States Patent
Elumalai et al.

(10) Patent No.: US 8,022,271 B2
(45) Date of Patent: Sep. 20, 2011

(54) POLYUBIQUITIN RUBI3 PROMOTER AND 5' REGULATORY SEQUENCES

(75) Inventors: Sivamani Elumalai, Raleigh, NC (US); Rongda Qu, Cary, NC (US)

(73) Assignee: North Carolina State University, Raleigh, NC (US)

( * ) Notice: Subject to any disclaimer, the term of this patent is extended or adjusted under 35 U.S.C. 154(b) by 1455 days.

(21) Appl. No.: 10/555,491

(22) PCT Filed: May 14, 2004

(86) PCT No.: PCT/US2004/015286
§ 371 (c)(1), (2), (4) Date: May 10, 2006

(87) PCT Pub. No.: WO2004/104174
PCT Pub. Date: Dec. 2, 2004

(65) Prior Publication Data
US 2009/0106854 A1  Apr. 23, 2009

Related U.S. Application Data

(60) Provisional application No. 60/471,007, filed on May 16, 2003.

(51) Int. Cl.
*A01H 5/00* (2006.01)
*C12N 15/82* (2006.01)
*C12N 15/87* (2006.01)
*C12N 5/14* (2006.01)
*C12N 15/63* (2006.01)
*C07H 21/04* (2006.01)
*C07H 21/00* (2006.01)

(52) U.S. Cl. ..... 800/295; 800/278; 800/289; 435/320.1; 435/419; 435/468; 536/23.1; 536/23.6; 536/24.1

(58) Field of Classification Search .......................... None
See application file for complete search history.

(56) References Cited

U.S. PATENT DOCUMENTS

| 5,510,474 | A | 4/1996 | Quail et al. |
| 5,773,705 | A | 6/1998 | Vierstra et al. |
| 5,851,791 | A | 12/1998 | Vierstra et al. |
| 6,258,601 | B1 | 7/2001 | Monia et al. |
| 6,455,759 | B1 | 9/2002 | Vierstra et al. |
| 6,528,701 | B1 | 3/2003 | Wang et al. |
| 2002/0046415 | A1* | 4/2002 | Albert et al. ................. 800/278 |
| 2008/0114160 | A1* | 5/2008 | Boukharov et al. .......... 536/23.6 |

FOREIGN PATENT DOCUMENTS

WO   WO/03000898   * 1/2003

OTHER PUBLICATIONS

Garbarino et al. (Plant Physiol., 109:1371-1378, 1995).*
Kim et al. (Plant Molecular Biology, 24:105-117, 1994).*
Donald et al. (EMBO J. 9:1717-1726, 1990).*
Benfey et al. (Science 250:959-966, 1990).*
Wang et al. (Plant Sci., 156:201-211, Published 2000).*
Maniatis et al. (Molecular Cloning: A Laboratory Manual, Cold Spring Harbor Laboratory, 1982).*
Christensen et al.; "Ubiquitin promoter-based vectors for high-level expression of selectable and/or screenable marker genes in monocotyledonous plants", *Transgenic Research*, 1996, 5: 213-218.
Feng et al.; "Sequence and analysis of rice chromosome 4", *Nature*, 2002, 420: 316-320.
Garbarino et al.; "Isolation of a Polyubiquitin Promoter and Its Expression in Transgenic Potato Plants", *Plant Physiol*, 1995, 109: 1371-1378.
Sivamani et al.; "Isolation of promoters of a polyubiquitin, a histone, and a kinase gene from rice for grass transformation", Molecular Breeding of Forage and Turf 2003, Dallas, Texas May 18-22, 2003, 1 page.
Wang et al.; "Structure, expression and promoter activity of two polyubiquitin genes from rice (*Oryza sativa* L.)", Plant Science, 2000, 156: 201-211.
Binet et al., "Analysis of a sunflower polyubiquitin promoter by transient expression", *Plant Science*, 1991, 79: 87-94.
Binet et al., "Structure and expression of sunflower ubiquitin genes", *Plant Molecular Biology*, 1991, 17: 395-407.
Callis et al., "Ubiquitin and ubiquitin genes in higher plants", *Oxford Surveys of Plant Molecular & Cell Biology*, 1989, 6: 1-30.
Christensen et al., "Maize polyubiquitin genes: structure, thermal perturbation of expression and transcript splicing, and promoter activity following transfer to protoplasts by electroporation", *Plant Molecular Biology*, 1992, 18: 675-689.
Garbarino et al., "Isolation of a polyubiquitin promoter and its expression in transgenic potato plants", *Plant Physiol.*, 1995, 109: 1371-1378.
Garbarino et al., "Isolation of a ubiquitin-ribosomal protein gene (*ubi3*) from potato and expression of its promoter in transgenic plants", *Plant Molecular Biology*, 1994, 24: 119-127.
Genschik et al., "Structure and promoter activity of a stress and developmentally regulated polyubiquitin-encoding of *Nicotiana tabacum*", *Gene*, 1994, 148: 195-202.
Hondred et al., "Use of ubiquitin fusions to augment protein expression in transgenic plants", *Plant Physiology*, 1999, 119: 713-723.
Kawalleck et al., "Polyubiquitin gene expression and structural properties of the *ubi4-2* gene in *Petroselinum crispum*", *Plant Molecular Biology*, 1993, 21: 673-684.
Norris et al., "The intron of *Arabidopsis thaliana* polyubiquitin genes is conserved in location and is a quantitative determinant of chimeric gene expression", *Plant Molecular Biology*, 1993, 21: 895-906.

(Continued)

*Primary Examiner* — Vinod Kumar
(74) *Attorney, Agent, or Firm* — Myers Bigel Sibley & Sajovec, P.A.

(57) ABSTRACT

The present invention provides novel expression control elements and methods for expressing a heterologous nucleotide sequence of interest in plants. Isolated nucleic acids, expression cassettes and vectors comprising the expression control elements are provided. Also provided are transformed plants, plant tissues, plant cells, plant seed, and the like, comprising the isolated nucleic acids, expression cassettes and vectors of the invention. Further provided are methods of expressing a heterologous nucleotide sequence of interest in a plant, plant tissue, plant cell, and the like.

53 Claims, 16 Drawing Sheets

OTHER PUBLICATIONS

Rose et al., "Intro-mediated enhancement of gene expression independent of unique intron sequences and splicing", *Plant Physiology*, 2000, 122: 535-542.

Sivamani et al., "Rice plant (*Oryza sativa* L.) containing Rice tungro spherical virus (RTSV) coat protein transgenes are resistant to virus infection", *Molecular Breeding*, 1999, 5: 177-185.

Streatfield et al., "Analysis of the maize *polyubiquitin-1* promoter heat shock elements and generation of promoter variants with modified expression characteristics", *Transgenic Research*, 2004, 13: 299-312.

Wang et al., "Rice ubiquitin promoters: deletion analysis and potential usefulness in plant transformation systems", *Plant Cell Rep.*, 2003, 22: 129-134.

Wang et al., "Structure, expression and promoter activity of two polyubiquitin genes from rice (*Oryza sativa* L.)" *Plant Science,*'2000, 156: 201-211.

Wei et al., "Comparative expression analysis of two sugarcane polyubiquitin promoters and flanking sequences in transgenic plants", *J. Plant Physiol.*, 2003, 160: 1241-1251.

Sivamani E and Qu R. Expression enhancement of a rice polyubiquitin gene promoter. Plant Molecular Biology. 2006; 60: 225-239.

Dong S et al. Resistance of transgenic tall fescue to two major fungal diseases. Plant Science. 2007; 173: 501-509.

Lu J et al. Gene expression enhancement mediated by the 5' UTR intron of the rice *rubi3* gene varied remarkably among tissues in transgenic rice plants. Mol Genet Genomics. 2008; 279: 563-572.

Lu J et al. Activity of the 5' regulatory regions of the rice polyubiquitin *rubi3* gene in transgenic rice plants as analyzed by both *GUS* and *GFP* reporter genes. Plant Cell Rep. 2008; 27: 1587-1600.

Rose Ab et al. Promoter-proximal introns in *Arabidopsis thaliana* are enriched in dispersed signals that elevate gene expression. The Plant Cell. Mar. 2008; 20: 543-551.

Samadder P et al. Transcriptional and post-transcriptional enhancement of gene expression by the 5' UTR intron of rice *rubi3* gene in transgenic rice cells. Mol Genet Genomics. 2008; 279: 429-439.

Sivamani E et al. Sequence analysis of rice *rubi3* promoter gene expression cassettes for improved transgene expression. Plant Science. Article in press: 2009; 8 pp.

FIGS. 1A-C and FIGS. 3A-C, U.S. Appl. No. 10/555,491, filed May 10, 2006.

\* cited by examiner

```
   1 CCACCCAACCCCATATCGACAGAGGATGTGAAGAACAGGTAAATCACGCA
  51 GAAGAACCCATCTCTGATAGCAGCTATCGATTAGAACAACGAATCCATAT
 101 TGGGTCCGTGGGAAATACTTACTGCACAGGAAGGGGGGCGATCTGACGAG
 151 GCCCCGCCACCGGCCTCGACCCGAGGCCGAGGCCGACGAAGCGCCGGCGA
 201 GTACGGCGCCGCGGCGGCCTCTGCCCGTGCCCTCTGCGCGTGGGAGGGAG
 251 AGGCCGCGGTGGTGGGGCGCGCGCGCGCGCGCGCAGCTGGTGCGGCG
 301 GCGCGGGGGTCAGCCGCCGAGCCGGCGGCGACGGAGGAGCAGGGCGGCGT
 351 GGACGCGAACTTCCGATCGGTTGGTCAGAGTGCGCGAGTTGGGCTTAGCc
 401 aatTAGGTCTCAAcaatCTATTGGGCCGTAAAATTCATGGGCCCTGGTTT
 451 GTCTAGGCCcaatATCCCGTTCATTTCAGCCCACAAATATTTCCCCAGAG
 501 GATTATTAAGGCCCACACGCAGCTTATAGCAGATCAAGTACGATGTTTCC
 551 TGATCGTTGGATCGGAAACGTACGGTCTTGATCAGGCATGCCGACTTCGT
 601 CAAAGAGAGGCGGCATGACCTGACGCGGAGTTGGTTCCGGGCACCGTCTG
 651 GATGGTCGTACCGGGACCGGACACGTGTCGCGCCTCCAACTACATGGACA
 701 CGTGTGGTGCTGCCATTGGGCCGTACGCGTGGCGGTGACCGCACCGGATG
 751 CTGCCTCGCACCGCCTTGCCCACGCTTTATATAGAGAGGTTTTCTCTCCA
 801 TTAATCGCATAGCGAGTCGAATCGACCGAAGGGGAGGGGGAGCGAAGCTT
 851 TGCGTTCTCTAATCGCCTCGTCAAGGTAACTAATCAATCACCTCGTCCTA
 901 ATCCTCGAATCTCTCGTGGTGCCCGTCTAATCTCGCGATTTTGATGCTCG
 951 TGGTGGAAAGCGTAGGAGGATCCCGTGCGAGTTAGTCTCAATCTCTCAGG
1001 GTTTCGTGCGATTTTAGGGTGATCCACCTCTTAATCGAGTTACGGTTTCG
1051 TGCGATTTTAGGGTAATCCTCTTAATCTCTCATTGATTTAGGGTTTCGTG
1101 AGAATCGAGGTAGGGATCTGTGTTATTTATATCGATCTAATAGATGGATT
1151 GGTTTTGAGATTGTTCTGTCAGATGGGGATTGTTTCGATATATTACCCTA
1201 ATGATGTGTCAGATGGGGATTGTTTCGATATATTACCCTAATGATGTGTC
1251 AGATGGGGATTGTTTCGATATATTACCCTAATGATGGATAATAAGAGTAG
1301 TTCACAGTTATGTTTTGATCCTGCCACATAGTTTGAGTTTTGTGATCAGA
1351 TTTAGTTTTACTTATTTGTGCTTAGTTCGGATGGGATTGTTCTGATATTG
1401 TTCCAATAGATGAATAGCTCGTTAGGTTAAAATCTTTAGGTTGAGTTAGG
1451 CGACACATAGTTTATTTCCTCTGGATTTGGATTGGAATTGTGTTCTTAGT
1501 TTTTTTCCCCTGGATTTGGATTGGAATTGTGTGGAGCTGGGTTAGAGAAT
1551 TACATCTGTATCGTGTACACCTACTTGAACTGTAGAGCTTGGGTTCTAAG
1601 GTCAATTTAATCTGTATTGTATCTGGCTCTTTGCCTAGTTGAACTGTAGT
1651 GCTGATGTTGTACTGTGTTTTTTACCCGTTTTATTTGCTTTACTCGTGC
1701 AAATCAAATCTGTCAGATGCTAGAACTAGGTGGCTTTATTCTGTGTTCTT
1751 ACATAGATCTGTTGTCCTGTAGTTACTTATGTCAGTTTTGTTATTATCTG
1801 AAGATATTTTGGTTGTTGCTTGTTGATGTGGTGTGAGCTGTGAGCAGCG
1851 CTCTTATGATTAATGATGCTGTCCAATTGTAGTGTAGTATGATGTGATTG
1901 ATATGTTCATCTATTTTGAGCTGACAGTACCGATATCGTAGGATCTGGTG
1951 CCAACTTATTCTCCAGCTGCTTTTTTTACCTATGTTAATTCCAATCCTT
2001 TCTTGCCTCTTCCAG (SEQ ID NO:1)
```

*FIG. 1A*

```
  1 CCACCCAACCCCATATCGACAGAGGATGTGAAGAACAGGTAAATCACGCA
 51 GAAGAACCCATCTCTGATAGCAGCTATCGATTAGAACAACGAATCCATAT
101 TGGGTCCGTGGGAAATACTTACTGCACAGGAAGGGGGCGATCTGACGAG
151 GCCCCGCCACCGGCCTCGACCCGAGGCCGAGGCCGACGAAGCGCCGGCGA
201 GTACGGCGCCGCGGCGGCCTCTGCCCGTGCCCTCTGCGCGTGGGAGGGAG
251 AGGCCGCGGTGGTGGGGGCGCGCGCGCGCGCGCGCAGCTGGTGCGGCG
301 GCGCGGGGGTCAGCCGCCGAGCCGGCGGCGACGGAGGAGCAGGGCGGCGT
351 GGACGCGAACTTCCGATCGGTTGGTCAGAGTGCGCGAGTTGGGCTTAGCc
401 aatTAGGTCTCAAcaatCTATTGGGCCGTAAAATTCATGGGCCCTGGTTT
451 GTCTAGGCCcaatATCCCGTTCATTTCAGCCCACAAATATTTCCCCAGAG
501 GATTATTAAGGCCCACACGCAGCTTATAGCAGATCAAGTACGATGTTTCC
551 TGATCGTTGGATCGGAAACGTACGGTCTTGATCAGGCATGCCGACTTCGT
601 CAAAGAGAGGCGGCATGACCTGACGCGGAGTTGGTTCCGGGCACCGTCTG
651 GATGGTCGTACCGGGACCGGACACGTGTCGCGCCTCCAACTACATGGACA
701 CGTGTGGTGCTGCCATTGGGCCGTACGCGTGGCGGTGACCGCACCGGATG
751 CTGCCTCGCACCGCCTTGCCCACGCTTTATATAGAGAGGTTTTCTCTCCA
801 TTAATCGCATAGCGAGTCGAATCGACCGAAGGGGAGGGGGAGCGAAGCTT
851 TGCGTTCTCTAATCGCCTCGTCAAG (SEQ ID NO:2)
```
*FIG. 1B*

```
   1 GTAACTAATCAATCACCTCGTCCTAATCCTCGAATCTCTCGTGGTGCCCG
  51 TCTAATCTCGCGATTTTGATGCTCGTGGTGGAAAGCGTAGGAGGATCCCG
 101 TGCGAGTTAGTCTCAATCTCTCAGGGTTTCGTGCGATTTTAGGGTGATCC
 151 ACCTCTTAATCGAGTTACGGTTTCGTGCGATTTTAGGGTAATCCTCTTAA
 201 TCTCTCATTGATTTAGGGTTTCGTGAGAATCGAGGTAGGGATCTGTGTTA
 251 TTTATATCGATCTAATAGATGGATTGGTTTTGAGATTGTTCTGTCAGATG
 301 GGGATTGTTTCGATATATTACCCTAATGATGTGTCAGATGGGGATTGTTT
 351 CGATATATTACCCTAATGATGTGTCAGATGGGGATTGTTTCGATATATTA
 401 CCCTAATGATGGATAATAAGAGTAGTTCACAGTTATGTTTTGATCCTGCC
 451 ACATAGTTTGAGTTTTGTGATCAGATTTAGTTTTACTTATTTGTGCTTAG
 501 TTCGGATGGGATTGTTCTGATATTGTTCCAATAGATGAATAGCTCGTTAG
 551 GTTAAAATCTTTAGGTTGAGTTAGGCGACACATAGTTTATTTCCTCTGGA
 601 TTTGGATTGGAATTGTGTTCTTAGTTTTTTTCCCCTGGATTTGGATTGGA
 651 ATTGTGTGGAGCTGGGTTAGAGAATTACATCTGTATCGTGTACACCTACT
 701 TGAACTGTAGAGCTTGGGTTCTAAGGTCAATTTAATCTGTATTGTATCTG
 751 GCTCTTTGCCTAGTTGAACTGTAGTGCTGATGTTGTACTGTGTTTTTTA
 801 CCCGTTTTATTTGCTTTACTCGTGCAAATCAAATCTGTCAGATGCTAGAA
 851 CTAGGTGGCTTTATTCTGTGTTCTTACATAGATCTGTTGTCCTGTAGTTA
 901 CTTATGTCAGTTTTGTTATTATCTGAAGATATTTTTGGTTGTTGCTTGTT
 951 GATGTGGTGTGAGCTGTGAGCAGCGCTCTTATGATTAATGATGCTGTCCA
1001 ATTGTAGTGTAGTATGATGTGATTGATATGTTCATCTATTTTGAGCTGAC
1051 AGTACCGATATCGTAGGATCTGGTGCCAACTTATTCTCCAGCTGCTTTTT
1101 TTTACCTATGTTAATTCCAATCCTTTCTTGCCTCTTCCAG
     (SEQ ID NO:3)
```
*FIG. 1C*

```
   1 CCACCCAACCCCATATCGACAGAGGATGTGAAGAACAGGTAAATCACGCA
  51 GAAGAACCCATCTCTGATAGCAGCTATCGATTAGAACAACGAATCCATAT
 101 TGGGTCCGTGGGAAATACTTACTGCACAGGAAGGGGGGCGATCTGACGAG
 151 GCCCGCCACCGGCCTCGACCCGAGGCCGAGGCCGACGAAGCGCCGGCGA
 201 GTACGGCGCCGCGGCGGCCTCTGCCCGTGCCCTCTGCGCGTGGGAGGGAG
 251 AGGCCGCGGTGGTGGGGCGCGCGCGCGCGCGCGCAGCTGGTGCGGCG
 301 GCGCGGGGGTCAGCCGCCGAGCCGGCGGCGACGGAGGAGCAGGGCGGCGT
 351 GGACGCGAACTTCCGATCGGTTGGTCAGAGTGCGCGAGTTGGGCTTAGCc
 401 aatTAGGTCTCAAcaatCTATTGGGCCGTAAAATTCATGGGCCCTGGTTT
 451 GTCTAGGCCcaatATCCCGTTCATTTCAGCCCACAAATATTTCCCCAGAG
 501 GATTATTAAGGCCCACACGCAGCTTATAGCAGATCAAGTACGATGTTTCC
 551 TGATCGTTGGATCGGAAACGTACGGTCTTGATCAGGCATGCCGACTTCGT
 601 CAAAGAGAGGCGGCATGACCTGACGCGGAGTTGGTTCCGGGCACCGTCTG
 651 GATGGTCGTACCGGGACCGGACACGTGTCGCGCCTCCAACTACATGGACA
 701 CGTGTGGTGCTGCCATTGGGCCGTACGCGTGGCGGTGACCGCACCGGATG
 751 CTGCCTCGCACCGCCTTGCCCACGCTTTATATAGAGAGGTTTTCTCTCCA
 801 TTAATCGCATAGCGAGTCGAATCGACCGAAGGGGAGGGGGAGCGAAGCTT
 851 TGCGTTCTCTAATCGCCTCGTCAAGGTAACTAATCAATCACCTCGTCCTA
 901 ATCCTCGAATCTCTCGTGGTGCCCGTCTAATCTCGCGATTTTGATGCTCG
 951 TGGTGGAAAGCGTAGGAGGATCCCGTGCGAGTTAGTCTCAATCTCTCAGG
1001 GTTTCGTGCGATTTTAGGGTGATCCACCTCTTAATCGAGTTACGGTTTCG
1051 TGCGATTTTAGGGTAATCCTCTTAATCTCTCATTGATTTAGGGTTTCGTG
1101 AGAATCGAGGTAGGGATCTGTGTTATTTATATCGATCTAATAGATGGATT
1151 GGTTTTGAGATTGTTCTGTCAGATGGGGATTGTTTCGATATATTACCCTA
1201 ATGATGTGTCAGATGGGGATTGTTTCGATATATTACCCTAATGATGTGTC
1251 AGATGGGGATTGTTTCGATATATTACCCTAATGATGGATAATAAGAGTAG
1301 TTCACAGTTATGTTTTGATCCTGCCACATAGTTTGAGTTTTGTGATCAGA
1351 TTTAGTTTTACTTATTTGTGCTTAGTTCGGATGGGATTGTTCTGATATTG
1401 TTCCAATAGATGAATAGCTCGTTAGGTTAAAATCTTTAGGTTGAGTTAGG
1451 CGACACATAGTTTATTTCCTCTGGATTTGGATTGGAATTGTGTTCTTAGT
1501 TTTTTTCCCTGGATTTGGATTGGAATTGTGTGGAGCTGGGTTAGAGAAT
1551 TACATCTGTATCGTGTACACCTACTTGAACTGTAGAGCTTGGGTTCTAAG
1601 GTCAATTTAATCTGTATTGTATCTGGCTCTTTGCCTAGTTGAACTGTAGT
1651 GCTGATGTTGTACTGTGTTTTTTACCCGTTTTATTTGCTTTACTCGTGC
1701 AAATCAAATCTGTCAGATGCTAGAACTAGGTGGCTTTATTCTGTGTTCTT
1751 ACATAGATCTGTTGTCCTGTAGTTACTTATGTCAGTTTTGTTATTATCTG
1801 AAGATATTTTGGTTGTTGCTTGTTGATGTGGTGTGAGCTGTGAGCAGCG
1851 CTCTTATGATTAATGATGCTGTCCAATTGTAGTGTAGTATGATGTGATTG
1901 ATATGTTCATCTATTTTGAGCTGACAGTACCGATATCGTAGGATCTGGTG
1951 CCAACTTATTCTCCAGCTGCTTTTTTTTACCTATGTTAATTCCAATCCTT
2001 TCTTGCCTCTTCCAGATGCAGATA       (SEQ ID NO:17)
```

FIG. 1D

```
   1 CCACCCAACCCCATATCGACAGAGGATGTGAAGAACAGGTAAATCACGCA
  51 GAAGAACCCATCTCTGATAGCAGCTATCGATTAGAACAACGAATCCATAT
 101 TGGGTCCGTGGGAAATACTTACTGCACAGGAAGGGGGCGATCTGACGAG
 151 GCCCCGCCACCGGCCTCGACCCGAGGCCGAGGCCGACGAAGCGCCGGCGA
 201 GTACGGCGCCGCGGCGGCCTCTGCCCGTGCCCTCTGCGCGTGGGAGGGAG
 251 AGGCCGCGGTGGTGGGGGCGCGCGCGCGCGCGCGCAGCTGGTGCGGCG
 301 GCGCGGGGGTCAGCCGCCGAGCCGGCGGCGACGGAGGAGCAGGGCGGCGT
 351 GGACGCGAACTTCCGATCGGTTGGTCAGAGTGCGCGAGTTGGGCTTAGCc
 401 aatTAGGTCTCAAcaatCTATTGGGCCGTAAAATTCATGGGCCCTGGTTT
 451 GTCTAGGCCcaatATCCCGTTCATTTCAGCCCACAAATATTTCCCCAGAG
 501 GATTATTAAGGCCCACACGCAGCTTATAGCAGATCAAGTACGATGTTTCC
 551 TGATCGTTGGATCGGAAACGTACGGTCTTGATCAGGCATGCCGACTTCGT
 601 CAAAGAGAGGCGGCATGACCTGACGCGGAGTTGGTTCCGGGCACCGTCTG
 651 GATGGTCGTACCGGGACCGGACACGTGTCGCGCCTCCAACTACATGGACA
 701 CGTGTGGTGCTGCCATTGGGCCGTACGCGTGGCGGTGACCGCACCGGATG
 751 CTGCCTCGCACCGCCTTGCCCACGCTTTATATAGAGAGGTTTTCTCTCCA
 801 TTAATCGCATAGCGAGTCGAATCGACCGAAGGGGAGGGGGAGCGAAGCTT
 851 TGCGTTCTCTAATCGCCTCGTCAAGGTAACTAATCAATCACCTCGTCCTA
 901 ATCCTCGAATCTCTCGTGGTGCCCGTCTAATCTCGCGATTTGATGCTCG
 951 TGGTGGAAAGCGTAGGAGGATCCCGTGCGAGTTAGTCTCAATCTCTCAGG
1001 GTTTCGTGCGATTTTAGGGTGATCCACCTCTTAATCGAGTTACGGTTTCG
1051 TGCGATTTTAGGGTAATCCTCTTAATCTCTCATTGATTTAGGGTTTCGTG
1101 AGAATCGAGGTAGGGATCTGTGTTATTTATATCGATCTAATAGATGGATT
1151 GGTTTTGAGATTGTTCTGTCAGATGGGGATTGTTTCGATATATTACCCTA
1201 ATGATGTGTCAGATGGGGATTGTTTCGATATATTACCCTAATGATGTGTC
1251 AGATGGGGATTGTTTCGATATATTACCCTAATGATGGATAATAAGAGTAG
1301 TTCACAGTTATGTTTTGATCCTGCCACATAGTTTGAGTTTTGTGATCAGA
1351 TTTAGTTTTACTTATTTGTGCTTAGTTCGGATGGGATTGTTCTGATATTG
1401 TTCCAATAGATGAATAGCTCGTTAGGTTAAAATCTTTAGGTTGAGTTAGG
1451 CGACACATAGTTTATTTCCTCTGGATTTGGATTGGAATTGTGTTCTTAGT
1501 TTTTTTCCCTGGATTTGGATTGGAATTGTGTGGAGCTGGGTTAGAGAAT
1551 TACATCTGTATCGTGTACACCTACTTGAACTGTAGAGCTTGGGTTCTAAG
1601 GTCAATTTAATCTGTATTGTATCTGGCTCTTTGCCTAGTTGAACTGTAGT
1651 GCTGATGTTGTACTGTGTTTTTTACCCGTTTTATTTGCTTTACTCGTGC
1701 AAATCAAATCTGTCAGATGCTAGAACTAGGTGGCTTTATTCTGTGTTCTT
1751 ACATAGATCTGTTGTCCTGTAGTTACTTATGTCAGTTTTGTTATTATCTG
1801 AAGATATTTTGGTTGTTGCTTGTTGATGTGGTGTGAGCTGTGAGCAGCG
1851 CTCTTATGATTAATGATGCTGTCCAATTGTAGTGTAGTATGATGTGATTG
1901 ATATGTTCATCTATTTTGAGCTGACAGTACCGATATCGTAGGATCTGGTG
1951 CCAACTTATTCTCCAGCTGCTTTTTTTTACCTATGTTAATTCCAATCCTT
2001 TCTTGCCTCTTCCAGATACAGATA (SEQ ID NO:18)
```

FIG. 1E

```
   1 CCACCCAACCCCATATCGACAGAGGATGTGAAGAACAGGTAAATCACGCA
  51 GAAGAACCCATCTCTGATAGCAGCTATCGATTAGAACAACGAATCCATAT
 101 TGGGTCCGTGGGAAATACTTACTGCACAGGAAGGGGGCGATCTGACGAG
 151 GCCCCGCCACCGGCCTCGACCCGAGGCCGAGGCCGACGAAGCGCCGGCGA
 201 GTACGGCGCCGCGGCGGCCTCTGCCCGTGCCCTCTGCGCGTGGGAGGGAG
 251 AGGCCGCGGTGGTGGGGGCGCGCGCGCGCGCGCGCAGCTGGTGCGGCG
 301 GCGCGGGGGTCAGCCGCCGAGCCGGCGGCGACGGAGGAGCAGGGCGGCGT
 351 GGACGCGAACTTCCGATCGGTTGGTCAGAGTGCGCGAGTTGGGCTTAGCc
 401 aatTAGGTCTCAAcaatCTATTGGGCCGTAAAATTCATGGGCCCTGGTTT
 451 GTCTAGGCCcaatATCCCGTTCATTTCAGCCCACAAATATTTCCCCAGAG
 501 GATTATTAAGGCCCACACGCAGCTTATAGCAGATCAAGTACGATGTTTCC
 551 TGATCGTTGGATCGGAAACGTACGGTCTTGATCAGGCATGCCGACTTCGT
 601 CAAAGAGAGGCGGCATGACCTGACGCGGAGTTGGTTCCGGGCACCGTCTG
 651 GATGGTCGTACCGGGACCGGACACGTGTCGCGCCTCCAACTACATGGACA
 701 CGTGTGGTGCTGCCATTGGGCCGTACGCGTGGCGGTGACCGCACCGGATG
 751 CTGCCTCGCACCGCCTTGCCCACGCTTTATATAGAGAGGTTTTCTCTCCA
 801 TTAATCGCATAGCGAGTCGAATCGACCGAAGGGGAGGGGGAGCGAAGCTT
 851 TGCGTTCTCTAATCGCCTCGTCAAGGTAACTAATCAATCACCTCGTCCTA
 901 ATCCTCGAATCTCTCGTGGTGCCCGTCTAATCTCGCGATTTTGATGCTCG
 951 TGGTGGAAAGCGTAGGAGGATCCCGTGCGAGTTAGTCTCAATCTCTCAGG
1001 GTTTCGTGCGATTTTAGGGTGATCCACCTCTTAATCGAGTTACGGTTTCG
1051 TGCGATTTTAGGGTAATCCTCTTAATCTCTCATTGATTTAGGGTTTCGTG
1101 AGAATCGAGGTAGGGATCTGTGTTATTTATATCGATCTAATAGATGGATT
1151 GGTTTTGAGATTGTTCTGTCAGATGGGGATTGTTTCGATATATTACCCTA
1201 ATGATGTGTCAGATGGGGATTGTTTCGATATATTACCCTAATGATGTGTC
1251 AGATGGGGATTGTTTCGATATATTACCCTAATGATGGATAATAAGAGTAG
1301 TTCACAGTTATGTTTTGATCCTGCCACATAGTTTGAGTTTTGTGATCAGA
1351 TTTAGTTTTACTTATTTGTGCTTAGTTCGGATGGGATTGTTCTGATATTG
1401 TTCCAATAGATGAATAGCTCGTTAGGTTAAAATCTTTAGGTTGAGTTAGG
1451 CGACACATAGTTTATTTCCTCTGGATTTGGATTGGAATTGTGTTCTTAGT
1501 TTTTTTCCCTGGATTTGGATTGGAATTGTGTGGAGCTGGGTTAGAGAAT
1551 TACATCTGTATCGTGTACACCTACTTGAACTGTAGAGCTTGGGTTCTAAG
1601 GTCAATTTAATCTGTATTGTATCTGGCTCTTTGCCTAGTTGAACTGTAGT
1651 GCTGATGTTGTACTGTGTTTTTTTACCCGTTTTATTGCTTTACTCGTGC
1701 AAATCAAATCTGTCAGATGCTAGAACTAGGTGGCTTTATTCTGTGTTCTT
1751 ACATAGATCTGTTGTCCTGTAGTTACTTATGTCAGTTTTGTTATTATCTG
1801 AAGATATTTTGGTTGTTGCTTGTTGATGTGGTGTGAGCTGTGAGCAGCG
1851 CTCTTATGATTAATGATGCTGTCCAATTGTAGTGTAGTATGATGTGATTG
1901 ATATGTTCATCTATTTTGAGCTGACAGTACCGATATCGTAGGATCTGGTG
1951 CCAACTTATTCTCCAGCTGCTTTTTTTTACCTATGTTAATTCCAATCCTT
2001 TCTTGCCTCTTCCAGATTCAGATA (SEQ ID NO:19)
```

*FIG. 1F*

```
   1 CCACCCAACCCCATATCGACAGAGGATGTGAAGAACAGGTAAATCACGCA
  51 GAAGAACCCATCTCTGATAGCAGCTATCGATTAGAACAACGAATCCATAT
 101 TGGGTCCGTGGGAAATACTTACTGCACAGGAAGGGGGGCGATCTGACGAG
 151 GCCCCGCCACCGGCCTCGACCCGAGGCCGAGGCCGACGAAGCGCCGGCGA
 201 GTACGGCGCCGCGGCGGCCTCTGCCCGTGCCCTCTGCGCGTGGGAGGGAG
 251 AGGCCGCGGTGGTGGGGGCGCGCGCGCGCGCGCGCAGCTGGTGCGGCG
 301 GCGCGGGGGTCAGCCGCCGAGCCGGCGGCGACGGAGGAGCAGGGCGGCGT
 351 GGACGCGAACTTCCGATCGGTTGGTCAGAGTGCGCGAGTTGGGCTTAGCc
 401 aatTAGGTCTCAAcaatCTATTGGGCCGTAAAATTCATGGGCCCTGGTTT
 451 GTCTAGGCCcaatATCCCGTTCATTTCAGCCCACAAATATTTCCCCAGAG
 501 GATTATTAAGGCCCACACGCAGCTTATAGCAGATCAAGTACGATGTTTCC
 551 TGATCGTTGGATCGGAAACGTACGGTCTTGATCAGGCATGCCGACTTCGT
 601 CAAAGAGAGGCGGCATGACCTGACGCGGAGTTGGTTCCGGGCACCGTCTG
 651 GATGGTCGTACCGGGACCGGACACGTGTCGCGCCTCCAACTACATGGACA
 701 CGTGTGGTGCTGCCATTGGGCCGTACGCGTGGCGGTGACCGCACCGGATG
 751 CTGCCTCGCACCGCCTTGCCCACGCTTATATAGAGAGGTTTTCTCTCCA
 801 TTAATCGCATAGCGAGTCGAATCGACCGAAGGGGAGGGGGAGCGAAGCTT
 851 TGCGTTCTCTAATCGCCTCGTCAAGGTAACTAATCAATCACCTCGTCCTA
 901 ATCCTCGAATCTCTCGTGGTGCCCGTCTAATCTCGCGATTTGATGCTCG
 951 TGGTGGAAAGCGTAGGAGGATCCCGTGCGAGTTAGTCTCAATCTCTCAGG
1001 GTTTCGTGCGATTTAGGGTGATCCACCTCTTAATCGAGTTACGGTTTCG
1051 TGCGATTTAGGGTAATCCTCTTAATCTCTCATTGATTTAGGGTTTCGTG
1101 AGAATCGAGGTAGGGATCTGTGTTATTTATATCGATCTAATAGATGGATT
1151 GGTTTTGAGATTGTTCTGTCAGATGGGGATTGTTTCGATATATTACCCTA
1201 ATGATGTGTCAGATGGGGATTGTTTCGATATATTACCCTAATGATGTGTC
1251 AGATGGGGATTGTTTCGATATATTACCCTAATGATGGATAATAAGAGTAG
1301 TTCACAGTTATGTTTTGATCCTGCCACATAGTTTGAGTTTTGTGATCAGA
1351 TTTAGTTTTACTTATTTGTGCTTAGTTCGGATGGGATTGTTCTGATATTG
1401 TTCCAATAGATGAATAGCTCGTTAGGTTAAAATCTTTAGGTTGAGTTAGG
1451 CGACACATAGTTTATTTCCTCTGGATTTGGATTGGAATTGTGTTCTTAGT
1501 TTTTTTCCCTGGATTTGGATTGGAATTGTGTGGAGCTGGGTTAGAGAAT
1551 TACATCTGTATCGTGTACACCTACTTGAACTGTAGAGCTTGGGTTCTAAG
1601 GTCAATTTAATCTGTATTGTATCTGGCTCTTTGCCTAGTTGAACTGTAGT
1651 GCTGATGTTGTACTGTGTTTTTTACCCGTTTTATTTGCTTTACTCGTGC
1701 AAATCAAATCTGTCAGATGCTAGAACTAGGTGGCTTTATTCTGTGTTCTT
1751 ACATAGATCTGTTGTCCTGTAGTTACTTATGTCAGTTTTGTTATTATCTG
1801 AAGATATTTTGGTTGTTGCTTGTTGATGTGGTGTGAGCTGTGAGCAGCG
1851 CTCTTATGATTAATGATGCTGTCCAATTGTAGTGTAGTATGATGTGATTG
1901 ATATGTTCATCTATTTTGAGCTGACAGTACCGATATCGTAGGATCTGGTG
1951 CCAACTTATTCTCCAGCTGCTTTTTTTTACCTATGTTAATTCCAATCCTT
2001 TCTTGCCTCTTCCAG ATCCAGATA  (SEQ ID NO:20)
```

*FIG. 1G*

```
   1 CCACCCAACCCCATATCGACAGAGGATGTGAAGAACAGGTAAATCACGCA
  51 GAAGAACCCATCTCTGATAGCAGCTATCGATTAGAACAACGAATCCATAT
 101 TGGGTCCGTGGGAAATACTTACTGCACAGGAAGGGGGGCGATCTGACGAG
 151 GCCCCGCCACCGGCCTCGACCCGAGGCCGAGGCCGACGAAGCGCCGGCGA
 201 GTACGGCGCCGCGGCGGCCTCTGCCCGTGCCCTCTGCGCGTGGGAGGGAG
 251 AGGCCGCGGTGGTGGGGCGCGCGCGCGCGCGCGCAGCTGGTGCGGCG
 301 GCGCGGGGGTCAGCCGCCGAGCCGGCGGCGACGGAGGAGCAGGGCGGCGT
 351 GGACGCGAACTTCCGATCGGTTGGTCAGAGTGCGCGAGTTGGGCTTAGCc
 401 aatTAGGTCTCAAcaatCTATTGGGCCGTAAAATTCATGGGCCCTGGTTT
 451 GTCTAGGCCcaatATCCCGTTCATTTCAGCCCACAAATATTTCCCCAGAG
 501 GATTATTAAGGCCCACACGCAGCTTATAGCAGATCAAGTACGATGTTTCC
 551 TGATCGTTGGATCGGAAACGTACGGTCTTGATCAGGCATGCCGACTTCGT
 601 CAAAGAGAGGCGGCATGACCTGACGCGGAGTTGGTTCCGGGCACCGTCTG
 651 GATGGTCGTACCGGGACCGGACACGTGTCGCGCCTCCAACTACATGGACA
 701 CGTGTGGTGCTGCCATTGGGCCGTACGCGTGGCGGTGACCGCACCGGATG
 751 CTGCCTCGCACCGCCTTGCCCACGCTTTATATAGAGAGGTTTTCTCTCCA
 801 TTAATCGCATAGCGAGTCGAATCGACCGAAGGGGAGGGGGAGCGAAGCTT
 851 TGCGTTCTCTAATCGCCTCGTCAAGGTAACTAATCAATCACCTCGTCCTA
 901 ATCCTCGAATCTCTCGTGGTGCCCGTCTAATCTCGCGATTTTGATGCTCG
 951 TGGTGGAAAGCGTAGGAGGATCGATCTGTTGTCCTGTAGTTACTTATGTC
1001 AGTTTTGTTATTATCTGAAGATATTTTTGGTTGTTGCTTGTTGATGTGGT
1051 GTGAGCTGTGAGCAGCGCTCTTATGATTAATGATGCTGTCCAATTGTAGT
1101 GTAGTATGATGTGATTGATATGTTCATCTATTTTGAGCTGACAGTACCGA
1151 TATCGTAGGATCTGGTGCCAACTTATTCTCCAGCTGCTTTTTTTTACCTA
1201 TGTTAATTCCAATCCTTTCTTGCCTCTTCCAGATCCAGATA
     (SEQ ID NO:27)
```

FIG. 1H

```
   1 acacccaaccccatatcgacagaggatgtgaagaacaggtaaatcacgca
  51 gaagaacccatctctgatagcagctatcgattagaacaacgaatccatat
 101 tgggtccgtgggaaatacttactgcacaggaaggggggcgatctgacgag
 151 gccccgccaccggcctcgacccgaggccgaggccgacgaagcgccggcga
 201 gtacggcgccgcggcggcctctgcccgtgcctctgcgcgtgggagggag
 251 aggccgcggtggtgggggcgcgcgcgcgcgcgcgcagctggtgcggcg
 301 gcgcgggggtcagccgccgagccggcggcgacggaggagcagggcggcgt
 351 ggacgcgaacttccgatcggttggtcagagtgcgcgagttgggcttagcc
 401 aattaggtctcaacaatctattgggccgtaaaattcatgggccctggttt
 451 gtctaggcccaatatcccgttcatttcagcccacaaatatttccccagag
 501 gattattaaggcccacacgcagcttatagcagatcaagtacgatgtttcc
 551 tgatcgttggatcggaaacgtacggtcttgatcaggcatgccgacttcgt
 601 caaagagaggcggcatgacctgacgcggagttggttccgggcaccgtctg
 651 gatggtcgtaccgggaccggacacgtgtcgcgcctccaactacatggaca
 701 cgtgtggtgctgccattgggccgtacgcgtggcggtgaccgcaccggatg
 751 ctgcctcgcaccgccttgcccacgctttatatagagaggttttctctcca
 801 ttaatcgcatagcgagtcgaatcgaccgaaggggaggggagcgaagctt
 851 tgcgttctctaatcgcctcgtcaaggtaactaatcaatcacctcgtccta
 901 atcctcgaatctctcgtggtgcccgtctaatctcgcgattttgatgctcg
 951 tggtggaaagcgtaggaggatcccgtgcgagttagtctcaatctctcagg
1001 gtttcgtgcgatttagggtgatccacctcttaatcgagttacggtttcg
1051 tgcgattttagggtaatcctcttaatctctcattgatttagggtttcgtg
1101 agaatcgaggtagggatctgtgttatttatatcgatctaatagatggatt
1151 ggttttgagattgttctgtcagatggggattgtttcgatatattaccta
1201 atgatgtgtcagatggggattgtttcgatatattaccctaatgatgtgtc
1251 agatggggattgtttcgatatattaccctaatgatggataataagagtag
1301 ttcacagttatgttttgatcctgccacatagtttgagttttgtgatcaga
1351 tttagttttacttatttgtgcttagttcggatgggattgttctgatattg
1401 ttccaatagatgaatagctcgttaggttaaaatctttaggttgagttagg
1451 cgacacatagtttatttcctctggatttggattggaattgtgttcttagt
1501 ttttttcccctggatttggattggaattgtgtggagctgggttagagaat
1551 tacatctgtatcgtgtacacctacttgaactgtagagcttgggttctaag
1601 gtcaatttaatctgtattgtatctggctctttgcctagttgaactgtagt
1651 gctgatgttgtactgtgttttttacccgttttatttgctttactcgtgc
1701 aaatcaaatctgtcagatgctagaactaggtggctttattctgtgttctt
1751 acatagatctgttgtcctgtagttacttatgtcagttttgttattatctg
1801 aagatattttggttgttgcttgttgatgtggtgtgagctgtgagcagcg
1851 ctcttatgattaatgatgctgtccaattgtagtgtagtatgatgtgattg
1901 atatgttcatctatttgagctgacagtaccgatatcgtaggatctggtg
1951 ccaacttattctccagctgcttttttttacctatgttaattccaatcctt
2001 tcttgcctcttccagATGCAGATATTCGTTAAGACCCTCACTGGCAAGAC
   1              M  Q  I  F  V  K  T  L  T  G  K  T 2051 CATCACCTTGGAGGTTGAGTTCTCCGATACGATTGACAATGTGAAGGCTA
  13  I  T  L  E  V  E  F  S  D  T  I  D  N  V  K  A 2101 AGATTCAGGACAAGGAGGGCATCCCTCCGGACCAGCAACGCCTTATCTTC
  29  K  I  Q  D  K  E  G  I  P  P  D  Q  Q  R  L  I  F
```

FIG. 2A

```
2151 GCTGGCAAGCAGCTTGAGGATGGGCGTACTCTCGCGGATTATAACATCCA
  46  A  G  K  Q  L  E  D  G  R  T  L  A  D  Y  N  I  Q

2201 GAAGGAGTCCACCTTGCACCTTGTCCTCCGCCTTCGTGGAGGCATGCAAA
  63  K  E  S  T  L  H  L  V  L  R  L  R  G  G  M  Q

2251 TATTCGTGAAGACCCTCACCGGCAAGACCATTACCCTGGAGGTCGAGTCC
  79  I  F  V  K  T  L  T  G  K  T  I  T  L  E  V  E  S

2301 TCCGACACGATCGATAATGTGAAGGCCAAGATCCAGGACAAGGAGGGAAT
  96  S  D  T  I  D  N  V  K  A  K  I  Q  D  K  E  G  I

2351 CCCACCAGACCAGCAGCGTCTCATCTTTGCTGGGAAGCAGCTCGAGGATG
 113  P  P  D  Q  Q  R  L  I  F  A  G  K  Q  L  E  D

2401 GCCGCACCCTTGCAGACTACAACATCCAAAAGGAATCCACCCTGCACCTT
 129 G  R  T  L  A  D  Y  N  I  Q  K  E  S  T  L  H  L

2451 GTCCTGCGCCTCCGGGGCGGTATGCAGATCTTTGTGAAGACCCTTACTGG
 146  V  L  R  L  R  G  G  M  Q  I  F  V  K  T  L  T  G

2501 CAAGACGATCACCTTGGAGGTTGAGTCCTCTGACACGATCGACAATGTGA
 163  K  T  I  T  L  E  V  E  S  S  D  T  I  D  N  V

2551 AGGCCAAGATCCAGGACAAGGAGGGTATTCCACCAGACCAGCAGCGGCTC
 179 K  A  K  I  Q  D  K  E  G  I  P  P  D  Q  Q  R  L

2601 ATCTTCGCTGGCAAGCAGCTTGAGGACGGCCGCACCCTTGCTGACTATAA
 196  I  F  A  G  K  Q  L  E  D  G  R  T  L  A  D  Y  N

2651 CATCCAGAAGGAGTCCACCTTGCACTTGGTCCTCCGCCTTCGTGGAGGTA
 213  I  Q  K  E  S  T  L  H  L  V  L  R  L  R  G  G

2701 TGCAGATCTTCGTGAAGACCCTCACCGGCAAGACCATCACCCTGGAGGTT
 229 M  Q  I  F  V  K  T  L  T  G  K  T  I  T  L  E  V

2751 GAGTCGTCTGACACGATCGACAATGTGAAGGCCAAGATCCAGGACAAGGA
 246  E  S  S  D  T  I  D  N  V  K  A  K  I  Q  D  K  E

2801 GGGTATTCCACCAGACCAGCAGCGCCTCGTCTTCGCTGGCAAGCAGCTTG
 263   G  I  P  P  D  Q  Q  R  L  V  F  A  G  K  Q  L

2851 AGGATGGTCGCACCCTTGCAGATTACAACATCCAGAAGGAGTCCACCCTG
 279 E  D  G  R  T  L  A  D  Y  N  I  Q  K  E  S  T  L

2901 CACCTTGTCCTGCGCCTTCGTGGAGGTATGCAGATCTTCGTGAAGACCCT
 296  H  L  V  L  R  L  R  G  G  M  Q  I  F  V  K  T  L

2951 CACTGGCAAGACCATCACTCTGGAGGTTGAGTCCTCTGACACCATCGACA
 313   T  G  K  T  I  T  L  E  V  E  S  S  D  T  I  D

3001 ACGTGAAGGCCAAGATCCAGGATAAGGAGGGCATCCCTCCAGACCAGCAG
 329 N  V  K  A  K  I  Q  D  K  E  G  I  P  P  D  Q  Q

3051 CGCCTCATCTTCGCCGGCAAGCAGCTCGAGGATGGCCGCACCCTTGCCGA
 346  R  L  I  F  A  G  K  Q  L  E  D  G  R  T  L  A  D

3101 CTATAACATCCAGAAGGAGTCCACCCTGCACCTTGTCCTGCGCCTCCGTG
 363   Y  N  I  Q  K  E  S  T  L  H  L  V  L  R  L  R

3151 GTGGTCTCTGA (SEQ ID NO:8)
 379  G  G  L  *  (SEQ ID NO:9)
```

FIG. 2B

```
R1  ------------------------------------------------
R2  ------------------------------------------------
R3  GTAACTAATCAATCACCTCGTCCTAATCCTCGAATCTCTCGTGGTGCCCG  50
M   ------------------------------------------------

R1  ------------------------------------------------
R2  ------------------------------------------------
R3  TCTAATCTCGCGATTTTGATGCTCGTGGTGGAAAGCGTAGGAGGATCCCG 100
M   ------------------------------------------------

R1  ------------------------------------------------
R2  ------------------------GTACGCTGCTTCTCCTCTCCTCGCT  25
R3  TGCGAGTTAGTCTCAATCTCTCAGGGTTTCGTGCGATTTTAGGGTGATCC 150
M   ------------------------GTACGCCGCTCGTCCTCCCCCCCCC  25

R1  ---------------------------GTAT---GCGATTTTCTGAT   17
R2  TCGTTTCGATTCGATTTCGGACGGGTGAGGTTGT---TTTGTTGCTAGAT  72
R3  ACCTCTTAATCGAGTTACGGTTTCGTGCGATTTAGGGTAATCCTCTTAA 200
M   CCCCTCTCTACCTTCTCTAGATCGGCGTTCCGGT----CCATGGTTAGGG  71
                                *          *

R1  CCTCTCCGTTCCTCGCGTT--TGATTTGATT-TCCC-GGCCTGTTCGTGA  63
R2  CCGATTGGTGGTTAGGGTTGTCGATGTGATTATCGT-GAGATGTTTAGGG 121
R3  TCTCTCATTGATTTAGGGTTTCGTGAGAATCGAGGTAGGGATCTGTGTTA 250
M   CC---CGGTAGTTCTACTTCTGTTCATGTTTGTGTTAGATCCGTGTTTGT 118
       *     *       *       *    *      *       *

R1  TTGTGA-----GATGTTGTGGTTAGTCTCCGTTTTGCGATCTGT--GGTA 106
R2  GTTGTA-----GATCTGATGGTTGTGATTTGGGC-ACGGTTGGTTCGATA 165
R3  TTTATATC---GATCTAATAGATGG-ATTGGTTTTGAGATTGTTCTGTCA 296
M   GTTAGATCCGTGCTGCTAGCGTTCGTACACGGAT-GCGACCTGTACGTCA 167
         *   *  * *     ** *       *   *     *  *  *

R1  GATTTGAACAGGGT--TAG-ATGGGGTTCGCGTGGTATGCTGGATCT--G 151
R2  GGTGGAATCGTGGT--TAG-GTT---TTGGGATTGGATGTTGGTTCT--G 207
R3  GATGGGGATTGTTT--CGATATATTACCCTAATGATGTGTCAGATGG--G 342
M   GACACGTTCTGATTGCTAACTTGCCAGTGTTTCTCTTTGGGGAATCCTGG 217
        *           *      *           *   **    *    *

R1  --TGATTATGAGCGATG--CTGAACGT-GGTCCAAGTATTGATTGGTTCG 196
R2  A-TGATTGGGGGGAATT--TTTACGGTTAGATGAATTGTTGGATGATTCG 254
R3  GATTGTTTCGATATATTACCCTAATGATGTGTCAGATGGGGATTGTTTCG 392
M   GATGGCTCTAGCCGTTCCGCAGACGG--GATCGATTTCATGATTTTTTTT 265
        *       *        *      *  *    * *  *    **

R1  GA-------TCTAGAAGTAGA-AGTAGAACTGTGCTAGGGTTGTG-ATTT 237
R2  AT-------TGGGGAAATCGG-TGTAGATCTGTTGGGGAATTGTGGAACT 296
R3  ATATATTACCCTAATGATGGATAATAAGAGTAGTTCACAGTTATG-TTTT 441
M   GT------TTCGTTGCATAGG-GTTTGGTTTGCCCTTTTCCTTTATTTCA 308
              *  *          *        *         *   *
```

*FIG. 3A*

```
R1  GTTCCGATCT----GTTCAATCAGTAGGATTTAGTCTCTGTTTTTCTCGT  283
R2  AGTCATGCCT----GAGTGATTGGTGCGATTTGTAGCGTGTTCCATCTAG  342
R3  GATCCTGCCACATAGTTTGAGTTTTGTGATCAGATTTAGTTTTACTTATT  491
M   ATATATGCCG--TGCACTGTTTGTCGGGTCATCTTTTCATGCTTTTTT   356
              *             *  * *

R1  TGAGCCAAGT-------AGCAGCGTCAGGTATATT---------TTGCTT  358
R2  TAGGCCTTGTT---GCGAGCATGTTCAGATCTACTGTTCCGCTCTTGATT  389
R3  TGTGCTTAGTTCGGATGGGATTGTTCTGATATTGT-TCCAATAGATGAAT  540
M   TGT-CTTGGTTGTGAT-GATGTGGTCTGGTTGGGCGGTC-GTTCTAGATC  403
      *   *  **            *  * *             *

R1  AGGTTGTT-----TTTGATTCAGTCC---CTCTAGTTGCA-TAGATTCTA  383
R2  GAGTTATTGGTGCCATGGGTGGGTGCAAACACAGGCTGCAATATGTTATA  439
R3  AGCTCGTTAGGTTAAAATCTTTAGGTTGAGTTAGGCGACA-CATAGTTTA  589
M   GGAGTAGAA---TTCTGTTTCAAACTACCTGGTGGATTTATTAATTTTGG  450
             *                     *   *   *

R1  CTCTGTTCATGTTTAATCTA-------A-----GGGCTGCGTCTTGTTGA  396
R2  TCTGTTTTGTGTTTGATGTAGATCTGTA-----GGGTAGTTCTTCTTAGA  484
R3  TTTCCTCTGGATTTGGATTGGAATTGTGTTCTTAGTTTTTTTCCCCTGGA  639
M   ATCTGTATGTGTGTGCCATACATATTCA-----TAGTTACGAATTGAAGA  495
          *    * *     *                          **

R1  T-TAG--T--GATTACATAGCATAGCTGTCAGGATATTTTACTTGCTT-A  446
R2  CATGG--TTCAATTATGTAGC-TTGTCGTTTCGATTTGATGCTCATAT-G  530
R3  TTTGGATTGGAATTGTGTGGAGCTGG-GTTAGAGAATTACATCTGTATCG  688
M   TGATGGATGGAAATATCGATCTAGGATAGGTATACATGTTGAT-GCGGGT  544
         *   *  *       *         *           *

R1  TGCCTATCT-TATCAACTGTTGCACC-----TGTAAATTCTAGCCTATGT  484
R2  TTCACAGAT-TAGATAATGATGAACTC---TTTTAATTAATTGTCAATGG  576
R3  TGTACACCTACTTGAACTGTAGAGCTTGGGTTCTAAGGTCAATTTAATCT  738
M   TTTACTGATGCATATACAGAGATGCTT----TTTGTTCGCTTGGTTGTGA  590
         *         *  *  *   * *                  *

R1  TAATT--AACCTGCCTTATG--TGCT--CTCGGGATAG-TGCTAGTA-GT  526
R2  TAAAT--AGGAAGTCTTATCGCTATA--TCTGTCATAA-TGATCTCATGT  621
R3  GTATTGTATCTGGCTCTTTGCCTAGT--TGAACTGTAG-TGCTGATGTTG  785
M   TGATGTGGTGTGGTTGGGCGGTCGTTCATTCGTTCTAGATCGGAGTAGAA  640
         *         *                      **  *

R1  TATTG--------AATCAGTT-TGCCGA---------TGGAATTCTA--- 555
R2  TACTAT--CTGCCAGTAATTTATGCTAAG--------CACTATATTA--- 658
R3  TACTGTGTTTTTTACCCGTTTTATTTGCTTTACTCGTGCAAATCAA---  832
M   TACTGTTTCAAACTACCTGGTGTATTTAT--TAATTTTGGAACTGTATGT 688
    ** *            * *                               *
```

FIG. 3B

```
R1  GTAGTTCATA----GACCTGCAG-ATTAT--TTTTGTGAACTCGAGCACG   598
R2  GAATATCATGTTACAATCTGTAGTAATATCATGTTACAATCTGTAGTTCA   708
R3  ATCTGTCAGATGCTAGAACTAGGTGGCTTTATTCTGTGTTCTTACATAGA   882
M   GTGTGTCATAC----ATCTTCATAGTTACGAGTTTAAGATGGATGGAAAT   734
             ***                 *

R1  GTGCGT-CTCTCTATTTTGTTAGGTCA---CTGTTGGTGTTGATAGGTAC   644
R2  TCTATA-TAATCTATTGTGGTAATTTC---TTTTTACTATCTGTGTGAAG   754
R3  TCTGTTGTCCTGTAGTTACTTATGTCAGTTTTGTTATTATCTGAAGATAT   932
M   ATCGATCTAGGATAGGTATACATGTTGATGTGGGTTTTACTGATGCATAT   784
         * *        * *         * *          *

R1  ACT--GATGT--------TATTGTGGTTTAGATCGTGTATCTAAC-ATAT   683
R2  ATT--ATTGC--------CACTAGTTCATTCTACTTATTTCTGAA-GTTC   793
R3  TTTTGGTTGT--------TGCTTGTTGATGTGGTGTGAGCTGTGA-GCAG   973
M   ACATGATGGCATATGCAGCATCTATTCATATGCTCTAACCTTGAGTACCT   834
            *                    *          *

R1  TGGAATAAT--TTGAT-TGACTGATTTCTGCTGTACTTG--CTTGGTATT   728
R2  AGGATACGT--GTGCTGTTACTACCTATCTGAATACATG--TGTGATGTG   839
R3  CGCTCTTATGATTAATGATGCTGTCCAATTGTAGTGTAG--TATGATGTG  1021
M   ATCTATTATAATAAACAAGTATGTTTTATAATTATTTTGATCTTGATATA   884
         *         *              *    ** * *

R1  GTTATAAT-TT-CATGTTCAT--AGTTGCTGACCATGCTTCGGTA-ATTG   773
R2  CCTGTTAC-T---ATCTTTTT--GAATACATGT-ATGTTCTGTTGGAATA   882
R3  ATTGATATGTT-CATCTATTTTGAGCTGACAGTACCGATATCGTAGGATC  1070
M   CTTGGATGATGGCATATGCAGC-AGCTATATGTGGATTTTTTAGCCCTG   933
        *       *  ** *     *      *         *      *

R1  TGTGTGCAG-----------------------------------------  782
R2  TGTTTGCTGTTTGATCCGTTGTTGTGTCCTTAATCTTGTGCTAGTTCTTA   932
R3  TGGTGCCAACTTATTCTCCAGCTGCTTTTTTTACCTATGTTAATTCCAA  1120
M   CCTTCATACGCTATTTATTTGCTTGGTACTGTTTCTTTTGTCGATGCTCA   983

R1  ------------------------ (SEQ ID NO:14)
R2  CCCTATCTGTTTGGTGATTATTTCTTGCAG (SEQ ID NO:15)   962
R3  TCCTTTCTTGCCTCTTCCAG---------- (SEQ ID NO:3)   1140
M   CCCTGT-TGTTTGGTGTTACTTCTGCAG-- (SEQ ID NO:16)  1010
```

*FIG. 3C* pRESQ4
7307 bp pRESQ33
6192 bp pRESQ18
6405 bp pRESQ17
7942 bp

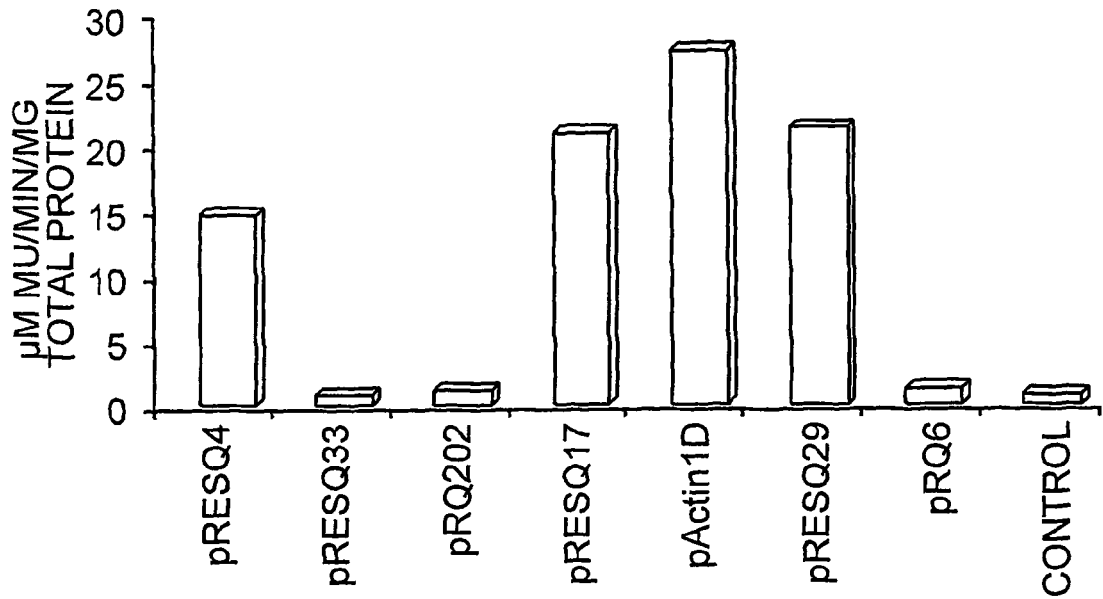

*FIG. 6* pRESQ42

```
RUB/3 INTRON                            GUS
⌇CTCTTCCAG│ATGCAGATA│ATGCAAATATTC⌇  (SEQ ID NO:21)
            M   Q   I   M   L   R   P    (SEQ ID NO:22)
``` pRESQ46

```
RUB/3 INTRON                            GUS
⌇CTCTTCCAG│ATACAGATA│ATGCAAATATTCG⌇ (SEQ ID NO:23)
                        M   L   R   P    (SEQ ID NO:24)
``` pRESQ47

```
RUB/3 INTRON                            GUS
⌇CTCTTCCAG│ATTCAGATA│ATGCAAATATTCG⌇ (SEQ ID NO:25)
                        M   L   R   P    (SEQ ID NO:24)
``` pRESQ48

```
RUB/3 INTRON                            GUS
⌇CTCTTCCAG│ATCCAGATA│ATGCAAATATTCG⌇ (SEQ ID NO:26)
                        M   L   R   P    (SEQ ID NO:24)
```

*FIG. 7*

SEQUENCE LISTING

<160> NUMBER OF SEQ ID NOS: 27

<210> SEQ ID NO 1
<211> LENGTH: 2015
<212> TYPE: DNA
<213> ORGANISM: Oryza sativa

<400> SEQUENCE: 1

```
ccacccaacc ccatatcgac agaggatgtg aagaacaggt aaatcacgca gaagaaccca      60
tctctgatag cagctatcga ttagaacaac gaatccatat tgggtccgtg ggaaatactt     120
actgcacagg aagggggggcg atctgacgag gccccgccac cggcctcgac ccgaggccga    180
ggccgacgaa gcgccggcga gtacggcgcc gcggcggcct ctgcccgtgc cctctgcgcg     240
tgggagggag aggccgcggt ggtgggggcg cgcgcgcgcg cgcgcgcagc tggtgcggcg     300 gcgcggggt cagccgccga gccggcggcg acggaggagc agggcggcgt ggacgcgaac      360
ttccgatcgg ttggtcagag tgcgcgagtt gggcttagcc aattaggtct caacaatcta     420
ttgggccgta aaattcatgg gccctggttt gtctaggccc aatatcccgt tcatttcagc     480
ccacaaatat ttccccagag gattattaag gcccacacg agcttatagc agatcaagta      540
cgatgtttcc tgatcgttgg atcggaaacg tacggtcttg atcaggcatg ccgacttcgt     600
caaagagagg cggcatgacc tgacgcggag ttggttccgg gcaccgtctg gatggtcgta     660
ccgggaccgg acacgtgtcg cgcctccaac tacatggaca cgtgtggtgc tgccattggg     720
ccgtacgcgt ggcggtgacc gcaccggatg ctgcctcgca ccgccttgcc cacgctttat     780
atagagaggt tttctctcca ttaatcgcat agcgagtcga atcgaccgaa ggggaggggg     840
agcgaagctt tgcgttctct aatcgcctcg tcaaggtaac taatcaatca cctcgtccta     900
atcctcgaat ctctcgtggt gcccgtctaa tctcgcgatt ttgatgctcg tggtggaaag     960
cgtaggagga tcccgtgcga gttagtctca atctctcagg gtttcgtgcg attttagggt    1020
gatccacctc ttaatcgagt tacggtttcg tgcgatttta gggtaatcct cttaatctct    1080
cattgattta gggtttcgtg agaatcgagg tagggatctg tgttatttat atcgatctaa    1140
tagatggatt ggtttttgaga ttgttctgtc agatggggat tgtttcgata tattaccccta  1200 atgatgtgtc agatggggat tgtttcgata tattaccccta atgatgtgtc agatggggat   1260
tgtttcgata tattacccta atgatggata ataagagtag ttcacagtta tgttttgatc    1320
ctgccacata gtttgagttt tgtgatcaga tttagtttta cttatttgtg cttagttcgg    1380
atgggattgt tctgatattg ttccaataga tgaatagctc gttaggttaa aatctttagg    1440
ttgagttagg cgacacatag tttatttcct ctggatttgg attggaattg tgttcttagt    1500
ttttttcccc tggatttgga ttggaattgt gtggagctgg gttagagaat tacatctgta    1560
tcgtgtacac ctacttgaac tgtagagctt gggttctaag gtcaatttaa tctgtattgt    1620
atctggctct ttgcctagtt gaactgtagt gctgatgttg tactgtgttt ttttacccgt    1680
tttatttgct ttactcgtgc aaatcaaatc tgtcagatgc tagaactagg tggctttatt    1740
ctgtgttctt acatagatct gttgtcctgt agttacttat gtcagttttg ttattatctg    1800
aagatatttt tggttgttgc ttgttgatgt ggtgtgagct gtgagcagcg ctcttatgat    1860
```

```
taatgatgct gtccaattgt agtgtagtat gatgtgattg atatgttcat ctattttgag    1920
ctgacagtac cgatatcgta ggatctggtg ccaacttatt ctccagctgc ttttttttac    1980
ctatgttaat tccaatcctt tcttgcctct tccag                               2015

<210> SEQ ID NO 2
<211> LENGTH: 875
<212> TYPE: DNA
<213> ORGANISM: Oryza sativa

<400> SEQUENCE: 2
ccacccaacc ccatatcgac agaggatgtg aagaacaggt aaatcacgca gaagaaccca      60
tctctgatag cagctatcga ttagaacaac gaatccatat tgggtccgtg ggaaatactt     120
actgcacagg aaggggggcg atctgacgag gccccgccac cggcctcgac ccgaggccga     180
ggccgacgaa gcgccggcga gtacggcgcc gcggcggcct ctgcccgtgc cctctgcgcg     240
tgggagggag aggccgcggt ggtggggggcg cgcgcgcgcg cgcgcgcagc tggtgcggcg     300 gcgcggggt cagccgccga gccggcggcg acggaggagc agggcggcgt ggacgcgaac      360
ttccgatcgg ttggtcagag tgcgcgagtt gggcttagcc aattaggtct caacaatcta     420
ttgggccgta aaattcatgg gccctggttt gtctaggccc aatatcccgt tcatttcagc     480
ccacaaatat ttccccagag gattattaag gcccacacgc agcttatagc agatcaagta     540
cgatgtttcc tgatcgttgg atcggaaacg tacggtcttg atcaggcatg ccgacttcgt     600
caaagagagg cggcatgacc tgacgcgag ttggttccgg gcaccgtctg gatggtcgta      660
ccgggaccgg acacgtgtcg cgcctccaac tacatggaca cgtgtggtgc tgccattggg     720
ccgtacgcgt ggcggtgacc gcaccggatg ctgcctcgca ccgccttgcc cacgctttat     780
atagagaggt tttctctcca ttaatcgcat agcgagtcga atcgaccgaa ggggagggg      840 agcgaagctt tgcgttctct aatcgcctcg tcaag                               875

<210> SEQ ID NO 3
<211> LENGTH: 1140
<212> TYPE: DNA
<213> ORGANISM: Oryza sativa

<400> SEQUENCE: 3
gtaactaatc aatcacctcg tcctaatcct cgaatctctc gtggtgcccg tctaatctcg      60
cgattttgat gctcgtggtg gaaagcgtag gaggatcccg tgcgagttag tctcaatctc     120
tcagggtttc gtgcgatttt agggtgatcc acctcttaat cgagttacgg tttcgtgcga     180
ttttagggta atcctcttaa tctctcattg atttagggtt tcgtgagaat cgaggtaggg     240
atctgtgtta tttatatcga tctaatagat ggattggttt tgagattgtt ctgtcagatg     300
gggattgttt cgatatatta ccctaatgat gtgtcagatg gggattgttt cgatatatta     360
ccctaatgat gtgtcagatg gggattgttt cgatatatta ccctaatgat ggataataag     420
agtagttcac agttatgttt tgatcctgcc acatagtttg agttttgtga tcagatttag     480
ttttacttat ttgtgcttag ttcggatggg attgttctga tattgttcca atagatgaat     540
agctcgttag gttaaaatct ttaggttgag ttaggcgaca catagtttat ttcctctgga     600
tttggattgg aattgtgttc ttagtttttt tcccctggat ttggattgga attgtgtgga     660
gctgggttag agaattacat ctgtatcgtg tacacctact tgaactgtag agcttgggtt     720
ctaaggtcaa tttaatctgt attgtatctg gctctttgcc tagttgaact gtagtgctga     780
tgttgtactg tgttttttta cccgttttat ttgcttact cgtgcaaatc aaatctgtca      840
```

```
gatgctagaa ctaggtggct ttattctgtg ttcttacata gatctgttgt cctgtagtta      900
cttatgtcag ttttgttatt atctgaagat attttggtt gttgcttgtt gatgtggtgt       960
gagctgtgag cagcgctctt atgattaatg atgctgtcca attgtagtgt agtatgatgt     1020
gattgatatg ttcatctatt ttgagctgac agtaccgata tcgtaggatc tggtgccaac     1080
ttattctcca gctgcttttt tttacctatg ttaattccaa tcctttcttg cctcttccag     1140
```

<210> SEQ ID NO 4
<211> LENGTH: 30
<212> TYPE: DNA
<213> ORGANISM: Artificial Sequence
<220> FEATURE:
<223> OTHER INFORMATION: Synthetic oligonucleotide primer

<400> SEQUENCE: 4
gtcgaccacc caaccccata tcgacagagg         30

<210> SEQ ID NO 5
<211> LENGTH: 37
<212> TYPE: DNA
<213> ORGANISM: Artificial Sequence
<220> FEATURE:
<223> OTHER INFORMATION: Synthetic oligonucleotide primer

<400> SEQUENCE: 5
cccgggctgg aagaggcaag aaaggattgg aattaac         37

<210> SEQ ID NO 6
<211> LENGTH: 26
<212> TYPE: DNA
<213> ORGANISM: Artificial Sequence
<220> FEATURE:
<223> OTHER INFORMATION: Synthetic oligonucleotide primer

<400> SEQUENCE: 6
cccgggtaac taatcaatca cctcgt         26

<210> SEQ ID NO 7
<211> LENGTH: 24
<212> TYPE: DNA
<213> ORGANISM: Artificial Sequence
<220> FEATURE:
<223> OTHER INFORMATION: Synthetic oligonucleotide primer

<400> SEQUENCE: 7
cttgacgagg cgattagaga acgc         24

<210> SEQ ID NO 8
<211> LENGTH: 3161
<212> TYPE: DNA
<213> ORGANISM: Oryza sativa

<400> SEQUENCE: 8

```
acacccaacc ccatatcgac agaggatgtg aagaacaggt aaatcacgca gaagaaccca       60
tctctgatag cagctatcga ttagaacaac gaatccatat tgggtccgtg ggaaatactt      120
actgcacagg aaggggggcg atctgacgag gccccgccac cggcctcgac ccgaggccga      180
ggccgacgaa gcgccggcga gtacggcgcc gggcggcct ctgcccgtgc cctctgcgcg      240
tgggagggag aggccgcggt ggtgggggcg cgcgcgcgcg cgcgcgcagc tggtgcggcg      300 gcgcggggt cagccgccga gccggcggcg acggaggagc agggcggcgt ggacgcgaac      360
ttccgatcgg ttggtcagag tgcgcgagtt gggcttagcc aattaggtct caacaatcta      420
```

```
ttgggccgta aaattcatgg gccctggttt gtctaggccc aatatcccgt tcatttcagc    480
ccacaaatat ttccccagag gattattaag gcccacacgc agcttatagc agatcaagta    540
cgatgtttcc tgatcgttgg atcggaaacg tacggtcttg atcaggcatg ccgacttcgt    600
caaagagagg cggcatgacc tgacgcgag ttggttccgg gcaccgtctg gatggtcgta    660
ccgggaccgg acacgtgtcg cgcctccaac tacatggaca cgtgtggtgc tgccattggg    720
ccgtacgcgt ggcggtgacc gcaccggatg ctgcctcgca ccgccttgcc cacgctttat    780
atagagaggt tttctctcca ttaatcgcat agcgagtcga atcgaccgaa ggggaggggg    840
agcgaagctt tgcgttctct aatcgcctcg tcaaggtaac taatcaatca cctcgtccta    900
atcctcgaat ctctcgtggt gcccgtctaa tctcgcgatt ttgatgctcg tggtggaaag    960
cgtaggagga tcccgtgcga gttagtctca atctctcagg gtttcgtgcg attttagggt   1020
gatccacctc ttaatcgagt tacggtttcg tgcgatttta gggtaatcct cttaatctct   1080
cattgattta gggtttcgtg agaatcgagg tagggatctg tgttatttat atcgatctaa   1140
tagatggatt ggttttgaga ttgttctgtc agatggggat tgtttcgata tattacccta   1200
atgatgtgtc agatggggat tgtttcgata tattacccta atgatgtgtc agatggggat   1260
tgtttcgata tattacccta atgatggata ataagagtag ttcacagtta tgttttgatc   1320
ctgccacata gtttgagttt tgtgatcaga tttagtttta cttatttgtg cttagttcgg   1380
atgggattgt tctgatattg ttccaataga tgaatagctc gttaggttaa aatctttagg   1440
ttgagttagg cgacacatag tttatttcct ctggatttgg attggaattg tgttcttagt   1500
ttttttcccc tggatttgga ttggaattgt gtggagctgg gttagagaat tacatctgta   1560
tcgtgtacac ctacttgaac tgtagagctt gggttctaag gtcaatttaa tctgtattgt   1620
atctggctct ttgcctagtt gaactgtagt gctgatgttg tactgtgttt ttttacccgt   1680
tttatttgct ttactcgtgc aaatcaaatc tgtcagatgc tagaactagg tggctttatt   1740
ctgtgttctt acatagatct gttgtcctgt agttacttat gtcagttttg ttattatctg   1800
aagatatttt tggttgttgc ttgttgatgt ggtgtgagct gtgagcagcg ctcttatgat   1860
taatgatgct gtccaattgt agtgtagtat gatgtgattg atatgttcat ctattttgag   1920
ctgacagtac cgatatcgta ggatctggtg ccaacttatt ctccagctgc tttttttac   1980 ctatgttaat tccaatcctt tcttgcctct tccagatgca gatattcgtt aagaccctca   2040
ctggcaagac catcaccttg gaggttgagt tctccgatac gattgacaat gtgaaggcta   2100
agattcagga caaggagggc atccctccgg accagcaacg ccttatcttc gctggcaagc   2160
agcttgagga tgggcgtact ctcgcggatt ataacatcca gaaggagtcc accttgcacc   2220
ttgtcctccg ccttcgtgga ggcatgcaaa tattcgtgaa gaccctcacc ggcaagacca   2280
ttaccctgga ggtcgagtcc tccgacacga tcgataatgt gaaggccaag atccaggaca   2340
aggagggaat cccaccagac cagcagcgtc tcatctttgc tgggaagcag ctcgaggatg   2400
gccgcaccct tgcagactac aacatccaaa aggaatccac cctgcacctt gtcctgcgcc   2460
tccggggcgg tatgcagatc tttgtgaaga cccttactgg caagacgatc accttggagg   2520
ttgagtcctc tgacacgatc gacaatgtga aggccaagat ccaggacaag gagggtattc   2580
caccagacca gcagcggctc atcttcgctg gcaagcagct tgaggacggc cgcacccttg   2640
ctgactataa catccagaag gagtccacct tgcacttggt cctccgcctt cgtggaggta   2700
tgcagatctt cgtgaagacc ctcaccggca agaccatcac cctggaggtt gagtcgtctg   2760
acacgatcga caatgtgaag gccaagatcc aggacaagga gggtattcca ccagaccagc   2820
```

```
agcgcctcgt cttcgctggc aagcagcttg aggatggtcg caccettgca gattacaaca     2880 tccagaagga gtccaccctg caccttgtcc tgcgccttcg tggaggtatg cagatcttcg     2940
tgaagaccct cactggcaag accatcactc tggaggttga gtcctctgac accatcgaca     3000
acgtgaaggc caagatccag gataaggagg gcatccctcc agaccagcag cgcctcatct     3060
tcgccggcaa gcagctcgag gatggccgca cccttgccga ctataacatc cagaaggagt     3120
ccaccctgca ccttgtcctg cgcctccgtg gtggtctctg a                         3161
```

<210> SEQ ID NO 9
<211> LENGTH: 381
<212> TYPE: PRT
<213> ORGANISM: Oryza sativa

<400> SEQUENCE: 9

```
Met Gln Ile Phe Val Lys Thr Leu Thr Gly Lys Thr Ile Thr Leu Glu
1               5                   10                  15

Val Glu Phe Ser Asp Thr Ile Asp Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ala Asp Tyr Asn Ile Gln Lys Glu
    50                  55                  60

Ser Thr Leu His Leu Val Leu Arg Leu Arg Gly Met Gln Ile Phe
65                  70                  75                  80

Val Lys Thr Leu Thr Gly Lys Thr Ile Thr Leu Glu Val Glu Ser Ser
                85                  90                  95

Asp Thr Ile Asp Asn Val Lys Ala Lys Ile Gln Asp Lys Glu Gly Ile
            100                 105                 110

Pro Pro Asp Gln Gln Arg Leu Ile Phe Ala Gly Lys Gln Leu Glu Asp
        115                 120                 125

Gly Arg Thr Leu Ala Asp Tyr Asn Ile Gln Lys Glu Ser Thr Leu His
    130                 135                 140

Leu Val Leu Arg Leu Arg Gly Gly Met Gln Ile Phe Val Lys Thr Leu
145                 150                 155                 160

Thr Gly Lys Thr Ile Thr Leu Glu Val Glu Ser Ser Asp Thr Ile Asp
                165                 170                 175

Asn Val Lys Ala Lys Ile Gln Asp Lys Glu Gly Ile Pro Pro Asp Gln
            180                 185                 190

Gln Arg Leu Ile Phe Ala Gly Lys Gln Leu Glu Asp Gly Arg Thr Leu
        195                 200                 205

Ala Asp Tyr Asn Ile Gln Lys Glu Ser Thr Leu His Leu Val Leu Arg
    210                 215                 220

Leu Arg Gly Gly Met Gln Ile Phe Val Lys Thr Leu Thr Gly Lys Thr
225                 230                 235                 240

Ile Thr Leu Glu Val Glu Ser Ser Asp Thr Ile Asp Asn Val Lys Ala
                245                 250                 255

Lys Ile Gln Asp Lys Glu Gly Ile Pro Pro Asp Gln Gln Arg Leu Val
            260                 265                 270

Phe Ala Gly Lys Gln Leu Glu Asp Gly Arg Thr Leu Ala Asp Tyr Asn
        275                 280                 285

Ile Gln Lys Glu Ser Thr Leu His Leu Val Leu Arg Leu Arg Gly Gly
    290                 295                 300

Met Gln Ile Phe Val Lys Thr Leu Thr Gly Lys Thr Ile Thr Leu Glu
305                 310                 315                 320
```

```
Val Glu Ser Ser Asp Thr Ile Asp Asn Val Lys Ala Lys Ile Gln Asp
                325                 330                 335

Lys Glu Gly Ile Pro Pro Asp Gln Gln Arg Leu Ile Phe Ala Gly Lys
            340                 345                 350

Gln Leu Glu Asp Gly Arg Thr Leu Ala Asp Tyr Asn Ile Gln Lys Glu
        355                 360                 365

Ser Thr Leu His Leu Val Leu Arg Leu Arg Gly Gly Leu
    370                 375                 380

<210> SEQ ID NO 10
<211> LENGTH: 15
<212> TYPE: DNA
<213> ORGANISM: Drosophila sp.
<220> FEATURE:
<221> NAME/KEY: misc_feature
<222> LOCATION: (8)..(8)
<223> OTHER INFORMATION: "n" represents A, T, C or G.

<400> SEQUENCE: 10
ctggaatntt ctaga                                                        15

<210> SEQ ID NO 11
<211> LENGTH: 11
<212> TYPE: DNA
<213> ORGANISM: Artificial Sequence
<220> FEATURE:
<223> OTHER INFORMATION: Enhancer consensus sequence

<400> SEQUENCE: 11
ggtgtggwww g                                                            11

<210> SEQ ID NO 12
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 12
cgaatcgacc gaaggggagg                                                   20

<210> SEQ ID NO 13
<211> LENGTH: 23
<212> TYPE: DNA
<213> ORGANISM: Artificial Sequence
<220> FEATURE:
<223> OTHER INFORMATION: Synthetic oligonucleotide primer

<400> SEQUENCE: 13
acacgatgat atgacagacg agc                                               23

<210> SEQ ID NO 14
<211> LENGTH: 782
<212> TYPE: DNA
<213> ORGANISM: Oryza sativa

<400> SEQUENCE: 14
gtatgcgatt ttctgatcct ctccgttcct cgcgtttgat ttgatttccc ggcctgttcg       60
tgattgtgag atgttgtggt tagtctccgt tttgcgatct gtggtagatt tgaacagggt      120
tagatggggt tcgcgtggta tgctggatct gtgattatga gcgatgctga acgtggtcca      180
agtattgatt ggttcggatc tagaagtaga agtagaactg tgctagggtt gtgatttgtt      240
ccgatctgtt caatcagtag gatttagtct ctgtttttct cgttgagcca agtagcagcg      300
```

```
tcaggtatat tttgcttagg ttgttttga ttcagtccct ctagttgcat agattctact    360
ctgttcatgt ttaatctaag ggctgcgtct tgttgattag tgattacata gcatagctgt    420
caggatattt tacttgctta tgcctatctt atcaactgtt gcacctgtaa attctagcct    480
atgttaatta acctgcctta tgtgctctcg ggatagtgct agtagttatt gaatcagttt    540
gccgatggaa ttctagtagt tcatagacct gcagattatt tttgtgaact cgagcacggt    600
gcgtctctct attttgttag gtcactgttg gtgttgatag gtacactgat gttattgtgg    660
tttagatcgt gtatctaaca tattggaata atttgattga ctgatttctg ctgtacttgc    720
ttggtattgt tataatttca tgttcatagt tgctgaccat gcttcggtaa ttgtgtgtgc    780
ag                                                                    782

<210> SEQ ID NO 15
<211> LENGTH: 962
<212> TYPE: DNA
<213> ORGANISM: Oryza sativa

<400> SEQUENCE: 15
gtacgctgct tctcctctcc tcgcttcgtt tcgattcgat ttcggacggg tgaggttgtt     60
ttgttgctag atccgattgg tggttagggt tgtcgatgtg attatcgtga gatgtttagg    120
ggttgtagat ctgatggttg tgatttgggc acggttggtt cgataggtgg aatcgtggtt    180
aggttttggg attggatgtt ggttctgatg attggggga attttttacgg ttagatgaat    240 tgttggatga ttcgattggg gaaatcggtg tagatctgtt ggggaattgt ggaactagtc    300
atgcctgagt gattggtgcg atttgtagcg tgttccatct agtaggcctt gttgcgagca    360
tgttcagatc tactgttccg ctcttgattg agttattggt gccatgggtg ggtgcaaaca    420
caggctgcaa tatgttatat ctgttttgtg tttgatgtag atctgtaggg tagttcttct    480
tagacatggt tcaattatgt agcttgtcgt ttcgatttga tgctcatatg ttcacagatt    540
agataatgat gaactctttt aattaattgt caatggtaaa taggaagtct tatcgctata    600
tctgtcataa tgatctcatg ttactatctg ccagtaattt atgctaagca ctatattaga    660
atatcatgtt acaatctgta gtaatatcat gttacaatct gtagttcatc tatataatct    720
attgtggtaa tttctttta ctatctgtgt gaagattatt gccactagtt cattctactt    780
atttctgaag ttcaggatac gtgtgctgtt actacctatc tgaatacatg tgtgatgtgc    840
ctgttactat ctttttgaat acatgtatgt tctgttggaa tatgtttgct gtttgatccg    900
ttgttgtgtc cttaatcttg tgctagttct taccctatct gtttggtgat tatttcttgc    960
ag                                                                    962

<210> SEQ ID NO 16
<211> LENGTH: 1010
<212> TYPE: DNA
<213> ORGANISM: Zea mays

<400> SEQUENCE: 16
gtacgccgct cgtcctcccc ccccccccct ctctaccttc tctagatcgg cgttccggtc     60
catggttagg gcccggtagt tctacttctg ttcatgtttg tgttagatcc gtgtttgtgt    120
tagatccgtg ctgctagcgt tcgtacacgg atgcgacctg tacgtcagac acgttctgat    180
tgctaacttg ccagtgtttc tctttgggga atcctgggat ggctctagcc gttccgcaga    240
cgggatcgat ttcatgattt ttttgtttc gttgcatagg gtttggtttg cccttttcct    300
ttatttcaat atatgccgtg cacttgtttg tcgggtcatc ttttcatgct ttttttgtc     360
```

```
ttggttgtga tgatgtggtc tggttgggcg gtcgttctag atcggagtag aattctgttt      420
caaactacct ggtggattta ttaattttgg atctgtatgt gtgtgccata catattcata      480
gttacgaatt gaagatgatg gatggaaata tcgatctagg ataggtatac atgttgatgc      540
gggttttact gatgcatata cagagatgct ttttgttcgc ttggttgtga tgatgtggtg      600
tggttgggcg gtcgttcatt cgttctagat cggagtagaa tactgtttca aactacctgg      660
tgtatttatt aattttggaa ctgtatgtgt gtgtcataca tcttcatagt tacgagttta      720
agatggatgg aaatatcgat ctaggatagg tatacatgtt gatgtgggtt ttactgatgc      780
atatacatga tggcatatgc agcatctatt catatgctct aaccttgagt acctatctat      840
tataataaac aagtatgttt tataattatt ttgatcttga tatacttgga tgatggcata      900
tgcagcagct atatgtggat ttttttagcc ctgccttcat acgctattta tttgcttggt      960
actgtttctt ttgtcgatgc tcaccctgtt gtttggtgtt acttctgcag                1010

<210> SEQ ID NO 17
<211> LENGTH: 2024
<212> TYPE: DNA
<213> ORGANISM: Oryza sativa

<400> SEQUENCE: 17
ccacccaacc ccatatcgac agaggatgtg aagaacaggt aaatcacgca gaagaaccca       60
tctctgatag cagctatcga ttagaacaac gaatccatat tgggtccgtg ggaaatactt      120
actgcacagg aaggggggcg atctgacgag gccccgccac cggcctcgac ccgaggccga      180
ggccgacgaa gcgccggcga gtacggcgcc gcggcggcct ctgcccgtgc cctctgcgcg      240
tgggagggag aggccgcggt ggtggggggcg cgcgcgcgcg cgcgcgcagc tggtgcggcg      300 gcgcggggt cagccgccga gccggcggcg acggaggagc agggcggcgt ggacgcgaac      360
ttccgatcgg ttggtcagag tgcgcgagtt gggcttagcc aattaggtct caacaatcta      420
ttgggccgta aaattcatgg gccctggttt gtctaggccc aatatcccgt tcatttcagc      480
ccacaaatat ttccccagag gattattaag gcccacacgc agcttatagc agatcaagta      540
cgatgtttcc tgatcgttgg atcggaaacg tacggtcttg atcaggcatg ccgacttcgt      600
caaagagagg cggcatgacc tgacgcggag ttggttccgg gcaccgtctg gatggtcgta      660
ccgggaccgg acacgtgtcg cgcctccaac tacatggaca cgtgtggtgc tgccattggg      720
ccgtacgcgt ggcggtgacc gcaccggatg ctgcctcgca ccgccttgcc cacgctttat      780 ataagaggt tttctctcca ttaatcgcat agcgagtcga atcgaccgaa ggggaggggg      840
agcgaagctt tgcgttctct aatcgcctcg tcaaggtaac taatcaatca cctcgtccta      900
atcctcgaat ctctcgtggt gcccgtctaa tctcgcgatt ttgatgctcg tggtggaaag      960
cgtaggagga tcccgtgcga gttagtctca atctctcagg gtttcgtgcg attttagggt     1020
gatccacctc ttaatcgagt tacggtttcg tgcgatttta gggtaatcct cttaatctct     1080
cattgattta gggtttcgtg agaatcgagg tagggatctg tgttatttat atcgatctaa     1140
tagatggatt ggttttgaga ttgttctgtc agatgggat tgtttcgata tattacccta     1200
atgatgtgtc agatggggat tgtttcgata tattacccta atgatgtgtc agatggggat     1260
tgtttcgata tattacccta atgatggata ataagagtag ttcacagtta tgttttgatc     1320
ctgccacata gtttgagttt tgtgatcaga tttagttta cttatttgtg cttagttcgg     1380
atgggattgt tctgatattg ttccaataga tgaatagctc gttaggttaa aatctttagg     1440
ttgagttagg cgacacatag tttatttcct ctggatttgg attggaattg tgttcttagt     1500
```

```
tttttttcccc tggatttgga ttggaattgt gtggagctgg gttagagaat tacatctgta    1560
tcgtgtacac ctacttgaac tgtagagctt gggttctaag gtcaatttaa tctgtattgt    1620
atctggctct ttgcctagtt gaactgtagt gctgatgttg tactgtgttt ttttacccgt    1680
tttatttgct ttactcgtgc aaatcaaatc tgtcagatgc tagaactagg tggctttatt    1740
ctgtgttctt acatagatct gttgtcctgt agttacttat gtcagttttg ttattatctg    1800
aagatatttt tggttgttgc ttgttgatgt ggtgtgagct gtgagcagcg ctcttatgat    1860
taatgatgct gtccaattgt agtgtagtat gatgtgattg atatgttcat ctattttgag    1920
ctgacagtac cgatatcgta ggatctggtg ccaacttatt ctccagctgc ttttttttac    1980
ctatgttaat ccaatccttt tcttgcctct tccagatgca gata                     2024

<210> SEQ ID NO 18
<211> LENGTH: 2024
<212> TYPE: DNA
<213> ORGANISM: Oryza sativa

<400> SEQUENCE: 18
ccacccaacc ccatatcgac agaggatgtg aagaacaggt aaatcacgca gaagaaccca      60
tctctgatag cagctatcga ttagaacaac gaatccatat tgggtccgtg ggaaatactt     120
actgcacagg aagggggggcg atctgacgag gccccgccac cggcctcgac ccgaggccga    180
ggccgacgaa gcgccggcga gtacggcgcc gcggcggcct ctgcccgtgc cctctgcgcg    240
tgggagggag aggccgcggt ggtgggggcg cgcgcgcgcg cgcgcgcagc tggtgcggcg    300
gcgcgggggt cagccgccga gccggcggcg acggaggagc agggcggcgt ggacgcgaac    360
ttccgatcgg ttggtcagag tgcgcgagtt gggcttagcc aattaggtct caacaatcta    420
ttgggccgta aaattcatgg gccctggttt gtctaggccc aatatcccgt tcatttcagc    480
ccacaaatat ttccccagag gattattaag gcccacacgc agcttatagc agatcaagta    540
cgatgtttcc tgatcgttgg atcggaaacg tacggtcttg atcaggcatg ccgacttcgt    600
caaagagagg cggcatgacc tgacgcggag ttggttccgg gcaccgtctg gatggtcgta    660
ccgggaccgg acacgtgtcg cgcctccaac tacatggaca cgtgtggtgc tgccattggg    720
ccgtacgcgt ggcggtgacc gcaccggatg ctgcctcgca ccgccttgcc cacgctttat    780
atagagaggt tttctctcca ttaatcgcat agcgagtcga atcgaccgaa ggggaggggg    840
agcgaagctt tgcgttctct aatcgcctcg tcaaggtaac taatcaatca cctcgtccta    900
atcctcgaat ctctcgtggt gcccgtctaa tctcgcgatt ttgatgctcg tggtggaaag    960
cgtaggagga tcccgtgcga gttagtctca atctctcagg gtttcgtgcg attttagggt   1020
gatccacctc ttaatcgagt tacggttccg tgcgatttta gggtaatcct cttaatctct   1080
cattgattta gggtttcgtg agaatcgagg tagggatctg tgttatttat atcgatctaa   1140
tagatggatt ggttttgaga ttgttctgtc agatggggat tgtttcgata tattacccta   1200
atgatgtgtc agatggggat tgtttcgata tattacccta atgatgtgtc agatggggat   1260
tgtttcgata tattacccta atgatggata ataagagtag ttcacagtta tgttttgatc   1320
ctgccacata gtttgagttt tgtgatcaga tttagtttta cttatttgtg cttagttcgg   1380
atgggattgt tctgatattg ttccaataga tgaatagctc gttaggttaa aatctttagg   1440
ttgagttagg cgacacatag tttatttcct ctggatttgg attggaattg tgttcttagt   1500
ttttttcccc tggatttgga ttggaattgt gtggagctgg gttagagaat tacatctgta   1560
tcgtgtacac ctacttgaac tgtagagctt gggttctaag gtcaatttaa tctgtattgt   1620
```

-continued

| | |
|---|---|
| atctggctct tgcctagtt gaactgtagt gctgatgttg tactgtgttt ttttacccgt | 1680 |
| tttatttgct ttactcgtgc aaatcaaatc tgtcagatgc tagaactagg tggctttatt | 1740 |
| ctgtgttctt acatagatct gttgtcctgt agttacttat gtcagttttg ttattatctg | 1800 |
| aagatatttt tggttgttgc ttgttgatgt ggtgtgagct gtgagcagcg ctcttatgat | 1860 |
| taatgatgct gtccaattgt agtgtagtat gatgtgattg atatgttcat ctattttgag | 1920 |
| ctgacagtac cgatatcgta ggatctggtg ccaacttatt ctccagctgc ttttttttac | 1980 |
| ctatgttaat tccaatcctt tcttgcctct tccagataca gata | 2024 |

<210> SEQ ID NO 19
<211> LENGTH: 2024
<212> TYPE: DNA
<213> ORGANISM: Oryza sativa

<400> SEQUENCE: 19

| | |
|---|---|
| ccacccaacc ccatatcgac agaggatgtg aagaacaggt aaatcacgca gaagaaccca | 60 |
| tctctgatag cagctatcga ttagaacaac gaatccatat tgggtccgtg ggaaatactt | 120 |
| actgcacagg aagggggggcg atctgacgag gccccgccac cggcctcgac ccgaggccga | 180 |
| ggccgacgaa gcgccggcga gtacggcgcc gcggcggcct ctgcccgtgc cctctgcgcg | 240 |
| tgggagggag aggccgcggt ggtggggggcg cgcgcgcgcg cgcgcgcagc tggtgcggcg | 300 |
| gcgcggggggt cagccgccga gccggcggcg acggaggagc agggcggcgt ggacgcgaac | 360 |
| ttccgatcgg ttggtcagag tgcgcgagtt gggcttagcc aattaggtct caacaatcta | 420 |
| ttgggccgta aaattcatgg gccctggttt gtctaggccc aatatcccgt tcatttcagc | 480 |
| ccacaaatat ttccccagag gattattaag gcccacacgc agcttatagc agatcaagta | 540 |
| cgatgtttcc tgatcgttgg atcggaaacg tacggtcttg atcaggcatg ccgacttcgt | 600 |
| caaagagagg cggcatgacc tgacgcgag ttggttccgg gcaccgtctg gatggtcgta | 660 |
| ccgggaccgg acacgtgtcg cgcctccaac tacatggaca cgtgtggtgc tgccattggg | 720 |
| ccgtacgcgt ggcggtgacc gcaccggatg ctgcctcgca ccgccttgcc cacgctttat | 780 |
| atagagaggt tttctctcca ttaatcgcat agcgagtcga atcgaccgaa ggggaggggg | 840 |
| agcgaagctt tgcgttctct aatcgcctcg tcaaggtaac taatcaatca cctcgtccta | 900 |
| atcctcgaat ctctcgtggt gcccgtctaa tctcgcgatt ttgatgctcg tggtggaaag | 960 |
| cgtaggagga tcccgtgcga gttagtctca atctctcagg gtttcgtgcg attttagggt | 1020 |
| gatccacctc ttaatcgagt tacggttttcg tgcgattttta gggtaatcct cttaatctct | 1080 |
| cattgattta gggtttcgtg agaatcgagg tagggatctg tgttatttat atcgatctaa | 1140 |
| tagatggatt ggttttgaga ttgttctgtc agatggggat tgtttcgata tattacccta | 1200 |
| atgatgtgtc agatggggat tgtttcgata tattacccta atgatgtgtc agatggggat | 1260 |
| tgtttcgata tattacccta atgatggata ataagagtag ttcacagtta tgttttgatc | 1320 |
| ctgccacata gtttgagttt tgtgatcaga tttagtttta cttatttgtg cttagttcgg | 1380 |
| atgggattgt tctgatattg ttccaataga tgaatagctc gttaggttaa aatctttagg | 1440 |
| ttgagttagg cgacacatag tttatttcct ctggatttgg attggaattg tgttcttagt | 1500 |
| ttttttcccc tggatttgga ttggaattgt gtggagctgg gttagagaat tacatctgta | 1560 |
| tcgtgtacac ctacttgaac tgtagagctt gggttctaag gtcaatttaa tctgtattgt | 1620 |
| atctggctct tgcctagtt gaactgtagt gctgatgttg tactgtgttt ttttacccgt | 1680 |
| tttatttgct ttactcgtgc aaatcaaatc tgtcagatgc tagaactagg tggctttatt | 1740 |

| | |
|---|---|
| ctgtgttctt acatagatct gttgtcctgt agttacttat gtcagttttg ttattatctg | 1800 |
| aagatatttt tggttgttgc ttgttgatgt ggtgtgagct gtgagcagcg ctcttatgat | 1860 |
| taatgatgct gtccaattgt agtgtagtat gatgtgattg atatgttcat ctattttgag | 1920 |
| ctgacagtac cgatatcgta ggatctggtg ccaacttatt ctccagctgc ttttttttac | 1980 |
| ctatgttaat tccaatcctt tcttgcctct tccagattca gata | 2024 |

<210> SEQ ID NO 20
<211> LENGTH: 2024
<212> TYPE: DNA
<213> ORGANISM: Oryza sativa

<400> SEQUENCE: 20

| | |
|---|---|
| ccacccaacc ccatatcgac agaggatgtg aagaacaggt aaatcacgca gaagaaccca | 60 |
| tctctgatag cagctatcga ttagaacaac gaatccatat tgggtccgtg ggaaatactt | 120 |
| actgcacagg aaggggggcg atctgacgag gccccgccac cggcctcgac ccgaggccga | 180 |
| ggccgacgaa gcgccggcga gtacggcgcc gcggcggcct ctgcccgtgc cctctgcgcg | 240 |
| tgggagggag aggccgcggt ggtggggggcg cgcgcgcgcg cgcgcgcagc tggtgcggcg | 300 |
| gcgcgggggt cagccgccga gccggcggcg acggaggagc agggcggcgt ggacgcgaac | 360 |
| ttccgatcgg ttggtcagag tgcgcgagtt gggcttagcc aattaggtct caacaatcta | 420 |
| ttgggccgta aaattcatgg gccctggttt gtctaggccc aatatcccgt tcatttcagc | 480 |
| ccacaaatat tccccagag gattattaag gcccacacgc agcttatagc agatcaagta | 540 |
| cgatgtttcc tgatcgttgg atcggaaacg tacggtcttg atcaggcatg ccgacttcgt | 600 |
| caaagagagg cggcatgacc tgacgcgag ttggttccgg gcaccgtctg gatggtcgta | 660 |
| ccgggaccgg acacgtgtcg cgcctccaac tacatggaca cgtgtggtgc tgccattggg | 720 |
| ccgtacgcgt ggcggtgacc gcaccggatg ctgcctcgca ccgccttgcc cacgctttat | 780 |
| atagagaggt tttctctcca ttaatcgcat agcgagtcga atcgaccgaa ggggagggg | 840 |
| agcgaagctt tgcgttctct aatcgcctcg tcaaggtaac taatcaatca cctcgtccta | 900 |
| atcctcgaat ctctcgtggt gcccgtctaa tctcgcgatt ttgatgctcg tggtggaaag | 960 |
| cgtaggagga tcccgtgcga gttagtctca atctctcagg gtttcgtgcg attttagggt | 1020 |
| gatccacctc ttaatcgagt tacggtttcg tgcgatttta gggtaatcct cttaatctct | 1080 |
| cattgattta gggtttcgtg agaatcgagg tagggatctg tgttatttat atcgatctaa | 1140 |
| tagatggatt ggttttgaga ttgttctgtc agatggggat tgtttcgata tattacccta | 1200 |
| atgatgtgtc agatggggat tgtttcgata tattacccta atgatgtgtc agatggggat | 1260 |
| tgtttcgata tattacccta atgatggata ataagagtag ttcacagtta tgttttgatc | 1320 |
| ctgccacata gtttgagttt tgtgatcaga tttagtttta cttatttgtg cttagttcgg | 1380 |
| atgggattgt tctgatattg ttccaataga tgaatagctc gttaggttaa aatctttagg | 1440 |
| ttgagttagg cgacacatag tttatttcct ctggatttgg attggaattg tgttcttagt | 1500 |
| tttttccccc tggatttgga ttggaattgt gtggagctgg gttagagaat tacatctgta | 1560 |
| tcgtgtacac ctacttgaac tgtagagctt gggttctaag gtcaatttaa tctgtattgt | 1620 |
| atctggctct tgcctagtt gaactgtagt gctgatgttg tactgtgttt ttttacccgt | 1680 |
| tttatttgct ttactcgtgc aaatcaaatc tgtcagatgc tagaactagg tggctttatt | 1740 |
| ctgtgttctt acatagatct gttgtcctgt agttacttat gtcagttttg ttattatctg | 1800 |
| aagatatttt tggttgttgc ttgttgatgt ggtgtgagct gtgagcagcg ctcttatgat | 1860 |

-continued

```
taatgatgct gtccaattgt agtgtagtat gatgtgattg atatgttcat ctattttgag    1920
ctgacagtac cgatatcgta ggatctggtg ccaacttatt ctccagctgc ttttttttac    1980
ctatgttaat tccaatcctt tcttgcctct tccagatcca gata                     2024
```

```
<210> SEQ ID NO 21
<211> LENGTH: 30
<212> TYPE: DNA
<213> ORGANISM: Artificial Sequence
<220> FEATURE:
<223> OTHER INFORMATION: Rubi3/GUS fusion

<400> SEQUENCE: 21
ctcttccaga tgcagataat gcaaatattc                                       30

<210> SEQ ID NO 22
<211> LENGTH: 7
<212> TYPE: PRT
<213> ORGANISM: Artificial Sequence
<220> FEATURE:
<223> OTHER INFORMATION: Rubi3/GUS fusion protein

<400> SEQUENCE: 22

Met Gln Ile Met Leu Arg Pro
1               5

<210> SEQ ID NO 23
<211> LENGTH: 31
<212> TYPE: DNA
<213> ORGANISM: Artificial Sequence
<220> FEATURE:
<223> OTHER INFORMATION: Rubi3/GUS fusion

<400> SEQUENCE: 23
ctcttccaga tacagataat gcaaatattc g                                     31

<210> SEQ ID NO 24
<211> LENGTH: 4
<212> TYPE: PRT
<213> ORGANISM: Artificial Sequence
<220> FEATURE:
<223> OTHER INFORMATION: Rubi3/GUS fusion protein

<400> SEQUENCE: 24

Met Leu Arg Pro
1

<210> SEQ ID NO 25
<211> LENGTH: 31
<212> TYPE: DNA
<213> ORGANISM: Artificial Sequence
<220> FEATURE:
<223> OTHER INFORMATION: Rubi3/GUS fusion

<400> SEQUENCE: 25
ctcttccaga ttcagataat gcaaatattc g                                     31

<210> SEQ ID NO 26
<211> LENGTH: 31
<212> TYPE: DNA
<213> ORGANISM: Artificial Sequence
<220> FEATURE:
<223> OTHER INFORMATION: Rubi3/GUS fusion

<400> SEQUENCE: 26
ctcttccaga tccagataat gcaaatattc g                                     31
```

```
<210> SEQ ID NO 27
<211> LENGTH: 1241
<212> TYPE: DNA
<213> ORGANISM: Oryza sativa

<400> SEQUENCE: 27
ccacccaacc ccatatcgac agaggatgtg aagaacaggt aaatcacgca gaagaaccca      60
tctctgatag cagctatcga ttagaacaac gaatccatat tgggtccgtg ggaaatactt     120
actgcacagg aaggggggcg atctgacgag gccccgccac cggcctcgac ccgaggccga     180
ggccgacgaa gcgccggcga gtacggcgcc gcggcggcct ctgcccgtgc cctctgcgcg     240
tgggagggag aggccgcggt ggtggggcg cgcgcgcgcg cgcgcgcagc tggtgcggcg      300
gcgcgggggt cagccgccga gccggcgcg acggaggagc agggcggcgt ggacgcgaac      360
ttccgatcgg ttggtcagag tgcgcgagtt gggcttagcc aattaggtct caacaatcta     420
ttgggccgta aaattcatgg gccctggttt gtctaggccc aatatcccgt tcatttcagc     480
ccacaaatat ttccccagag gattattaag gcccacacgc agcttatagc agatcaagta     540
cgatgtttcc tgatcgttgg atcggaaacg tacggtcttg atcaggcatg ccgacttcgt     600
caaagagagg cggcatgacc tgacgcggag ttggttccgg gcaccgtctg gatggtcgta     660
ccgggaccgg acacgtgtcg cgcctccaac tacatggaca cgtgtggtgc tgccattggg     720
ccgtacgcgt ggcggtgacc gcaccggatg ctgcctcgca ccgccttgcc cacgctttat     780
atagagaggt tttctctcca ttaatcgcat agcgagtcga atcgaccgaa ggggaggggg     840
agcgaagctt tgcgttctct aatcgcctcg tcaaggtaac taatcaatca cctcgtccta     900
atcctcgaat ctctcgtggt gcccgtctaa tctcgcgatt ttgatgctcg tggtggaaag     960
cgtaggagga tcgatctgtt gtcctgtagt tacttatgtc agtttgtta ttatctgaag     1020 atatttttgg ttgttgcttg ttgatgtggt gtgagctgtg agcagcgctc ttatgattaa     1080
tgatgctgtc caattgtagt gtagtatgat gtgattgata tgttcatcta tttgagctg     1140 acagtaccga tatcgtagga tctggtgcca acttattctc cagctgcttt tttttaccta    1200
tgttaattcc aatcctttct tgcctcttcc agatccagat a                        1241
```

POLYUBIQUITIN RUBI3 PROMOTER AND 5' REGULATORY SEQUENCES

RELATED APPLICATION INFORMATION

This application claims the benefit under 35 U.S.C. §371 of PCT Application No. PCT/US2004/015286, filed on May 14, 2004, which claims priority from U.S. Provisional Application No. 60/471,007, filed on May 16, 2003, the disclosures of which are incorporated by reference herein in their entireties.

FIELD OF THE INVENTION

The present invention relates to the field of plant molecular biology, more particularly to regulation of nucleic acid expression in plants.

BACKGROUND OF THE INVENTION

Ubiquitin is a highly conserved 76-amino acid protein present in all eukaryotic cells (Callis and Vierstra (1989) *Oxford Surv. Plant Mol. Cell. Biol.* 6:1-30). Ubiquitin is encoded by small multigenic families containing two types of genes, polyubiquitin and ubiquitin extension/fusion genes. The polyubiquitin gene consists of tandem repeats of a 228 bp ubiquitin coding region (Burke, et al. (1988) *Mol. Gen. Genet.* 213:435-443; Binet, et al. (1991) *Plant Mol. Biol.* 17:395-407; Christensen, et al. (1992) *Plant Mol. Biol.* 18:675-689). The ubiquitin genes are translated as a polyprotein precursor, then proteolytically processed to functional ubiquitin monomers. The polyubiquitin genes are constitutively expressed in all plant organs that have been tested, with increased levels in young tissues (Binet, et al. (1991) *Plant Sci.* 79:87-94; Kawalleck, et al. (1993) *Plant Mol. Biol.* 21:673-684; Burke, et al. (1988) supra; Cornejo, et al. (1993) *Plant Mol Biol Rep* 14:19-21).

Promoters of polyubiquitin genes have been tested and reported to have high constitutive expression of foreign genes placed under their control. Such promoters have been isolated from *Arabidopsis* (Callis, et al., (1990) *J. Biol. Chem.* 265: 12486-12493; Norris, et al. (1993) *Plant Mol. Biol.* 21:895-906), sunflower (Binet, et al. (1991) supra), tobacco (Genschik, et al. (1994) *Gene* 148:195-202), potato (Garbino and Belknap (1994) *Plant Mol. Biol.* 24:119-127), maize (Christensen, et al. (1992) supra), sugarcane (Wei, et al. (1999) *J. Plant Physiol.* 155:513-519) and rice (Wang, et al. (2000) *Plant Sci.* 156(2):201-211). Among these, the maize polyubiquitin Ubi1 promoter has been used in maize and other monocot transformation systems (Christensen, et al. (1992) supra; Cornejo, et al. (1993) supra; Christensen and Quail (1996) *Transgenic Res.* 5:213-218).

SUMMARY OF THE INVENTION

The ability to manipulate gene expression in plants facilitates the production of plants with improved and/or new characteristics. There are some situations in which it is desirable to express a foreign (i.e., exognenous) nucleic acid sequence or an additional or modified copy of an endogenous sequence in a plant, plant tissue culture or plant cell, etc., for example, for the production of polypeptides of agronomic, nutritional or commercial value, or the regulation of endogenous gene expression with antisense RNA or interfering RNA (RNAi).

The present invention provides compositions and methods for regulating expression of a heterologous nucleotide sequence(s) of interest in plants. In particular, the invention provides novel regulatory elements and methods for expressing a nucleotide sequence of interest in a plant, plant tissue, plant cell, and the like.

Accordingly, as a first aspect, the present invention provides an isolated nucleic acid comprising an expression control element comprising a nucleotide sequence selected from the group consisting of: (a) the nucleotide sequence of SEQ ID NO:1, SEQ ID NO:2, SEQ ID NO:3, SEQ ID NO:17, SEQ ID NO:18, SEQ ID NO:19 or SEQ ID NO:20; (b) a nucleotide sequence consisting essentially of a biologically active fragment of at least 50 consecutive nucleotides of the nucleotide sequence of SEQ ID NO:1, SEQ ID NO:2, SEQ ID NO:3, SEQ ID NO:17, SEQ ID NO:18, SEQ ID NO:19 or SEQ ID NO:20; (c) a nucleotide sequence that hybridizes to the complement of the nucleotide sequences of (a) or (b) under stringent hybridization conditions, wherein the nucleotide sequence is biologically active as an expression control element; and (d) a nucleotide sequence having at least 95% sequence identity to the nucleotide sequences of (a) or (b), wherein the nucleotide sequence is biologically active as an expression control element.

A further aspect of the invention provides expression cassettes comprising the isolated nucleic acids of the invention operably linked to a heterologous nucleotide sequence of interest.

As still further aspects, the present invention provides vectors and cells comprising the isolated nucleic acids and expression cassettes of the invention.

As yet another aspect, the present invention provides stably transformed plants and seeds comprising the isolated nucleic acids, expression cassettes and vectors of the invention.

Also provided by the present invention are methods of introducing a nucleotide sequence into a plant, plant tissue, plant cell or plant seed comprising transforming a plant, plant tissue, plant cell or plant seed with an isolated nucleic acid, expression cassette or vector of the invention.

Further provided are methods of expressing a heterologous nucleotide sequence in a plant, plant tissue, plant cell or plant seed comprising transforming a plant, plant tissue, plant cell or plant seed with an isolated nucleic acid, expression cassette or vector of the invention, and expressing the heterologous nucleotide sequence of interest in the plant, plant tissue, plant cell or plant seed.

As yet another aspect, the invention provides methods of expressing a nucleotide sequence in a plant comprising: stably transforming a plant cell or plant tissue with an isolated nucleic acid, expression cassette or vector of the invention, and regenerating a stably transformed plant, and expressing the heterologous nucleotide sequence of interest in the plant.

Also provided are methods of producing a polypeptide of interest in a plant, plant cell, plant tissue or plant seed of the invention.

These and other aspects of the invention are set forth in more detail in the description of the invention below.

BRIEF DESCRIPTION OF THE DRAWINGS

FIGS. 1A-1H show regulatory sequences of the rubi3 gene. FIG. 1A, rubi3 promoter and 5' UTR (untranslated region) intron (SEQ ID NO:1); FIG. 1B, rubi3 promoter only (SEQ ID NO:2); FIG. 1C, 5' UTR intron only (SEQ ID NO:3); FIGS. 1D-1G, rubi3 promoter, 5' UTR intron, and first nine nucleotides of the coding sequence (double-underlined), wherein the third position of said coding sequence contains a G (FIG. 1D; SEQ ID NO:17), A (FIG. 1E; SEQ ID NO:18), T (FIG. 1F; SEQ ID NO:19), or C (FIG. 1G; SEQ ID NO:20). FIG. 1H depicts the sequence of an 780 bp deletion mutant of the rubi3 intron (SEQ ID NO:27). The TATA box is underlined. The transcription initiation site is double-underlined. CAAT boxes are in lower case letters.

FIGS. 2A and 2B show the nucleotide sequence (SEQ ID NO:8) and amino acid sequence (SEQ ID NO:9) of rice rubi3. The 5'-upstream region of rice rubi3 is depicted in lowercase letters. The TATA box and transcription initiation site (26 nucleotides downstream of the TATA box) are double-underlined. Downstream is the 5' UTR intron shown by single underline. The 5' and 3' intron splice sites are boxed. The 918 nucleotide polyubiquitin coding region of rubi3 and deduced amino acid sequence are indicated.

FIGS. 3A-C show a CLUSTAL W multiple sequence alignment of RUBQ1 (R1; accession number AF184279; SEQ ID NO:14), RUBQ2 (R2; accession number AF184280; SEQ ID NO:15) and rubi3 (R3; SEQ ID NO:3) ubiquitin introns of rice and the maize (M; SEQ ID NO:16) ubiquitin intron.

FIG. 6 shows transient GUS activity in rice suspension cells transformed with the rice rubi3 promoter-driving GUS gene expression in comparison with other constructs.

FIG. 7 is a schematic representation of the pRESQ42 construct and its derivatives showing the nucleotide fusion between the rubi3 5' UTR intron and GUS coding sequence and the resulting N-terminal sequence of the translated products. Mutated nucleotides are underlined.

DETAILED DESCRIPTION OF THE INVENTION

Figure 4A:
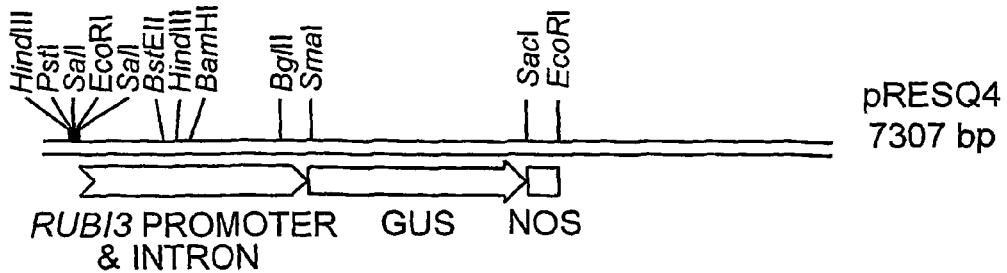
FIGS. 4A-E illustrate constructs containing the rubi3 promoter, GUS coding sequence and NOS terminator.

The present invention is based, in part, on the discovery of new 5' expression control elements from the rice rubi3 polyubiquitin gene. These regulatory elements include the rubi3 promoter, an intron sequence that is located immediately 5' to the translational start site in the rice gene, and a downstream enhancing element (i.e., downstream of the regulatory intron) located within the first 9 nucleotides of the rubi3 coding sequence. These regulatory elements can be used independently, together, or in operable association with other, heterologous (e.g., from a foreign gene) regulatory elements. For example, the inventors disclose herein expression constructs containing a rice actin or H3 promoter operably associated with the rubi3 intron sequence.

The present invention will now be described in more detail with reference to the accompanying drawings, in which preferred embodiments of the invention are shown. This invention may, however, be embodied in different forms and should not be construed as limited to the embodiments set forth herein. Rather, these embodiments are provided so that this disclosure will be thorough and complete, and will fully convey the scope of the invention to those skilled in the art.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention. All publications, patent applications, patents, and other references mentioned herein are incorporated by reference in their entirety.

Nucleotide sequences are presented herein by single strand only, in the 5' to 3' direction, from left to right, unless specifically indicated otherwise. Nucleotides and amino acids are represented herein in the manner recommended by the IUPAC-IUB Biochemical Nomenclature Commission, or (for amino acids) by either the one-letter code, or the three letter code, both in accordance with 37 CFR §1.822 and established usage.

Except as otherwise indicated, standard methods known to those skilled in the art may be used for cloning genes, amplifying and detecting nucleic acids, and the like. Such techniques are known to those skilled in the art. See, e.g., SAMBROOK et al., MOLECULAR CLONING: A LABORATORY MANUAL 2nd Ed. (Cold Spring Harbor, N.Y., 1989); F. M. AUSUBEL et al. CURRENT PROTOCOLS IN MOLECULAR BIOLOGY (Green Publishing Associates, Inc. and John Wiley & Sons, Inc., New York).

I. Definitions.

As used in the description of the invention and the appended claims, the singular forms "a," "an" and "the" are intended to include the plural forms as well, unless the context clearly indicates otherwise.

As used herein a "chimeric nucleic acid" or "chimeric nucleotide sequence" comprises an expression control element operably linked to a nucleotide sequence of interest that is heterologous (i.e., foreign) to the expression control element. In particular embodiments, the "chimeric nucleic acid" or "chimeric nucleotide sequence" comprises a rubi3 expression control element operably associated with a heterologous nucleotide sequence of interest to be transcribed.

An "expression control element" is a nucleotide sequence that controls or regulates the expression of a coding sequence. The expression control element may act at the transcriptional level, the RNA processing level, or the translational level. A promoter is one type of expression control element, as are other 5' regulatory sequences such as the rubi3 and Act1 intron sequences described herein. Also disclosed herein is an enhancing element at the 5' end of the rubi3 coding sequence.

A "promoter" refers to the nucleotide sequence that contains a binding site for RNA polymerase II and directs the initiation of transcription. In general, promoters are found 5', or upstream, relative to the start of the coding region of the corresponding gene. A promoter sequence is necessary, but not always sufficient, to drive transcription of a downstream sequence. The promoter region may also comprise other elements that act as regulators of gene expression. These include a TATA box consensus sequence, and often a CMT box consensus sequence (Breathnach and Chambon, (1981) *Annu. Rev. Biochem.* 50:349). In plants, the CAAT box may be substituted by the AGGA box (Messing et al., (1983) in Genetic Engineering of Plants, T. Kosuge, C. Meredith and A. Hollaender (eds.), Plenum Press, pp. 211-227). The promoter region, including all the ancillary regulatory elements, typically contain between 100 and 1000 nucleotides, but can be as long as 2 kb, 3 kb, 4 kb or longer in length. Promoters according to the present invention can function as constititive or inducible regulatory elements.

By "operably linked" or "operably associated" as used herein, it is meant that the indicated elements are functionally related to each other, and are also generally physically related. For example, a promoter is operatively linked to a coding sequence if it controls the transcription of the sequence. Thus, the term "operatively linked" or "operably associated" as used herein, refers to nucleotide sequences on a single nucleic acid molecule that are functionally associated.

A "heterologous nucleotide sequence" or "heterologous nucleotide sequence of interest" as used herein is a coding sequence that is heterologous to (i.e., foreign, exogenous or non-native to) the rubi3 expression control elements of the invention (i.e., is not the native rubi3 coding sequence). The heterologous nucleotide sequence can encode a polypeptide or a nontranslated RNA.

By the term "express" or "expression" of a nucleic acid coding sequence, it is meant that the sequence is transcribed. In particular embodiments, the terms "express" and "expression" can refer to both transcription and translation to produce an encoded polypeptide.

As used herein, the term "polypeptide" encompasses both peptides and proteins, unless indicated otherwise.

A "biologically active" or "functional" nucleotide sequence is one that substantially retains at least one biological activity normally associated with that nucleotide sequence, for example, ability to drive transcription, translation and/or RNA processing, and the like of an operatively associated coding sequence. In particular embodiments, the "biologically active" or "functional" nucleotide sequence substantially retains all of the biological activities possessed by the unmodified sequence. By "substantially retains" biological activity, it is meant that the nucleotide sequence retains at least about 50%, 60%, 75%, 85%, 90%, 95%, 97%, 98%, 99%, or more, of the biological activity of the native nucleotide sequence (and can even have a higher level of activity than the native nucleotide sequence). For example, a biologically active expression control element is able to promote or enhance the expression of a nucleic acid operably associated with the expression control element. Methods of measuring expression of a nucleotide sequence are well known in the art and include Northern blots, RNA run-on assays and methods of measuring the presence of the encoded polypeptide (e.g., antibody based methods or visual inspection in the case of a reporter polypeptide).

As used herein, an "isolated" nucleic acid (e.g., an "isolated DNA") means a nucleic acid separated or substantially free from at least some of the other components of the naturally occurring organism or virus, such as for example, the cell or viral structural components or other polypeptides or nucleic acids commonly found associated with the nucleic acid.

Likewise, an "isolated" polypeptide means a polypeptide that is separated or substantially free from at least some of the other components of the naturally occurring organism or virus, for example, the cell or viral structural components or other polypeptides or nucleic acids commonly found associated with the polypeptide. In particular embodiments, the "isolated" polypeptide is at least about 1%, 5%, 10%, 25%, 50%, 60%, 70%, 75%, 80%, 85%, 90%, 95%, 97%, 98%, 99% or more pure (w/w). In other embodiments, an "isolated" polypeptide indicates that at least about a 5-fold, 10-fold, 25-fold, 100-fold, 1000-fold, 10,000-fold, or more enrichment of the protein (w/w) is achieved as compared with the starting material.

II. rubi3 Expression Control Elements.

As one aspect, the invention provides isolated nucleic acids comprising one or more rubi3 expression control elements (or biologically active fragments or variations thereof). The rubi3 expression control elements of the invention encompass homologs from any species (e.g., plants) as well as biologically active fragments of naturally occurring rubi3 expression control elements or biologically active variants thereof that contain insertions, deletions and/or substitutions in the naturally occurring sequences and fragments. The expression control elements of the invention can further be isolated from natural sources or may be wholly or partially synthetic. Those skilled in the art will appreciate that in addition to the promoter, 5' UTR intron and downstream enhancing element (at the 5' end of the rubi3 coding sequence) described herein, the isolated nucleic acid can comprise other sequences from the rubi3 gene, e.g., all or a portion of the 5' UTR sequence that lies between the promoter and the intron sequences (see FIGS. 1A, 2A and 2B) or some of the flanking sequences (e.g., up to about 20, 50, 100, 200, 300, 500, 1000, 2000, 3000 nucleotides or more) that are positioned upstream of the rubi3 promoter. Further, as described below, the isolated nucleic acid can comprise some or all of the rubi3 coding sequence. In particular embodiments, described in more detail below, the first codon of the rubi3 coding sequence is modified so that it no longer acts as a translational start site (i.e., the modified coding sequence is transcribed but not translated).

Homologous sequences from other organisms, in particular other plants, can be routinely identified using methods known in the art. For example, PCR and other amplification techniques and hybridization techniques can be used to identify such homologs based on their sequence similarity to the sequences set forth herein.

Thus, in exemplary embodiments, the isolated nucleic acid comprises, consists essentially of, or consists of the nucleotide sequence of SEQ ID NO:1, SEQ ID NO:2, SEQ ID NO:3, SEQ ID NO:17, SEQ ID NO:18, SEQ ID NO:19 or SEQ ID NO:20. With respect to the intron sequence of SEQ ID NO:3 (as well as SEQ ID NO:1, SEQ ID NO:17, SEQ ID NO:18, SEQ ID NO:19 and SEQ ID NO:20), it will be understood by those skilled in the art that efficient intron splicing generally requires the complete 5' and 3' splice recognition sites. It has been documented that the splice recognition site regions are well conserved and have the following consensus sequences: NNCAAG/gtragu . . . y(n)ncag/RNN (Dibb, (1993) *FEBS* 325:135-139). Thus, in particular embodiments, the intron sequences of the invention comprise the complete 5' and 3' splice recognition sites (see, e.g., FIG. 2A).

In other representative embodiments, the isolated nucleic acid comprises, consists essentially of or consists of a biologically active fragment or biologically active variant of SEQ ID NO:1, SEQ ID NO:2, SEQ ID NO:3, SEQ ID NO:17, SEQ ID NO:18, SEQ ID NO:19 or SEQ ID NO:20. In particular embodiments, the biologically active fragment or variant of the rubi3 promoter sequence comprises the TATA box sequence and/or one or more CAAT box sequences (FIGS. 1A, 1B and 2A).

The length of the biologically active fragment is not critical as long as it substantially retains the biological activity of the expression control element. Illustrative fragments comprise at least about 20, 30, 40, 50, 60, 100, 150, 200, 250, 300, 400, 500, 600 or 700 contiguous nucleotides or more of the full-length sequence. In other embodiments, a biologically active fragment of the rubi3 promoter comprises the nucleotide sequence of SEQ ID NO:2 having a deletion of up to 5, 10, 20, 30, 50, 100, 200, 250, 300, 400 or 500 nucleotides at the 5' and/or 3' end. In still further embodiments, the biologically active fragment of the rubi3 promoter sequence comprises a fragment from about nucleotide 1, 5, 10, 20, 30, 50, 75, 100, 150, 200, 250, 300, 350, 400, 500, 550, 600 or 650 of SEQ ID NO:2 to about nucleotide 300, 350, 400, 450, 500, 550, 600, 700, 750, 800, 810, 820, 830, 840 or 851 (inclusive) of SEQ ID NO:2, including any combination thereof.

Further, in other representative embodiments, a biologically active variant of the rubi3 promoter of SEQ ID NO:2 comprises internal deletions of up to about 5, 10, 20, 30, 50, 100, 200, 250, 300, 400 or 500 nucleotides. There may be a single or multiple internal deletions.

Those skilled in the art will appreciate that biologically active fragments or internal deletion variants of the intron regulatory sequence will generally require appropriate 5' and 3' splice signals for proper processing. Thus, in representative embodiments, a biologically active variant of the rubi3 intron sequence comprises 5' and 3' splice site recognition sequence motifs and optionally further comprises an internal nucleotide sequence positioned between the splice recognition sites which is a deleted form of the sequence from nucleotide 5 though nucleotide 1137 inclusive) of SEQ ID NO:3 having deletion of up to about 5, 10, 20, 30, 50, 100, 200, 250, 300, 400, 500, 600, 700, 800, 900 or 1000 nucleotides, where the deletion(s) is internal and/or is at the 5' and/or 3' ends of the indicated sequence (see, e.g., FIG. 1H). In another illustrative embodiment, the entire internal sequence of the intron (i.e., other than the splice recognition sites), or essentially the entire internal sequence of the intron (e.g., all but about 5, 10, 25, 50 nucleotides or less), is deleted.

In one representative embodiment, the variant 5' UTR intron comprises 5' and 3' splice recognition signals. The 5' UTR intron can optionally further comprise an internal nucleotide sequence positioned between the 5' and 3' splice recognition signals. In particular embodiments, the internal nucleotide sequence comprises at least about 5, 10, 20, 30, 50, 100, 200, 250, 300, 400, 500, 600, 700, 800, 900 or 1000 consecutive nucleotides from the nucleotide sequence of nucleotide 5 through nucleotide 1137 (inclusive) of SEQ ID NO:3, wherein the 5' UTR intron is biologically active as an expression control element. The 5' UTR intron can further comprise two or more segments of the intron sequence from nucleotide 5 through nucleotide 1137 (inclusive) of SEQ ID NO:3. For example, the 5' UTR can include separate segments of the intron sequence adjacent to each of the splice recognition sites, which can optionally be contiguous to each other as a result of the deletion of the intervening region of the intron sequence.

Alternatively, the internal intron sequence can be modified by insertion or substitution of one or more nucleotides.

The 5' and 3' splice site motifs of the 5' UTR intron elements of the invention can be those shown in FIG. 2A or, alternatively, can be any other functional splice site recognition region known in the art (see consensus sequence above).

In other embodiments of the invention, one or both of the intron splice recognition sites is altered so that the intron is not efficiently spliced.

In representative embodiments, the expression control element of the invention is a biologically active variant of the rubi3 sequences or fragments described above and comprises, consists essentially of, or consists of a nucleotide sequence that will hybridize to the rubi3 nucleotide sequences disclosed herein (i.e., SEQ ID NO:1, SEQ ID NO:2, SEQ ID NO:3, SEQ ID NO:17, SEQ ID NO:18, SEQ ID NO:19, or SEQ ID NO:20 or biologically active fragments thereof) under standard conditions as known by those skilled in the art.

For example, hybridization of such sequences may be carried out under conditions of reduced stringency, medium stringency or even stringent conditions (e.g., conditions represented by a wash stringency of 35-40% Formamide with 5× Denhardt's solution, 0.5% SDS and 1×SSPE at 37° C.; conditions represented by a wash stringency of 40-45% Formamide with 5× Denhardt's solution, 0.5% SDS, and 1×SSPE at 42° C.; and conditions represented by a wash stringency of 50% Formamide with 5× Denhardt's solution, 0.5% SDS and 1×SSPE at 42° C., respectively) to the rubi3 expression control elements or biologically active fragments thereof disclosed herein. See, e.g., Sambrook et al., *Molecular Cloning, A Laboratory Manual* (2d Ed. 1989) (Cold Spring Harbor Laboratory).

In other embodiments, the nucleotide sequence of an expression control element of the invention has at least about 60%, 70%, 80%, 85%, 90%, 95%, 97% or higher nucleotide sequence similarity to a nucleotide sequence specifically disclosed herein (e.g., SEQ ID NO:1, SEQ ID NO:2, SEQ ID NO:3, SEQ ID NO:17, SEQ ID NO:18, SEQ ID NO:19 or SEQ ID NO:20 or biologically active fragments thereof.

As is known in the art, a number of different programs can be used to identify whether a nucleic acid or amino acid has sequence identity or similarity to a known sequence. Sequence identity or similarity may be determined using standard techniques known in the art, including, but not limited to, the local sequence identity algorithm of Smith & Waterman, *Adv. Appl. Math.* 2, 482 (1981), by the sequence identity alignment algorithm of Needleman & Wunsch, *J. Mol. Biol.* 48, 443 (1970), by the search for similarity method of Pearson & Lipman, *Proc. Natl. Acad. Sci. USA* 85, 2444 (1988), by computerized implementations of these algorithms (GAP, BESTFIT, FASTA, and TFASTA in the Wisconsin Genetics Software Package, Genetics Computer Group, 575 Science Drive, Madison, Wis.), the Best Fit sequence program described by Devereux et al., *Nucl. Acid Res.* 12, 387-395 (1984), preferably using the default settings, or by inspection.

An example of a useful algorithm is PILEUP. PILEUP creates a multiple sequence alignment from a group of related sequences using progressive, pairwise alignments. It can also plot a tree showing the clustering relationships used to create the alignment. PILEUP uses a simplification of the progressive alignment method of Feng & Doolittle, *J. Mol. Evol.* 35, 351-360 (1987); the method is similar to that described by Higgins & Sharp, *CABIOS* 5, 151-153 (1989).

Another example of a useful algorithm is the BLAST algorithm, described in Altschul et al., *J. Mol. Biol.* 215, 403-410, (1990) and Karlin et al., *Proc. Natl. Acad. Sci. USA* 90, 5873-5787 (1993). A particularly useful BLAST program is the WU-BLAST-2 program which was obtained from Altschul et al., *Methods in Enzymology,* 266, 460-480 (1996). WU-BLAST-2 uses several search parameters, which are preferably set to the default values. The parameters are dynamic values and are established by the program itself depending upon the composition of the particular sequence and composition of the particular database against which the sequence of interest is being searched; however, the values may be adjusted to increase sensitivity.

An additional useful algorithm is gapped BLAST as reported by Altschul et al. *Nucleic Acids Res.* 25, 3389-3402 (1997).

The CLUSTAL program can also be used to determine sequence similarity. This algorithm is described by Higgins et al. (1988) *Gene* 73:237; Higgins et al. (1989) *CABIOS* 5:151-153; Corpet et al. (1988) *Nucleic Acids Res.* 16: 10881-90; Huang et al. (1992) *CABIOS* 8: 155-65; and Pearson et al. (1994) *Meth. Mol. Biol.* 24: 307-331.

The alignment may include the introduction of gaps in the sequences to be aligned. In addition, for sequences which contain either more or fewer nucleotides than the nucleic acids disclosed herein, it is understood that in one embodiment, the percentage of sequence identity will be determined based on the number of identical nucleotides acids in relation to the total number of nucleotide bases. Thus, for example, sequence identity of sequences shorter than a sequence specifically disclosed herein, will be determined using the number of nucleotide bases in the shorter sequence, in one embodiment. In percent identity calculations relative weight is not assigned to various manifestations of sequence variation, such as, insertions, deletions, substitutions, etc.

In other representative embodiments, the isolated nucleic acid further comprises a downstream enhancing element comprising all or part of the rubi3 coding sequence, or a non-translated modification thereof, that enhances expression (transcription and/or translation) of an operably associated heterologous nucleotide sequence. In particular embodiments, the rubi3 downstream enhancing element comprises, consists essentially of, or consists of at least about 1, 2, 3, 4, 5, 6, 7, 8, 9, 10, 11, 12, 15, 20, 30, 40, 50, 60, 75, 100, 125, 150 or 200 nucleotides of the rubi3 coding sequence (counting from the 5' end; the rubi3 coding sequence is shown as nucleotides 2106 to 2933 of SEQ ID NO:8 in FIGS. 2A and 2B) or even the entire rubi3 coding sequence. In representative embodiments, the downstream enhancing element comprises, consists essentially of or consists of the first 9 nucleotides of the rubi3 coding sequence. Accordingly, in some embodiments, the downstream enhancing element encodes the N-terminal 1, 2, 3, 4, 5, 6, 9, 12, 15, 20, 25, 30, 40, 50, 60, 70 amino acids or all 76 amino acids of a ubiquitin monomer (see, e.g., FIGS. 2A and 2B; amino acids 1-76 of SEQ ID NO:9).

The inventors have discovered that the first codon (i.e., nucleotides 1-3, ATG) of the rubi3 coding sequence can be modified so that it no longer functions as a translational start codon, i.e., so that the modified rubi3 coding sequence is transcribed but not translated without impairing the enhancing activity of the 5' rubi3 downstream enhancing element. One advantage of this embodiment of the invention is that it avoids expression of a fusion protein comprising part or all of the ubiquitin protein fused to the polypeptide encoded by the heterologous nucleotide sequence. Further, in particular embodiments, modification of the initiation codon to ablate translation can result in increased enhancing activity from the downstream enhancing element.

The translational start codon (ATG) can be modified so that it no longer functional by substitution, deletion and/or insertion at any position within the codon. For example, a C, T or G can be substituted for the A at position 1 and/or an A, C or G can be substituted for the T at position 2 and/or an A, T or C can be substituted for the G at position 3. In illustrative embodiments, the first codon of the rubi3 coding sequence is modified from ATG→ATA, ATC or ATT.

In other representative embodiments, the rubi3 downstream enhancing element comprises, consists essentially of, or consists of the first 9 nucleotides of the rubi3 coding sequence (ATGCAGATA) or the modified sequences ATA-CAGATA, ATCCAGATA or ATTCAGATA. Those skilled in the art will appreciate that the invention further encompasses variants of these downstream enhancing element having one, two, three, four, five or more nucleotide substitutions as long as the downstream enhancing element still provides enhanced expression of an operably associated heterologous nucleotide sequence of interest.

In further exemplary embodiments, the isolated nucleic acid comprises, consists essentially of, or consists of the nucleotide sequence of SEQ ID NO:17, SEQ ID NO:18, SEQ ID NO:19, or SEQ ID NO:20 or biologically active fragments or variants thereof (as described above).

In other embodiments of the invention, the isolated nucleic acid does not include any of the rubi3 coding sequence.

The invention further provides an expression cassette comprising an expression control element(s) of the invention. The expression cassette generally comprises a promoter, which in particular embodiments is a rubi3 promoter of the invention or a biologically active fragment or variant thereof (as described above), operably linked to a heterologous nucleotide sequence of interest. In particular embodiments, the expression cassette comprises more than one (e.g., two, three, four or more) heterologous nucleotide sequences. The expression cassette can further have a plurality of restriction sites for insertion of a heterologous nucleotide sequences to be operably linked to the regulatory regions.

The expression cassette may further comprise a transcriptional termination sequence. Any suitable termination sequence known in the art may be used in accordance with the present invention. The termination region may be native with the transcriptional initiation region, may be native with the nucleotide sequence of interest, or may be derived from another source. Convenient termination regions are available from the Ti-plasmid of *A. tumefaciens*, such as the octopine synthetase and nopaline synthetase termination regions. See also, Guerineau et al., *Mol. Gen. Genet.* 262, 141 (1991); Proudfoot, *Cell* 64, 671 (1991); Sanfacon et al., *Genes Dev.* 5, 141 (1991); Mogen et al., *Plant Cell* 2, 1261 (1990); Munroe et al., *Gene* 91, 151 (1990); Ballas et al., *Nucleic Acids Res.* 17, 7891 (1989); and Joshi et al., *Nucleic Acids Res.* 15, 9627 (1987). Additional exemplary termination sequences are the pea RubP carboxylase small subunit termination sequence and the Cauliflower Mosaic Virus 35S termination sequence. Other suitable termination sequences will be apparent to those skilled in the art.

Further, in particular embodiments, the heterologous nucleotide sequence is operably associated with a translational start site. The translational start site can be derived from the rubi3 coding sequence or, alternatively, can be the endogenous translational start site associated with the heterologous nucleotide sequence or any other suitable translational start codon. Thus, in some embodiments, the heterologous nucleotide sequence is expressed as a fusion protein. In other embodiments, the heterologous nucleotide sequence is not expressed as a fusion protein.

In illustrative embodiments, the expression cassette includes in the 5' to 3' direction of transcription, a promoter, a heterologous nucleotide sequence of interest, and a transcriptional and translational termination region functional in plants.

The expression cassette can further comprise a regulatory intron, for example, the rubi3 5' UTR intron (or biologically active variants thereof, as described above) or another regulatory intron from a monocot plant gene, which is generally positioned in the 5' UTR between the promoter and the heterologous nucleotide sequence. In particular embodiments, the expression cassette further comprises a downstream enhancing element that is positioned between the intron and the heterologous nucleotide sequence. The intron can optionally be positioned adjacent to (with only an insignificant number of intervening nucleotide bases, e.g., less than about 25, 20, 15, 10, or 5 intervening nucleotide bases or even no intervening nucleotides) the downstream enhancing element (if present) or adjacent to the heterologous nucleotide sequence of interest (i.e., if the downstream enhancing element is not present).

The expression cassette can additionally comprise a rubi3 downstream enhancing element or a modified rubi3 non-translated downstream enhancing element or variants thereof as described above. In representative embodiments, the downstream enhancing element is positioned between a 5' UTR regulatory intron and the heterologous sequence of interest, i.e., downstream of the intron and upstream of the heterologous sequence). The downstream enhancing element may optionally be positioned adjacent to of the heterologous nucleotide sequence of interest and/or adjacent to the regulatory intron.

In one particular embodiment, the orientation of these elements within the expression cassette from the 5' to 3' direction is the rubi3 promoter (or biologically active variant or fragment thereof), optionally the rubi3 5' UTR intron (or biologically active variant or fragment thereof, and a rubi3 downstream enhancing element (or biologically active variant thereof) and the heterologous nucleotide sequence of interest.

In other particular embodiments of the invention, the expression cassette comprises the rubi3 5' UTR intron sequence (or biologically active variants or fragments thereof) operably linked to a heterologous (i.e., foreign) promoter and a heterologous nucleotide sequence of interest such that the intron enhances expression of a heterologous nucleotide sequence from the promoter. According to representative embodiments, these elements are configured in the 5' to 3' direction as: promoter, 5' UTR rubi3 intron (or biologically active variant or fragment thereof) and a heterologous nucleotide sequence of interest. The expression cassette can further optionally comprise a downstream enhancing element of the invention positioned between the 5' UTR intron and the heterologous nucleotide sequence. The heterologous promoter can be any suitable promoter known in the art (including bacterial, yeast, fungal, insect, mammalian, and plant promoters). In particular embodiments, the promoter is a promoter for expression in plants. Exemplary promoters include, but are not limited to, the Cauliflower Mosaic Virus 35S promoter, the opine synthetase promoters (e.g., nos, mas, ocs, etc.), another ubiquitin promoter, an actin promoter (e.g., Act1 promoter), H3 promoter, the ribulose bisphosphate (RubP) carboxylase small subunit promoter, and the alcohol dehydrogenase promoter. Other suitable promoters include promoters from viruses that infect the host plant including, but not limited to, promoters isolated from Dasheen mosaic virus, Chlorella virus (e.g., the Chlorella virus adenine methyltransferase promoter; Mitra et al., (1994) *Plant Molecular Biology* 26:85), tomato spotted wilt virus, tobacco rattle virus, tobacco necrosis virus, tobacco ring spot virus, tomato ring spot virus, cucumber mosaic virus, peanut stump virus, alfalfa mosaic virus, and the like.

In illustrative embodiments, the expression cassette comprises in the 5' to 3' direction: a rubi3 promoter, a 5' UTR rubi3 intron, and a rubi3 downstream enhancing element (or biologically active variants or fragments of the foregoing), and a heterologous nucleotide sequence(s) of interest, wherein the 5' UTR rubi3 intron is adjacent to the rubi3 downstream enhancing element, which is in turn adjacent to the heterologous nucleotide sequence of interest.

Those skilled in the art will understand that the expression cassettes of the invention can further comprise enhancer elements and/or tissue preferred elements in combination with the expression control sequences of the invention.

Further, in some embodiments, it is advantageous for the expression cassette to comprise a selectable marker gene for the selection of transformed cells. Selectable marker genes include genes encoding antibiotic resistance, such as those encoding neomycin phosphotransferase II (NEO) and hygromycin phosphotransferase (HPT), as well as genes conferring resistance to herbicidal compounds. Herbicide resistance genes generally code for a modified target protein insensitive to the herbicide or for an enzyme that degrades or detoxifies the herbicide in the plant before it can act. See, DeBlock et al., *EMBO J.* 6, 2513 (1987); DeBlock et al, *Plant Physiol.* 91, 691 (1989); Fromm et al., *BioTechnology* 8, 833 (1990); Gordon-Kamm et al., *Plant Cell* 2, 603 (1990). For example, resistance to glyphosphate or sulfonylurea herbicides has been obtained using genes coding for the mutant target enzymes, 5-enolpyruvylshikimate-3-phosphate synthase (EPSPS) and acetolactate synthase (ALS). Resistance to glufosinate ammonium, boromoxynil, and 2,4-dichlorophenoxyacetate (2,4-D) have been obtained by using bacterial genes encoding phosphinothricin acetyltransferase, a nitrilase, or a 2,4-dichlorophenoxyacetate monooxygenase, which detoxify the respective herbicides.

Selectable marker genes that can be used according to the present invention further include, but are not limited to, genes encoding: neomycin phosphotransferase II (Fraley et al, *CRC Critical Reviews in Plant Science* 4, 1 (1986)); cyanamide hydratase (Maier-Greiner et al, *Proc. Natl. Acad. Sci. USA* 88, 4250 (1991)); aspartate kinase; dihydrodipicolinate synthase (Perl et al, *BioTechnology* 11, 715 (1993)); the bar gene (Toki et al, *Plant Physiol.* 100, 1503 (1992); Meagher et al, *Crop Sci.* 36, 1367 (1996)); tryptophane decarboxylase (Goddijn et al, *Plant Mol. Biol.* 22, 907 (1993)); neomycin phosphotransferase (NEO; Southern et al, *J. Mol. Appl Gen.* 1, 327 (1982)); hygromycin phosphotransferase (HPT or HYG; Shimizu et al, *Mol. Cell. Biol* 6, 1074 (1986)); dihydrofolate reductase (DHFR; Kwok et al, *Proc. Natl. Acad. Sci. USA* 83, 4552 (1986)); phosphinothricin acetyltransferase (DeBlock et al, *EMBO J.* 6, 2513 (1987)); 2,2-dichloropropionic acid dehalogenase (Buchanan-Wollatron et at, *J. Cell. Biochem.* 13D, 330 (1989)); acetohydroxyacid synthase (U.S. Pat. No. 4,761,373 to Anderson et at; Haughn et al, *Mol. Gen. Genet.* 221, 266 (1988)); 5-enolpyruvyl-shikimate-phosphate synthase (aroA; Comai et al, *Nature* 317, 741 (1985)); haloarylnitrilase (WO 87/04181 to Stalker et al); acetyl-coenzyme A carboxylase (Parker et al., *Plant Physiol* 92, 1220 (1990)); dihydropteroate synthase (sulI; Guerineau et al, *Plant Mol. Biol.* 15, 127 (1990)); and 32 kDa photosystem II polypeptide (psbA; Hirschberg et al., *Science* 222, 1346 (1983)).

Also included are genes encoding resistance to: chloramphenicol (Herrera-Estrella et al., *EMBO J.* 2, 987 (1983)); methotrexate (Herrera-Estrella et al., *Nature* 303, 209 (1983)); Meijer et al., *Plant Mol. Biol.* 16, 807 (1991)); hygromycin (Waldron et al., *Plant Mol. Biol.* 5, 103 (1985); Zhijian et al., *Plant Science* 108, 219 (1995); Meijer et al., *Plant Mol. Bio.* 16, 807 (1991)); streptomycin (Jones et al., *Mol. Gen. Genet.*

210, 86 (1987)); and spectinomycin (Bretagne-Sagnard et al., *Transgenic Res.* 5, 131 (1996)); bleomycin (Hille et al., *Plant Mol. Biol.* 7, 171 (1986)); sulfonamide (Guerineau et al., *Plant Mol. Bio.* 15, 127 (1990); bromoxynil (Stalker et al., *Science* 242, 419 (1988)); 2,4-D (Streber et al., *Bio/Technology* 7, 811 (1989)); phosphinothricin (DeBlock et al., *EMBO J.* 6, 2513 (1987)); spectinomycin (Bretagne-Sagnard and Chupeau, *Transgenic Research* 5, 131 (1996)).

Other selectable marker genes include the pat gene (for bialaphos and phosphinothricin resistance), the ALS gene for imidazolinone resistance, the HPH or HYG gene for hygromycin resistance, the Hm1 gene for resistance to the Hc-toxin, and other selective agents used routinely and known to one of ordinary skill in the art. See generally, Yarranton, *Curr. Opin. Biotech.* 3, 506 (1992); Chistopherson et al., *Proc. Natl. Acad. Sci. USA* 89, 6314 (1992); Yao et al., *Cell* 71, 63 (1992); Reznikoff, *Mol. Microbiol.* 6, 2419 (1992); BARKLEY ET AL., THE OPERON 177-220 (1980); Hu et al., *Cell* 48, 555 (1987); Brown et al., *Cell* 49, 603 (1987); Figge et al., *Cell* 52, 713 (1988); Deuschle et al., *Proc. Natl. Acad. Sci. USA* 86, 5400 (1989); Fuerst et al., *Proc. Natl. Acad. Sci. USA* 86, 2549 (1989); Deuschle et al., *Science* 248, 480 (1990); Labow et al., *Mol. Cell. Biol.* 10, 3343 (1990); Zambretti et al., *Proc. Natl. Acad. Sci. USA* 89, 3952 (1992); Baim et al., *Proc. Natl. Acad. Sci. USA* 88, 5072 (1991); Wyborski et al., *Nuc. Acids Res.* 19, 4647 (1991); Hillenand-Wissman, *Topics in Mol. And. Struc. Biol.* 10, 143 (1989); Degenkolb et al., *Antimicrob. Agents Chemother.* 35, 1591 (1991); Kleinschnidt et al., *Biochemistry* 27, 1094 (1988); Gatz et al., *Plant J.* 2, 397 (1992); Gossen et al., *Proc. Natl. Acad. Sci. USA* 89, 5547 (1992); Oliva et al., *Antimicrob. Agents Chemother.* 36,913 (1992); HLAVKA ET AL., HANDBOOK OF EXPERIMENTAL PHARMACOLOGY 78 (1985); and Gill et al., *Nature* 334, 721 (1988). Such disclosures are herein incorporated by reference in their entireties.

The heterologous nucleotide sequence of interest can additionally be operably linked to a sequence that encodes a transit peptide that directs expression of an encoded polypeptide of interest to a particular cellular compartment. Transit peptides that target protein accumulation in higher plant cells to the chloroplast, mitochondrion, vacuole, nucleus, and the endoplasmic reticulum (for secretion outside of the cell) are known in the art. Transit peptides that target proteins to the endoplasmic reticulum are desirable for correct processing of secreted proteins. Targeting protein expression to the chloroplast (for example, using the transit peptide from the RubP carboxylase small subunit gene) has been shown to result in the accumulation of very high concentrations of recombinant protein in this organelle. The pea RubP carboxylase small subunit transit peptide sequence has been used to express and target mammalian genes in plants (U.S. Pat. Nos. 5,717,084 and 5,728,925 to Herrera-Estrella et al.). Alternatively, mammalian transit peptides can be used to target recombinant protein expression, for example, to the mitochondrion and endoplasmic reticulum. It has been demonstrated that plant cells recognize mammalian transit peptides that target endoplasmic reticulum (U.S. Pat. Nos. 5,202,422 and 5,639,947 to Hiatt et al.).

Further, the expression cassette can comprise a 5' leader sequence that acts to enhance expression (transcription, post-transcriptional processing and/or translation) of an operably associated heterologous sequence. Leader sequences are known in the art and include sequences from: picornavirus leaders, e.g., EMCV leader (Encephalomyocarditis 5' non-coding region; Elroy-Stein et al., *Proc. Natl. Acad. Sci. USA*, 86, 6126 (1989)).; potyvirus leaders, e.g., TEV leader (Tobacco Etch Virus; Allison et al., *Virology*, 154, 9 (1986)); human immunoglobulin heavy-chain binding protein (BiP; Macajak and Sarnow, *Nature* 353, 90 (1991)); untranslated leader from the coat protein mRNA of alfalfa mosaic virus (AMV RNA 4; Jobling and Gehrke, *Nature* 325, 622 (1987)); tobacco mosaic virus leader (TMV; Gallie, MOLECULAR BIOLOGY OF RNA, 237-56 (1989)); and maize chlorotic mottle virus leader (MCMV; Lommel et al., *Virology* 81, 382 (1991)). See also, Della-Cioppa et al., *Plant Physiology* 84, 965 (1987).

The heterologous nucleotide sequence(s) in the expression cassette can be any nucleotide sequence(s) of interest and can be obtained from prokaryotes or eukaryotes (e.g., bacteria, fungi, yeast, viruses, plants, mammals) or the nucleotide sequence can be synthesized in whole or in part. Further, the heterologous nucleotide sequence can encode a polypeptide or can be transcribed to produce a non-translated RNA (e.g., an antisense RNA, an RNAi molecule, and the like). In particular embodiments, the non-translated RNA can be expressed to improve an agronomic trait in the plant (e.g., drought resistance, heat resistance, salt resistance, disease resistance, insect and other pest resistance [e.g., a *Bacillus thuringiensis* endotoxin], herbicide resistance, and the like), to confer male sterility, to improve fertility and/or enhance nutritional quality (e.g., enzymes that enhance nutritional quality). The nucleotide sequence may further be used in the sense orientation to achieve suppression of endogenous plant genes, as is known by those skilled in the art (see, e.g., U.S. Pat. Nos. 5,283,184; 5,034,323; the disclosures of which are incorporated by reference herein in their entireties).

The heterologous nucleotide sequence can encode a polypeptide that imparts a desirable agronomic trait to the plant (as described above), confers male sterility, improves fertility and/or improves nutritional quality. Other suitable polypeptides include enzymes that can degrade organic pollutants or remove heavy metals. Such plants, and the enzymes that can be isolated therefrom, are useful in methods of environmental protection and remediation. Alternatively, the heterologous nucleotide sequence can encode a therapeutically or pharmaceutically useful polypeptide or an industrial polypeptide (e.g., an industrial enzyme). Such polypeptides include, but are not limited to antibodies and antibody fragments, cytokines, hormones, growth factors, receptors, enzymes and the like. In general, the heterologous nucleotide sequence can be any sequence other than the endogenous rubi3 coding sequence associated with the rubi3 promoter/intron in the naturally occurring rubi3 gene.

Heterologous nucleotide sequences suitable to confer tolerance to the herbicide glyphosate include, but are not limited to the *Agrobacterium* strain CP4 glyphosate resistant EPSPS gene (aroA:CP4) as described in U.S. Pat. No. 5,633,435 or the glyphosate oxidoreductase gene (GOX) as described in U.S. Pat. No. 5,463,175. Other heterologous nucleotide sequences include genes conferring resistance to herbicides that act to inhibit the action of acetolactate synthase (ALS), in particular the sulfonylurea-type herbicides (e.g., mutant forms of the acetolactate synthase (ALS) gene that lead to such resistance, in particular the S4 and/or Hra mutations), genes coding for resistance to herbicides that act to inhibit the action of glutamine synthase, such as phosphinothricin or basta (e.g., the bar gene). The bar gene encodes resistance to the herbicide basta, the nptII gene encodes resistance to the antibiotics kanamycin and geneticin, and the ALS gene encodes resistance to the herbicide chlorsulfuron.

Suitable heterologous nucleotide sequences that confer insect tolerance include those which provide resistance to pests such as rootworm, cutworm, European Corn Borer, and the like. Exemplary nucleotide sequences include, but are not limited to, a *Bacillus* insect control protein gene (see, e.g., WO 99/31248; U.S. Pat. Nos. 5,689,052; 5,500,365; 5,880,275); *Bacillus thuringiensis* toxic protein genes (see, e.g., U.S. Pat. Nos. 5,366,892; 5,747,450; 5,737,514; 5,723,756; 5,593,881; 6,555,655; 6,541,448; 6,538,109; Geiser, et al. (1986) *Gene* 48:109); and lectins (Van Damme et al. (1994) *Plant Mol. Biol.* 24:825).

Alternatively, the heterologous nucleotide sequence can encode a reporter polypeptide (e.g., an enzyme), including but not limited to Green Fluorescent Protein, β-galactosidase, luciferase, alkaline phosphatase, the GUS gene encoding β-glucuronidase, and chloramphenicol acetyltransferase.

Where appropriate, the heterologous nucleic acids may be optimized for increased expression in a transformed plant, e.g., by using plant preferred codons. Methods for synthetic optimization of nucleic acid sequences are available in the art. The nucleotide sequence can be optimized for expression in a particular host plant or alternatively can be modified for optimal expression in monocots. See, e.g., EP 0 359 472, EP 0 385 962, WO 91/16432; Perlak et al., *Proc. Natl. Acad. Sci. USA* 88, 3324 (1991), and Murray et al., *Nuc. Acids Res.* 17,477 (1989), and the like, herein incorporated by reference. Plant preferred codons can be determined from the codons of highest frequency in the proteins expressed in that plant.

Additional sequence modifications are known to enhance gene expression in a cellular host. These include elimination of sequences encoding spurious polyadenylation signals, exon-intron splice site signals, transposon-like repeats, and other such well-characterized sequences which may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures.

The invention further provides vectors comprising the nucleic acids and expression cassettes of the invention, including expression vectors, transformation vectors and vectors for replicating and/or manipulating the nucleotide sequences in the laboratory. The vector can be a plant vector, animal (e.g., insect or mammalian) vector, bacterial vector, yeast vector or fungal vector. Generally, according to the present invention, the vector is a plant vector, a bacterial vector, or a shuttle vector that can replicate in either host under appropriate conditions. Bacterial and plant vectors are well-known in the art. Exemplary plant vectors include plasmids (e.g., pUC or the Ti plasmid), cosmids, phage, bacterial artificial chromosomes (BACs), yeast artificial chromosomes (YACs) and plant viruses.

III. Methods Of Expressing A Nucleotide Sequence Of Interest.

The invention also provides methods of delivering a nucleic acid, expression cassette or vector of the invention to a target plant or plant cell (including callus cells or protoplasts), plant parts, seed, plant tissue (including callus), or the like. The invention further comprises host plants, cells, plant parts, seeds, tissue culture (including callus) transiently or stably transformed with the nucleic acids, expression cassettes or vectors of the invention.

As used herein, unless indicated otherwise, a "plant cell" includes callus cells and protoplasts. The term "plant tissue" includes callus tissue as well as tissue culture. Further, the term "tissue culture" encompasses cultures of tissue, cells, protoplasts and callus.

Plant parts, organs and tissues in which the rubi3 promoter may be useful in expressing a heterologous nucleotide sequence of interest include, but are not limited to reproductive tissues (e.g., petals, sepals, stamens, pistils, receptacles, anthers, pollen, flowers, fruits, flower bud, ovules, seeds, embryos, and nuts); vegetative tissues (e.g., petioles, stems, roots, root hairs, root tips, pith, coleoptiles, stalks, shoots, bark, apical meristem, axillary bud, cotyledon, hypocotyls, and leaves); vascular tissues (e.g., phloem and xylem); specialized cells such as epidermal cells, parenchyma cells, chollenchyma cells, schlerenchyma cells, stomates, guard cells, cuticle, mesophyll cells; callus tissue; and cuttings.

Any plant can be employed in practicing the present invention including angiosperms or gymnosperms, monocots or dicots. In particular embodiments, the plant is a monocot.

Exemplary plants include, but are not limited to corn (*Zea mays*), canola (*Brassica napus, Brassica rapa* ssp.), alfalfa (*Medicago saliva*), rice (*Oryza sativa*), rape (*Brassica napus*), rye (*Secale cereale*), sorghum (*Sorghum bicolor, Sorghum vulgare*), sunflower (*Helianthus annus*), wheat (*Triticum aestivum*), soybean (*Glycine max*), tobacco (*Nicotiana tobacum*), potato (*Solanum tuberosum*), peanuts (*Arachis hypogaea*), cotton (*Gossypium hirsutum*), sweet potato (*Ipomoea batatus*), cassaya (*Manihot esculenta*), coffee (*Cofea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), apple (*Malus pumila*), blackberry (*Rubus*), strawberry (*Fragaria*), walnut (*Juglans regia*), grape (*Vitis vinifera*), apricot (*Prunus armeniaca*), cherry (*Prunus*), peach (*Prunus persica*), plum (*Prunus domestica*), pear (*Pyrus communis*), watermelon (*Citrullus vulgaris*). duckweed (*Lemna*), oats, barley, vegetables, ornamentals, conifers, and turfgrasses (e.g., for ornamental, recreational or forage purposes).

Vegetables include Solanaceous species (e.g., tomatoes; *Lycopersicon esculentum*), lettuce (e.g., *Lactuea sativa*), carrots (*Caucus carota*), cauliflower (*Brassica oleracea*), celery (*apium graveolens*), eggplant (*Solanum melongena*), asparagus (*Asparagus officinalis*), ochra (*Abelmoschus esculentus*), green beans (*Phaseolus vulgaris*), lima beans (*Phaseolus limensis*), peas (*Lathyrus* spp.), members of the genus *Cucurbita* such as Hubbard squash (C. Hubbard), Butternut squash (*C. moschata*), Zucchini (*C. pepo*), Crookneck squash (C. crookneck), *C. argyrosperma, C. argyrosperma* ssp *sororia, C. digitata, C. ecuadorensis, C. foetidissima, C. lundelliana,* and *C. martinezii*, and members of the genus *Cucumis* such as cucumber (*Cucumis sativus*), cantaloupe (*C. cantalupensis*), and musk melon (*C. melo*).

Ornamentals include azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*dianthus caryophyllus*), poinsettia (*Euphorbia pulcherima*), and chrysanthemum.

Conifers, which may be employed in practicing the present invention, include, for example, pines such as loblolly pine (*Pinus taeda*), slash pine (*Pinus elliotii*), ponderosa pine (*Pinus ponderosa*), lodgepole pine (*Pinus contorta*), and Monterey pine (*Pinus radiata*); Douglas-fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*).

Turfgrass include but are not limited to zoysiagrasses, bentgrasses, fescue grasses, bluegrasses, St. Augustinegrasses, bermudagrasses, bufallograsses, ryegrasses, and orchardgrasses.

Also included are plants that serve primarily as laboratory models, e.g., *Arabidopsis*.

In particular embodiments, the invention is used to transform a monocotyledonous plant (or plant part, plant tissue, plant cell, callus, seed, etc.). Exemplary monocotyledonous species include corn (*Zea mays*); millet such as pearl millet (*Pennisetum glaucum*), proso millet (*Panicum miliaceum*), foxtail millet (*Setaria italica*), or finger millet (*Eleusine coracana*); rice (*Oryza sativa*); rye (*Secale cereale*); sorghum (*Sorghum bicolor, Sorghum vulgare*); wheat (*Triticum aestivum*); banana and plantain (*Musa* spp.); sugarcane (*Saccharum* spp.), duckweed (*Lemna*); oats; barley; turfgrasses as well as forage and biomass grasses.

In particular embodiments, the invention provides a method of producing a polypeptide of interest from a cell or tissue culture, wherein the cultured cells or tissue comprise an isolated nucleic acid, expression construct or vector (all as described above) according to the present invention. In one particular embodiment, the method comprises culturing a plant cell or tissue comprising an isolated nucleic acid, expression construct or vector according to the invention comprising a heterologous nucleotide sequence encoding a polypeptide of interest under conditions sufficient for the polypeptide of interest to be expressed by the cultured cells or tissue and, optionally, collecting the polypeptide. According to this embodiment, the polypeptide of interest can be a secreted polypeptide. The method can further comprise introducing the isolated nucleic acid, expression construct or vector of the invention into the cultured plant cell or tissue.

Methods of introducing nucleic acids, transiently or stably, into plants, plant tissues, cells, protoplasts, seed, callus and the like are known in the art. Stably transformed nucleic acids can be incorporated into the genome or stably maintained as episomes. Exemplary transformation methods include biological methods using viruses and *Agrobacterium*, physicochemical methods such as electroporation, floral dip methods, polyethylene glycol, ballistic bombardment, microinjection, and the like. Other transformation technology includes the whiskers technology that is based on mineral fibers (see e.g., U.S. Pat. Nos. 5,302,523 and 5,464,765) and pollen tube transformation.

In one form of direct transformation, the vector is microinjected directly into plant cells by use of micropipettes to mechanically transfer the recombinant DNA (Crossway, *Mol. Gen. Genetics* 202: 179 (1985)).

In another protocol, the genetic material is transferred into the plant cell using polyethylene glycol (Krens, et al. *Nature* 296, 72 (1982)).

In still another method, protoplasts are fused with minicells, cells, lysosomes, or other fusible lipid-surfaced bodies that contain the nucleotide sequence to be transferred to the plant (Fraley, et al., *Proc. Natl. Acad. Sci. USA* 79, 1859 (1982)).

Nucleic acids may also be introduced into the plant. cells by electroporation (Fromm et al., *Proc. Natl. Acad. Sci. USA* 82, 5824 (1985)). In this technique, plant protoplasts are electroporated in the presence of nucleic acids comprising the expression cassette. Electrical impulses of high field strength reversibly permeabilize biomembranes allowing the introduction of the nucleic acid. Electroporated plant protoplasts reform the cell wall, divide and regenerate. One advantage of electroporation is that large pieces of DNA, including artificial chromosomes, can be transformed by this method.

Ballistic transformation typically comprises the steps of: (a) providing a plant material as a target; (b) propelling a microprojectile carrying the heterologous nucleotide sequence at the plant target at a velocity sufficient to pierce the walls of the cells within the target and to deposit the nucleotide sequence within a cell of the target to thereby provide a transformed target. The method can further include the step of culturing the transformed target with a selection agent and, optionally, regeneration of a transformed plant. As noted below, the technique may be carried out with the nucleotide sequence as a precipitate (wet or freeze-dried) alone, in place of the aqueous solution containing the nucleotide sequence.

Any ballistic cell transformation apparatus can be used in practicing the present invention. Exemplary apparatus are disclosed by Sandford et al. (*Particulate Science and Technology* 5, 27 (1988)), Klein et al. (*Nature* 327, 70 (1987)), and in EP 0 270 356. Such apparatus have been used to transform maize cells (Klein et al., *Proc. Natl. Acad. Sci. USA* 85, 4305 (1988)), soybean callus (Christou et al., *Plant Physiol.* 87, 671 (1988)), McCabe et al., *BioTechnology* 6, 923 (1988), yeast mitochondria (Johnston et al., *Science* 240, 1538 (1988)), and *Chlamydomonas* chloroplasts (Boynton et al., *Science* 240, 1534 (1988)).

Alternately, an apparatus configured as described by Klein et al. (*Nature* 70, 327 (1987)) may be utilized. This apparatus comprises a bombardment chamber, which is divided into two separate compartments by an adjustable-height stopping plate. An acceleration tube is mounted on top of the bombardment chamber. A macroprojectile is propelled down the acceleration tube at the stopping plate by a gunpowder charge. The stopping plate has a borehole formed therein, which is smaller in diameter than the microprojectile. The macroprojectile carries the microprojectile(s), and the macroprojectile is aimed and fired at the borehole. When the macroprojectile is stopped by the stopping plate, the microprojectile(s) is propelled through the borehole. The target is positioned in the bombardment chamber so that a microprojectile(s) propelled through the bore hole penetrates the cell walls of the cells in the target and deposit the nucleotide sequence of interest carried thereon in the cells of the target. The bombardment chamber is partially evacuated prior to use to prevent atmospheric drag from unduly slowing the microprojectiles. The chamber is only partially evacuated so that the target tissue is not desiccated during bombardment. A vacuum of between about 400 to about 800 millimeters of mercury is suitable.

In alternate embodiments, ballistic transformation is achieved without use of microprojectiles. For example, an aqueous solution containing the nucleotide sequence of interest as a precipitate may be carried by the macroprojectile (e.g., by placing the aqueous solution directly on the plate-contact end of the macroprojectile without a microprojectile, where it is held by surface tension), and the solution alone propelled at the plant tissue target (e.g., by propelling the macroprojectile down the acceleration tube in the same manner as described above). Other approaches include placing the nucleic acid precipitate itself ("wet" precipitate) or a freeze-dried nucleotide precipitate directly on the plate-contact end of the macroprojectile without a microprojectile. In the absence of a microprojectile, it is believed that the nucleotide sequence must either be propelled at the tissue target at a greater velocity than that needed if carried by a microprojectile, or the nucleotide sequenced caused to travel a shorter distance to the target (or both).

It particular embodiments, the nucleotide sequence is delivered by a microprojectile. The microprojectile can be formed from any material having sufficient density and cohesiveness to be propelled through the cell wall, given the particle's velocity and the distance the particle must travel. Non-limiting examples of materials for making microprojectiles include metal, glass, silica, ice, polyethylene, polypropylene, polycarbonate, and carbon compounds (e.g., graphite, diamond). Non-limiting examples of suitable metals include tungsten, gold, and iridium. The particles should be of a size sufficiently small to avoid excessive disruption of the cells they contact in the target tissue, and sufficiently large to provide the inertia required to penetrate to the cell of interest in the target tissue. Particles ranging in diameter from about one-half micrometer to about three micrometers are suitable. Particles need not be spherical, as surface irregularities on the particles may enhance their carrying capacity.

The nucleotide sequence may be immobilized on the particle by precipitation. The precise precipitation parameters employed will vary depending upon factors such as the particle acceleration procedure employed, as is known in the art. The carrier particles may optionally be coated with an encapsulating agents such as polylysine to improve the stability of nucleotide sequences immobilized thereon, as discussed in EP 0 270 356 (column 8).

Alternatively, plants may be transformed using *Agrobacterium tumefaciens* or *Agrobacterium rhizogenes*. *Agrobacterium*-mediated nucleic acid transfer exploits the natural ability of *A. tumefaciens* and *A. rhizogenes* to transfer DNA into plant chromosomes. *Agrobacterium* is a plant pathogen that transfers a set of genes encoded in a region called T-DNA of the Ti and Ri plasmids of *A. tumefaciens* and *A. rhizogenes*, respectively, into plant cells. The typical result of transfer of the Ti plasmid is a tumorous growth called a crown gall in which the T-DNA is stably integrated into a host chromosome. Integration of the Ri plasmid into the host chromosomal DNA results in a condition known as "hairy root disease". The ability to cause disease in the host plant can be removed by deletion of the genes in the T-DNA without loss of DNA transfer and integration. The DNA to be transferred is attached to border sequences that define the end points of an integrated T-DNA.

Transfer by means of engineered *Agrobacterium* strains has become routine for many dicotyledonous plants. Some difficulty has been experienced, however, in using *Agrobacterium* to transform monocotyledonous plants, in particular, cereal plants. However, *Agrobacterium* mediated transformation has been achieved in several monocot species, including cereal species such as rye, maize (Rhodes et al., *Science* 240, 204 (1988)), and rice (Hiei et al., (1994) Plant J. 6:271).

While the following discussion will focus on using *A. tumefaciens* to achieve gene transfer in plants, those skilled in the art will appreciate that this discussion also applies to *A. rhizogenes*. Transformation using *A. rhizogenes* has developed analogously to that of *A. tumefaciens* and has been successfully utilized to transform, for example, alfalfa, *Solanum nigrum* L., and poplar (U.S. Pat. No. 5,777,200 to Ryals et al.). As described by U.S. Pat. No. 5,773,693 to Burgess et al., it is preferable to use a disarmed *A. tumefaciens* strain (as described below), however, the wild-type *A. rhizogenes* may be employed. An illustrative strain of *A. rhizogenes* is strain 15834.

In particular protocols, the *Agrobacterium* strain is modified to contain the nucleotide sequences to be transferred to the plant. The nucleotide sequence to be transferred is incorporated into the T-region and is typically flanked by at least one T-DNA border sequence, optionally two T-DNA border sequences. A variety of *Agrobacterium* strains are known in the art particularly, and can be used in the methods of the invention. See, e.g., Hooykaas, *Plant Mol. Biol.* 13, 327 (1989); Smith et al., *Crop Science* 35, 301 (1995); Chilton, *Proc. Natl. Acad. Sci. USA* 90, 3119 (1993); Mollony et al., *Monograph Theor. Appl. Genet NY* 19, 148 (1993); Ishida et al., *Nature Biotechnol.* 14, 745 (1996); and Komari et al., *The Plant Journal* 10, 165 (1996), the disclosures of which are incorporated herein by reference.

In addition to the T-region, the Ti (or R1) plasmid contains a vir region. The vir region is important for efficient transformation, and appears to be species-specific.

Two exemplary classes of recombinant Ti and Ri plasmid vector systems are commonly used in the art. In one class, called "cointegrate," the shuttle vector containing the gene of interest is inserted by genetic recombination into a non-oncogenic Ti plasmid that contains both the cis-acting and trans-acting elements required for plant transformation as, for example, in the PMLJ1 shuttle vector of DeBlock et al., *EMBO J.* 3, 1681 (1984), and the non-oncogenic Ti plasmid pGV2850 described by Zambryski et al., *EMBO J.* 2, 2143 (1983). In the second class or "binary" system, the gene of interest is inserted into a shuttle vector containing the cis-acting elements required for plant transformation. The other necessary functions are provided in trans by the non-oncogenic Ti plasmid as exemplified by the pBIN19 shuttle vector described by Bevan, *Nucleic Acids Research* 12, 8711 (1984), and the non-oncogenic Ti plasmid PAL4404 described by Hoekma, et al., *Nature* 303,179 (1983).

Binary vector systems have been developed where the manipulated disarmed T-DNA carrying the heterologous nucleotide sequence of interest and the vir functions are present on separate plasmids. In this manner, a modified T-DNA region comprising foreign DNA (the nucleic acid to be transferred) is constructed in a small plasmid that replicates in *E. coli*. This plasmid is transferred conjugatively in a tri-parental mating or via electroporation into *A. tumefaciens* that contains a compatible plasmid with virulence gene sequences. The vir functions are supplied in trans to transfer the T-DNA into the plant genome. Such binary vectors are useful in the practice of the present invention.

In particular embodiments of the invention, super-binary vectors are employed. See, e.g., U.S. Pat. No. 5,591,615 and EP 0 604 662, herein incorporated by reference. Such a super-binary vector has been constructed containing a DNA region originating from the hypervirulence region of the Ti plasmid pTiBo542 (Jin et al., *J. Bacteriol.* 169, 4417 (1987)) contained in a super-virulent *A. tumefaciens* A281 exhibiting extremely high transformation efficiency (Hood et al., *Biotechnol.* 2, 702 (1984); Hood et al., *J. Bacteriol.* 168, 1283 (1986); Komari et al., *J. Bacteriol.* 166, 88 (1986); Jin et al., *J. Bacteriol.* 169, 4417 (1987); Komari, *Plant Science* 60, 223 (1987); ATCC Accession No. 37394.

Exemplary super-binary vectors known to those skilled in the art include pTOK162 (Japanese patent Appl. (Kokai) No. 4-222527, EP 504,869, EP 604,662, and U.S. Pat. No. 5,591, 616, herein incorporated by reference) and pTOK233 (Komari, *Plant Cell Reports* 9, 303 (1990); Ishida et al., *Nature Biotechnology* 14, 745 (1996); herein incorporated by reference). Other super-binary vectors may be constructed by the methods set forth in the above references. Super-binary vector pTOK162 is capable of replication in both *E. coli* and in *A. tumefaciens*. Additionally, the vector contains the virB, virC and virG genes from the virulence region of pTiBo542. The plasmid also contains an antibiotic resistance gene, a selectable marker gene, and the nucleic acid of interest to be transformed into the plant. The nucleic acid to be inserted into the plant genome is typically located between the two border sequences of the T region. Super-binary vectors of the invention can be constructed having the features described above for pTOK162. The T-region of the super-binary vectors and other vectors for use in the invention are constructed to have restriction sites for the insertion of the genes to be delivered. Alternatively, the DNA to be transformed can be inserted in the T-DNA region of the vector by utilizing in vivo homologous recombination. See, Herrera-Esterella et al., *EMBO J.* 2, 987 (1983); Horch et al., *Science* 223, 496 (1984). Such homologous recombination relies on the fact that the super-binary vector has a region homologous with a region of pBR322 or other similar plasmids. Thus, when the two plasmids are brought together, a desired gene is inserted into the super-binary vector by genetic recombination via the homologous regions.

In plants stably transformed by *Agrobacteria*-mediated transformation, the nucleotide sequence of interest is incorporated into the plant nuclear genome, typically flanked by at least one T-DNA border sequence and generally two T-DNA border sequences.

Plant cells may be transformed with *Agrobacteria* by any means known in the art, e.g., by co-cultivation with cultured isolated protoplasts, or transformation of intact cells or tissues. The first uses an established culture system that allows for culturing protoplasts and subsequent plant regeneration from cultured protoplasts. Identification of transformed cells or plants is generally accomplished by including a selectable marker in the transforming vector, or by obtaining evidence of successful bacterial infection.

Protoplasts, which have been transformed by any method known in the art, can also be regenerated to produce intact plants using known techniques.

Plant regeneration from cultured protoplasts is described in Evans et al., *Handbook of Plant Cell Cultures*, Vol. 1: (MacMilan Publishing Co. New York, 1983); and Vasil I. R. (ed.), *Cell Culture and Somatic Cell Genetics of Plants*, Acad. Press, Orlando, Vol. I, 1984, and Vol. II, 1986). Essentially all plant species can be regenerated from cultured cells or tissues, including but not limited to, all major species of sugarcane, sugar beet, cotton, fruit trees, and legumes.

Means for regeneration vary from species to species of plants, but generally a suspension of transformed protoplasts or a petri plate containing transformed explants is first provided. Callus tissue is formed and shoots may be induced from callus and subsequently root. Alternatively, somatic embryo formation can be induced in the callus tissue. These somatic embryos germinate as natural embryos to form plants. The culture media will generally contain various amino acids and plant hormones, such as auxin and cytokinins. It is also advantageous to add glutamic acid and proline to the medium, especially for such species as corn and alfalfa. Efficient regeneration will depend on the medium, on the genotype, and on the history of the culture. If these three variables are controlled, then regeneration is usually reproducible and repeatable.

The regenerated plants are transferred to standard soil conditions and cultivated in a conventional manner. The plants are grown and harvested using conventional procedures.

Alternatively, transgenic plants may be produced using the floral dip method (See, e.g., Clough and Bent (1998) *Plant Journal* 16:735-743, which avoids the need for plant tissue culture or regeneration. In one representative protocol, plants are grown in soil until the primary inflorescence is about 10 cm tall. The primary inflorescence is cut to induce the emergence of multiple secondary inflorescences. The inflorescences of these plants are typically dipped in a suspension of *Agrobacterium* containing the vector of interest, a simple sugar (e.g., sucrose) and surfactant. After the dipping process, the plants are grown to maturity and the seeds are harvested. Transgenic seeds from these treated plants can be selected by germination under selective pressure (e.g., using the chemical bialaphos). Transgenic plants containing the selectable marker survive treatment and can be transplanted to individual pots for subsequent analysis. See Bechtold, N. and Pelletier, G. Methods Mol Biol 82, 259-266 (1998); Chung, M. H. et al. Transgenic Res 9, 471-476 (2000); Clough, S. J. and Bent, A. F. Plant J 16, 735-743 (1998); Mysore, K. S. et al. Plant J 21, 9-16 (2000); Tague, B. W. Transgenic Res 10, 259-267 (2001); Wang, W. C. et al. Plant Cell Rep 22, 274-281 (2003); Ye, G. N. et al. Plant J., 19:249-257 (1999).

The particular conditions for transformation, selection and regeneration can be optimized by those of skill in the art. Factors that affect the efficiency of transformation include the species of plant, the target tissue or cell, composition of the culture media, selectable marker genes, kinds of vectors, and light/dark conditions. Therefore, these and other factors may be varied to determine what is an optimal transformation protocol for any particular plant species. It is recognized that not every species will react in the same manner to the transformation conditions and may require a slightly different modification of the protocols disclosed herein. However, by altering each of the variables, an optimum protocol can be derived for any plant species.

Having described the present invention, the same will be explained in greater detail in the following examples, which are included herein for illustration purposes only, and which are not intended to be limiting to the invention.

EXAMPLE 1

Plant Material

Rice seeds (cv. Nipponbare) were obtained from the National Small Grains Collection (USDA-ARS, Aberdeen, Id.). Eighteen-month-old fine rice suspension cells derived from primary calli raised from mature seeds were maintained in 125 ml flasks containing 50 ml of AA medium (Müller and Grafe (1978) *Mol. Gen. Genet.* 161:67-76) on a gyratory shaker (125 rpm). Cultures were grown in the dark at 25° C. and subcultured once a week.

EXAMPLE 2

Isolation of Rubi3 Sequences

A rice genome sequence database was used in the BLAST search for polyubiquitin gene sequences. The genomic sequence for rubi3 was identified in BAC clone OSM14960/14965 (Monsanto, St. Louis, Mo.).

Genomic DNA from rice leaves was isolated using well-established methods (Dellaporta, et al., (1983) *Plant Mol. Biol. Rep.* 14:19-21). The 5' flanking region of rubi3 containing the promoter region plus rubi3 intron (SEQ ID NO:1; FIG. 1A), rubi3 promoter alone (SEQ ID NO:2; FIG. 1B) and rubi3 intron alone (SEQ ID NO:3; FIG. 1C) were amplified using the following primers: 4-5'-GTC GAC CAC CCA ACC CCA TAT CGA CAG AGG-3' (SEQ ID NO:4); UR7sma-5'-CCC GGG CTG GAA GAG GCA AGA AAG GAT TGG AAT TAA C-3' (SEQ ID NO:5); 2sma-5'-CCC GGG TAA CTA ATC AAT CAC CTC GT-3' (SEQ ID NO:6); UR8-5'-CTT GAC GAG GCG ATT AGA GAA CGC-3' (SEQ ID NO:7).

The rubi3 gene (SEQ ID NO:8) contained an open reading frame of 1146-bp, arranged as five tandem, head-to-tail repeats of 228-bp, encoding a pentameric precursor ubiquitin (FIGS. 2A and 2B). The deduced amino acid sequence of the five ubiquitin monomers of rubi3 (SEQ ID NO:9) was identical to ubiquitin sequences of maize and *A. thaliana*.

EXAMPLE 3

Characterization of the rubi3 Gene

The coding sequence of the rubi3 ubiquitin gene shared a high degree of homology with ubiquitin genes from *Arabidopsis* (Burke, et al. (1988) supra; Callis, et al (1995) *Genetics* 139:921-939), sunflower (Binet, et al. (1991) supra), potato (Garbarino and Belknap (1994) supra), tomato (Hoffman, et al. (1991) *Plant Mol. Biol.* 17:1189-1201), *N. tobacum* (Genschik, et al. (1994) supra), sugarcane (Albert, et al. (1995) *Plant Physiol.* 109:337) and yeast (Ozkaynak, et al. (1987) *EMBO J.* 6:1427-1439). For example, the coding sequence of the rubi3 gene showed 84% identity to the maize polyubiquitin gene (Genbank accession number S94464), 79% to the *A. thaliana* ubiquitin gene (accession number U84968), 80% to the sunflower ubiquitin gene (accession number X57004), 86% to the rice RUBQ1 (accession number AF184279), 86% to the rice RUBQ2 (accession number AF184280) and 85% to the rice RUBI1 (accession number U37687).

An intron was identified at the 5' untranslated region (5' UTR) immediately upstream of the ATG translation initiation codon for the rubi3 gene (FIG. 2A). the presence of the intron and the precise splice sites for rubi3 were confirmed by comparison of rubi3 genomic and cDNA sequences. The rubi3 intron was 1140 bp long and did not have significant homology with known maize or rice ubiquitin introns (FIGS. 3A-3C) or any other sequences. Intron splice sites of rubi3 are in good agreement with the consensus sequences CAAG/gta at the 5' end and cag/ATG at the 3' end, which are common to plant polyubiquitin genes (Binet, et al. (1991) supra; Christensen, et al. (1992) supra; Kawalleck, et al. (1993) supra; Norris, et al. (1993) *Plant Mol. Biol.* 21:895-906).

A heat shock sequence similar to the *Drosophila* consensus sequence 5'-CTGGAATnTTCTAGA-3' (SEQ ID NO:10) (Pelham (1982) *Cell* 30:517-528), is generally present in the isolated ubiquitin promoters (Christensen, et al. (1992) supra; Wang, et al. (2000) *Plant Sci.* 156(2):201-211). Such a consensus sequence was not observed in the rubi3 promoter sequence. An enhancer core consensus sequence 5'-GGT-GTGG(AAA/TTT)G-3' (SEQ ID NO:11) (Weiher, et al. (1983) *Science* 219:626-631; Khoury and Gruss (1983) *Cell* 33:313-314) is observed in RUBQ1 and RUBQ2 promoter sequences (Wang et al. (2000) supra); however, this sequence was not observed in the rubi3 promoter sequence (FIG. 2A).

EXAMPLE 4

RT-PCR

Reverse transcription (RT)-coupled PCR reactions were performed to obtain the cDNA encoding rubi3 and to confirm the predicted intron and splice sites. Two primers were synthesized to encompass the rubi3 coding sequence and 5'- and 3'-UTR sequences. These primers were: Intron1, 5'-CGA ATC GAC CGA AGG GGA GG-3' (SEQ ID NO:12) and 5'Race-3,5'-ACA CGA TGA TAT GAC AGA CGA GC-3' (SEQ ID NO:13).

Total RNA was prepared using the method of Haffner, et al. ((1978) *Can. J. Biochem.* 56:729-733). RT reactions were performed using SUPERSCRIPT™ II reverse transcriptase (INVITROGEN™ Corp., Carlsbad, Calif.) followed by standard PCR reactions using Taq DNA polymease (EPPENDORF®, Westbury, N.Y.). Conditions for RT-PCR reactions were in accordance with manufacturer's recommendations.

EXAMPLE 5

Chimeric Gene Constructs

A 2-kb PCR product encompassing the rubi3 promoter and rubi3 5' UTR intron was amplified with primers 4 and UR7sma and cloned into the pCR®2.1 to generate pRESQ21. The sequence and orientation of the 2-kb fragment were confirmed and the 2-kb SpeI/SmaI fragment was cloned into XbaI/SmaI-digested pRESQ8, a pUC119-based vector containing a β-glucuronidase gene (GUS) and a NOS terminator. The resulting plasmid, pRESQ4 (FIG. 4A), harbored the rubi3 promoter, intron, GUS and NOS terminator.

The rubi3 promoter, a 875-bp PCR product obtained using primers 4 and UR8, was cloned into pCR®2.1 to generate pRESQ32. A 0.9-kb BamHI/EcoRV fragment of pRESQ32 encompassing the rubi3 promoter was liberated and ligated into BamHI/SmaI-digested pRESQ8 to create pRESQ33 (FIG. 4B) which harbored the rubi3 promoter, GUS and NOS.

The rubi3 intron, a 1.1-kb PCR product obtained using primers 2sma and UR7sma, was cloned into pCR®2.1 to generate pRESQ13. A 1.1-kb SmaI fragment of pRESQ13 encompassing the rubi3 intron was liberated and ligated into SmaI-digested pRESQ8 to create pRESQ18 (FIG. 4C) which harbored the rubi3 intron, GUS and NOS.

The 1.1-kb SmaI fragment of pRESQ18 was liberated and ligated in the SmaI site of pRQ202 which encompasses an intronless rice Actin1D promoter, GUS and NOS. The resulting plasmid, designated pRESQ17 (FIG. 4D), contained an intronless rice Actin1D promoter, rubi3 intron, GUS and NOS.

A 3.8-kb HindIII cassette containing the maize ubi promoter, GUS and NOS was liberated from pAHC25 (Christensen and Quail (1996) *Transgenic Res.* 5:213-218) and ligated into HindIII-digested pUC119 to create pRESQ29. This construct along with pRQ6, which contains the cauliflower mosaic virus CaMV 35S promoter, GUS and NOS, and pAct1D, which contains the rice actin promoter, GUS and NOS, were used as controls.

EXAMPLE 6

Transient GUS Assays

The chimeric gene constructs provided herein were used in the transformation of rice suspension cells via particle bombardment, with appropriate controls.

Approximately 200 mg of rice suspension cells (cv. Nipponbare) were evenly distributed over the surface of a 15 mm Whatman no. 2 filter paper in a 100×15 mm² petri dish for particle bombardment. Plasmids were coated onto gold particles (1.0 μm in diameter; BIO-RAD®, Hercules, Calif.) and introduced into suspension cells via particle bombardment according to the method described by Christou, et al. (1991) *BioTechnology* 9:957-962). Equal molar amounts of each construct containing the chimeric GUS gene were transformed into suspension cells with three replications. After a 24-hour incubation at 25° C., cells were transferred into a microfuge tube and homogenized with 400 μL GUS extraction buffer (Jefferson (1987) *Plant Mol. Biol. Rep.* 5:387-405). Cell homogenates were centrifuged at 10,000×g for 5 minutes at 4° C. and the supernatant was collected and assayed.

GUS enzyme assays were performed using 20 µL of supernatant in accordance with well-established methods (Jefferson (1987) supra; Gallagher (1992) In: GUS protocols: using the GUS gene as a reporter of gene expression. S. R. Gallagher ed. Academic Press Inc. pp 47-59) in a FLUO-star BMG fluorometer (BMG Lab Technologies, Durham, N.C.). GUS activity was expressed as µmol MU (4 methylumbelliferone)/min/mg total protein. Simultaneously, histochemical GUS assays (Jefferson (1987) supra) were also performed.

Figure 5A:
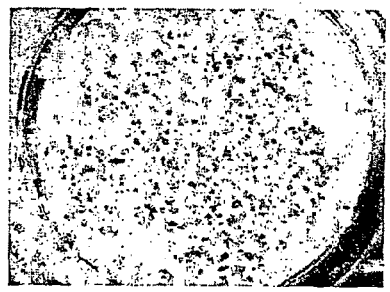
FIG. 5A shows transient GUS activity in rice suspension cells transformed with pRESQ4 which contains the rubi3 promoter and rubi3 intron driving GUS gene expression.
Figure 5B:
FIG. 5B shows transient GUS activity in rice coleoptiles transformed with pRESQ4 which contains the rubi3 promoter and rubi3 intron driving GUS gene expression (left), and with pRESQ17 which contains the rice actin promoter and rubi3 intron driving GUS gene expression (right), respectively.

Chimeric gene constructs containing the rubi3 promoter sequence driving expression of GUS where introduced into rice suspension cells (FIG. 5A) and coleoptiles (FIG. 5B). A significant number of blue spots were observed as compared with control samples (FIGS. 5A and 5B).

Figure 4B:
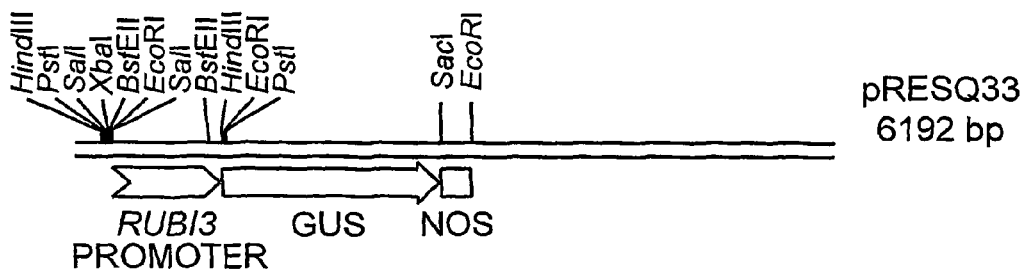
Figure 4C:
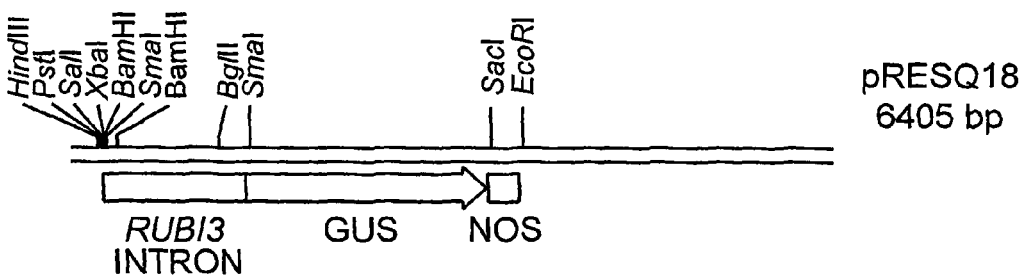
Figure 4D:
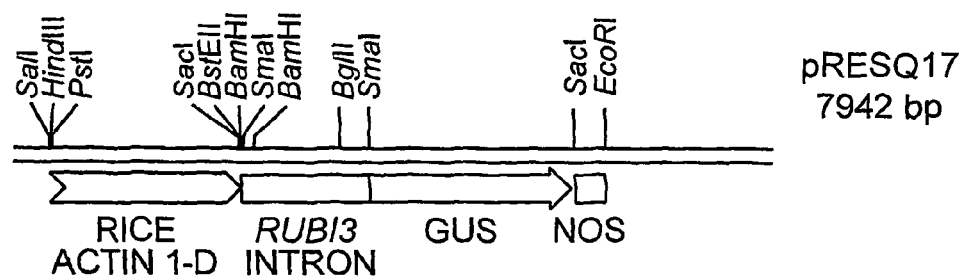

The activity of the rubi3 promoter and the effect of the rubi3 intron on gene expression were analyzed. FIGS. 4A-4C show schematic features of chimeric genes containing the rubi3 promoter. These constructs were introduced into rice suspension cells via particle bombardment. GUS activity (pmol MU/min/mg total protein) was determined and the relative values across multiple independent experiments were consistent. The quantitative MUG assays and the histochemical assays provided similar results.

When compared with other commonly used promoters, the rubi3 promoter with the rubi3 intron exhibited more than a 10-fold higher level of activity than the CaMV 35S promoter, 30% lower than the maize ubi1 promoter, and nearly a 50% lower level of expression than the rice Act1 promoter (Table 1; FIG. 6). However, the expression of rice Act1D construct may have been positively affected by the first six amino acid residues of the Act1 coding region which was fused to the GUS gene.

The rubi3 intron had a significant, positive effect on GUS reporter gene expression. A 20-fold higher level of expression was observed from constructs containing the rubi3 intron (pRESQ4) as compared to constructs lacking the rubi3 intron (pRESQ33) (Table 1; FIG. 6). Moreover, when the rubi3 intron was placed downstream of the rice actin promoter which lacked its own intron (pRESQ17), the enhancement of transient GUS activity was nearly 18-fold more than that of an intronless Act1 promoter construct (pRQ202). These results indicate that the rubi3 intron enhances the activity of other unrelated promoters.

In other studies, expression from the rice H3 promoter isolated by the inventors' laboratory was enhanced by 21-fold by the rubi3 intron (data not shown).

TABLE 1

| Plasmid construct | Promoter | Transient GUS activity µMoles MU/min/mg total protein* |
|---|---|---|
| pRESQ4 | rubi3 with the rubi3 intron | 14.74 |
| pRESQ33 | rubi3 without an intron | 0.74 |
| pRQ202 | Rice Act1 without an intron | 1.18 |
| pRESQ17 | Rice Act 1 with the rubi3 intron | 20.88 |
| pAct1D | Rice Act1 with the Act1 intron | 27.25 |
| pRESQ29 | Maize ubi1 with the ubi1 intron | 21.35 |
| pRQ6 | CaMV 35S | 1.35 |
| Control | | 0.63 |

*Values represent the mean of three independent bombardments of rice suspension cells

EXAMPLE 7

Rubi3 Promoter Activity Enhancement

To further enhance the levels of expression of proteins fused to rubi3 regulatory regions, three constructs were generated which fused the coding sequence of a full monomer, first nine amino acids, or first three amino acids of the rubi3 gene in-frame with nucleic acid sequences encoding GUS. Using standard cloning and three-primer PCR techniques (Yon and Fried (1989) Nucl. Acid Res. 17(12):4895), precise translational fusions were generated. All fusions were verified by DNA sequence analysis. The resulting constructs were designated pRESQ 38 encoding a translational fusion between GUS and the first monomer of RUBI3, pRESQ36 encoding a translational fusion between GUS and the first nine amino acids of RUBI3, and pRESQ 42 encoding a translational fusion between GUS and the first three amino acids of RUBI3.

The constructs were tested in rice callus lines via transient GUS assays. Rice suspension cells (cv. Nipponbare) were bombarded in triplicates and repeated at least once with respective plasmid constructs. Transformation through biolistic bombardment and transient MUG assays were performed as described herein.

Figure 8:
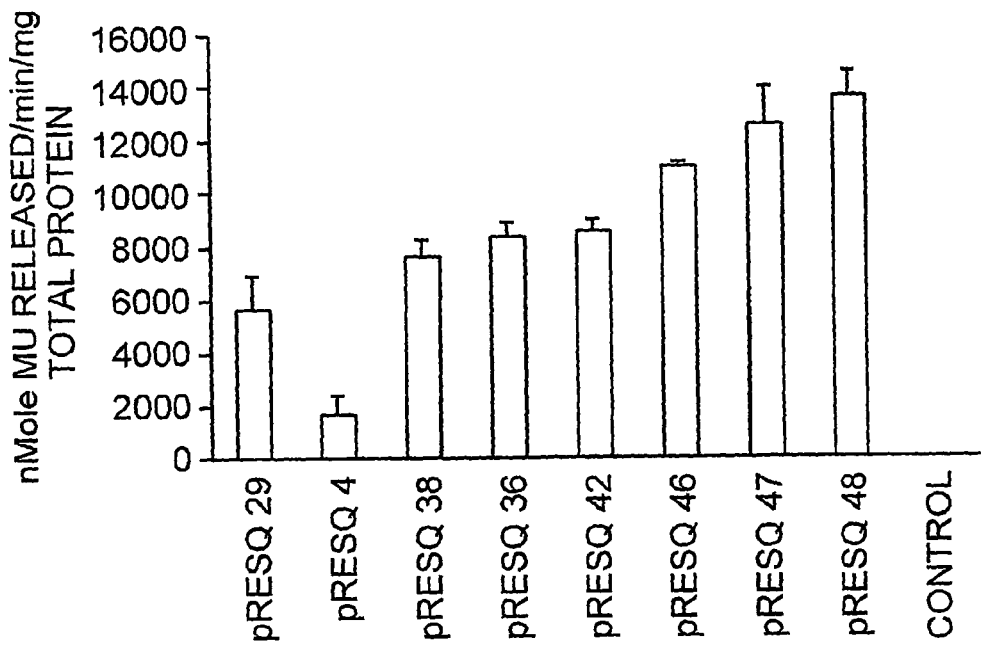
FIG. 8 shows transient GUS activity in rice suspension cells transformed with rubi3::GUS fusion constructs. pRESQ29, maize ubi; pRESQ38, translational fusion of the first monomer of rubi3 with GUS; pRESQ36, translational fusion of the first 9 amino acids of rubi3 with GUS; pRESQ42, translational fusion of the first 3 amino acids of rubi3 with GUS; and pRESQ46, pRESQ47 and pRESq48, non-translated fusion of the first 9 nucleotides of rubi3 with GUS, wherein the G of the initiation codon of rubi3 is mutated from G to A (PRESQ 46), G to T (pRESQ 47), or G to C (pRESQ48).

The results of these experiments indicated that fusions proteins between rubi3 and GUS enhanced the activity of GUS by 4- to 4.5-fold, with the three amino acid fusion construct being the highest (about 1.5-fold of a maize ubi1-GUS construct)(FIG. 8). Thus, the first nine nucleotides of the rubi3 coding sequence (ATGCAGATA) are sufficient for enhancing the expression of transgenes from rubi3 regulatory sequences.

To maintain a high level of expression and eliminate the additional amino acids at the N-terminus of a transgene of interest, the third nucleotide of the initiation codon of rubi3 was mutated to disrupt translation initiation from the rubi3 coding sequence, i.e., so that translation starts from the ATG codon of the transgene of interest. Accordingly, the G of the rubi3 initiation codon was mutated to A, T, or C (FIG. 7). Using standard methods, site-directed mutagenesis of the third nucleotide of the initiation codon in the first 9 nucleotides of the rubi3 coding sequence (ATGCAGATA) and fusion with GUS was carried out by PCR using vector pRESQ42 as a template (FIG. 7). The resulting vectors were designated pRESQ46 which contained a G to A substitution, pRESQ47 which contained a G to T substitution, and pRESQ48 which contained a G to C substitution (FIG. 7). All the mutations were verified by DNA sequence analysis.

Unexpectedly, these mutations further enhanced GUS activity by 20-50% over the three amino acid fusion construct (pRESQ42)(FIG. 8). The G to C mutation generated the highest level of expression; about 8-fold higher than the original rubi3 promoter containing the 5' UTR intron (pRESQ4), and approximately 2.5-fold of the maize ubi1 promoter (pRESQ29)(FIG. 8). These results also indicate that the first nine nucleotides of the rubi3 coding sequence (ATGCAGATA) function as a downstream factor (with its 5' UTR or other regulatory 5' UTR) to enhance rubi3 promoter activity.

EXAMPLE 8

Rubi3 Intron Deletion Mutant

Figure 4E:
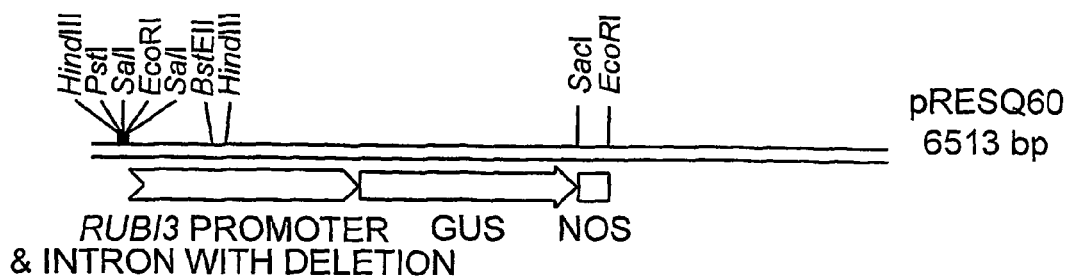
Figure 9:
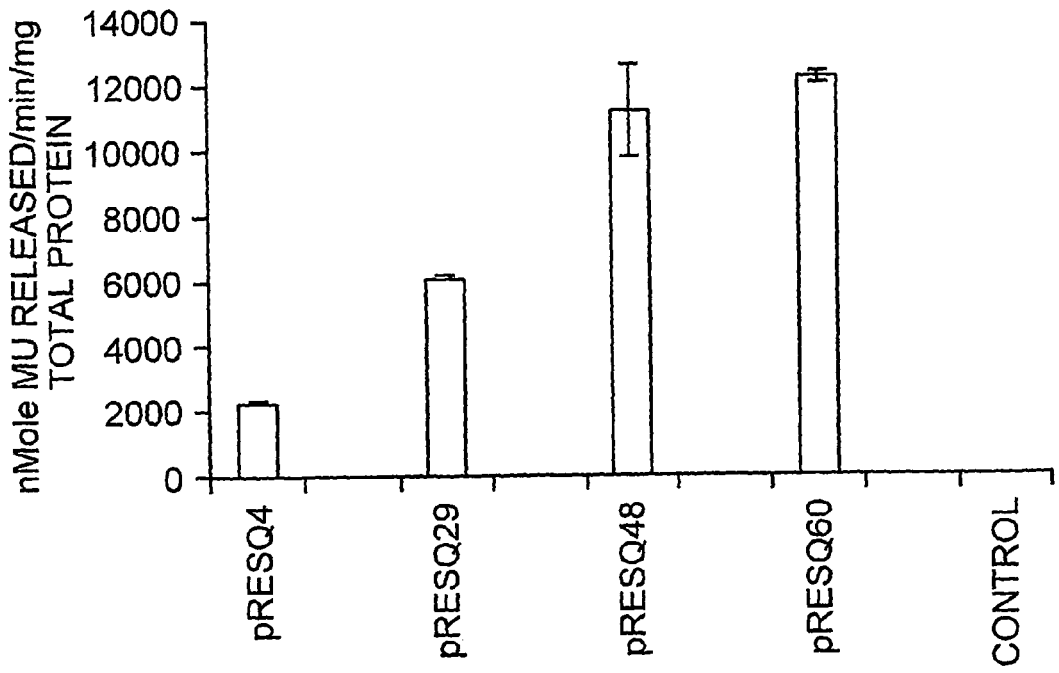
FIG. 9 demonstrates transient GUS expression in rice callus lines transformed with plasmids containing modified rubi3 promoter. The plasmid construct pRESQ48 was made by fusing 9 nucleotides encoding the first 3 amino acids of the rubi3 gene, where the third nucleotide (G) is replaced with a C. The plasmid construct pRESQ60 was made by deleting nucleotide sequences between BamHI and BglII restriction enzyme sites in the 5' UTR of the rubi3 intron sequence in pRESQ48. The plasmid pRESQ4 contains the un-altered rubi3 promoter, and plasmid pRESQ29 contains maize ubi1 promoter sequence driving the GUS gene.

To further define sequences involved in enhanced gene expression from the rubi3 intron, approximately 800 bp from the middle of the rubi3 intron were deleted. To generate this deletion mutant, plasmid pRESQ48 was restricted with BamHI, which cuts the intron at nucleotide 969 of FIG. 1A, and BglII, which cuts the intron at nucleotide 1755 of FIG. 1A; treated with Klenow enzyme to blunt the ends and ligated to obtain pRESQ60 which lacked about 780 bases in the rubi3 intron (FIG. 4E). The resulting promoter sequence of pRESQ60 is depicted in FIG. 1H. Unexpectedly, transient GUS activity of pRESQ60 was comparable, if not higher, than that of pRESQ48 in rice suspension cells (FIG. 9).

The foregoing is illustrative of the present invention, and is not to be construed as limiting thereof. The invention is defined by the following claims, with equivalents of the claims to be included therein.

That which is claimed is:

1. An isolated expression cassette comprising a nucleic acid having a nucleotide sequence selected from the group consisting of:
   (a) the nucleotide sequence of SEQ ID NO:1; and
   (b) a nucleotide sequence having at least 98% sequence identity to the nucleotide sequence of (a);
   wherein said nucleotide sequence selected from the group consisting of (a) and (b) has promoter activity, and further wherein:
   (i) said nucleotide sequence selected from the group consisting of (a) and (b) is operably linked with a heterologous nucleotide sequence of interest; or
   (ii) said expression cassette further comprises a plurality of restriction sites for insertion of a heterologous nucleotide sequence of interest to be operably linked to said nucleotide sequence selected from the group consisting of (a) and (b).

2. The isolated expression cassette of claim 1, wherein said nucleic acid has the nucleotide sequence of SEQ ID NO:1.

3. The expression cassette of claim 1, wherein said nucleotide sequence selected from the group consisting of (a) and (b) is operably linked with a heterologous nucleotide sequence of interest, as set forth in part (i).

4. The expression cassette of claim 3, wherein said heterologous nucleotide sequence of interest encodes a polypeptide.

5. The expression cassette of claim 3, wherein said heterologous nucleotide sequence of interest can be transcribed to produce an antisense RNA or RNAi.

6. The expression cassette of claim 1, wherein said expression cassette further comprises a nucleotide sequence that encodes a selectable marker.

7. A vector comprising the expression cassette of claim 1.

8. A cell comprising the expression cassette of claim 1.

9. The cell of claim 8, wherein the cell is a plant cell.

10. The cell of claim 9, wherein the expression cassette is stably incorporated into the genome of the plant cell.

11. A cell comprising the expression cassette of claim 3.

12. The cell of claim 11, wherein the cell is a plant cell.

13. The cell of claim 12, wherein the expression cassette is stably incorporated into the genome of the plant cell.

14. A cell comprising the vector of claim 7.

15. The cell of claim 14, wherein the cell is a plant cell.

16. A plant comprising the plant cell of claim 9.

17. A plant comprising the plant cell of claim 12.

18. A plant comprising the plant cell of claim 15.

19. A plant comprising the expression cassette of claim 3 stably incorporated into its genome.

20. The plant of claim 19, wherein the plant is a monocotyledonous plant.

21. A crop comprising a plurality of the plant of claim 19.

22. A seed comprising the expression cassette of claim 3 stably incorporated in its genome.

23. A method of introducing a nucleic acid into a plant or plant cell comprising transforming said plant or plant cell with the expression cassette of claim 1.

24. The method of claim 23, wherein the plant or plant cell is a monocotyledonous plant or plant cell.

25. The method of claim 23, wherein the heterologous nucleotide sequence of interest encodes a polypeptide.

26. The method of claim 25, further comprising the step of collecting the polypeptide.

27. The method of claim 23, wherein the heterologous nucleotide sequence of interest is transcribed to produce an antisense RNA or RNAi.

28. The method of claim 23, wherein the method comprises stably transforming the plant or plant cell with the expression cassette.

29. A method of expressing a nucleotide sequence in a plant or plant cell comprising transforming said plant or plant cell with the expression cassette of claim 3, and expressing the heterologous nucleotide sequence of interest in the plant or plant cell.

30. The method of claim 29, wherein the plant or plant cell is a monocotyledonous plant or plant cell.

31. The method of claim 29, wherein the heterologous nucleotide sequence of interest encodes a polypeptide.

32. The method of claim 31, further comprising the step of collecting the polypeptide.

33. The method of claim 29, wherein the heterologous nucleotide sequence of interest is transcribed to produce an antisense RNA or RNAi.

34. The method of claim 29, wherein the method comprises stably transforming the plant or plant cell with the expression cassette.

35. A method of expressing a nucleotide sequence in a plant comprising: stably transforming a plant cell with the expression cassette of claim 3, regenerating a stably transformed plant, and expressing the heterologous nucleotide sequence of interest in the plant.

36. The method of claim 35, wherein the plant is a monocotyledonous plant.

37. The method of claim 35, wherein the heterologous nucleotide sequence of interest encodes a polypeptide.

38. The method of claim 37, further comprising the step of collecting the polypeptide.

39. The method of claim 35, wherein the heterologous nucleotide sequence of interest is transcribed to produce an antisense RNA or RNAi.

40. An isolated expression cassette comprising a nucleic acid having a nucleotide sequence selected from the group consisting of:
  (a) the nucleotide sequence of SEQ ID NO:2;
  (b) a nucleotide sequence having at least 98% sequence identity to the nucleotide sequence of (a); and
  (c) a nucleotide sequence having at least 500 consecutive nucleotides of the nucleotide sequence of SEQ ID NO:2,
wherein said nucleotide sequence selected from the group consisting of (a), (b) and (c) has promoter activity; and further wherein:
  (i) said nucleotide sequence selected from the group consisting of (a), (b) and (c) is operably linked with a heterologous nucleotide sequence of interest; or
  (ii) said nucleotide sequence selected from the group consisting of (a), (b) and (c) further comprises a plurality of restriction sites for insertion of a heterologous nucleotide sequence of interest to be operably linked to said nucleotide sequence selected from the group consisting of (a), (b) and (c).

41. The expression cassette of claim 40, wherein said nucleotide sequence has at least 98% sequence identity to the nucleotide sequence of (a).

42. The expression cassette of claim 40, wherein said nucleotide sequence is the nucleotide sequence of SEQ ID NO:2.

43. The expression cassette of claim 40, wherein said nucleotide sequence selected from the group consisting of (a), (b) and (c) is operably linked with a heterologous nucleotide sequence of interest, as set forth in part (i).

44. The expression cassette of claim 43, wherein said heterologous nucleotide sequence of interest encodes a polypeptide.

45. The expression cassette of claim 40, further comprising a nucleotide sequence that encodes a selectable marker.

46. A plant cell comprising the expression cassette of claim 44.

47. The expression cassette of claim 6, wherein said selectable marker comprises an herbicide resistance gene.

48. The expression cassette of claim 45, wherein said selectable marker comprises an herbicide resistance gene.

49. The expression cassette of claim 40, wherein said nucleotide sequence comprises at least 500 consecutive nucleotides of SEQ ID NO:2.

50. The expression cassette of claim 40, wherein said nucleotide sequence comprises at least 700 consecutive nucleotides of SEQ ID NO:2.

51. The expression cassette of claim 40, wherein said nucleotide sequence has at least 99% sequence identity to the nucleotide sequence of (a).

52. The expression cassette of claim 1, wherein said expression cassette further comprises a plurality of restriction sites for insertion of a heterologous nucleotide sequence of interest to be operably linked to said nucleotide sequence selected from the group consisting of (a) and (b), as set forth in part (ii).

53. The expression cassette of claim 40, wherein said expression cassette further comprises a plurality of restriction sites for insertion of a heterologous nucleotide sequence of interest to be operably linked to said nucleotide sequence selected from the group consisting of (a), (b) and (c), as set forth in part (ii).

* * * * *